(12) United States Patent
Tuttle et al.

(10) Patent No.: US 8,734,453 B2
(45) Date of Patent: May 27, 2014

(54) INSTRUMENTS FOR MINIMALLY INVASIVE SURGERY TOTAL KNEE ARTHROPLASTY

(75) Inventors: David R. Tuttle, Memphis, TN (US); Brian R. Harris, Cordova, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 1771 days.

(21) Appl. No.: 11/358,899

(22) Filed: Feb. 21, 2006

(65) Prior Publication Data

US 2006/0241634 A1    Oct. 26, 2006

Related U.S. Application Data

(60) Provisional application No. 60/654,441, filed on Feb. 21, 2005, provisional application No. 60/723,092, filed on Oct. 3, 2005.

(51) Int. Cl.
*A61F 5/00* (2006.01)
(52) U.S. Cl.
USPC .......................................................... 606/87
(58) Field of Classification Search
USPC ................................ 606/79, 80, 86 R, 87–89
See application file for complete search history.

(56) References Cited

U.S. PATENT DOCUMENTS

| 6,458,135 | B1 * | 10/2002 | Harwin et al. | 606/88 |
| 6,979,299 | B2 * | 12/2005 | Peabody et al. | 600/587 |
| 7,104,996 | B2 * | 9/2006 | Bonutti | 606/86 R |

* cited by examiner

*Primary Examiner* — Sameh Boles
(74) *Attorney, Agent, or Firm* — Duane Morris LLP

(57) ABSTRACT

An anti-backout stylus comprising a stylus and a locking stylus holder. The locking stylus holder engages the stylus at a series of discrete positions during insertion of the stylus into the holder. The locking stylus holder prevents inadvertent backing out of the stylus by preventing the stylus from being withdrawn to a previous one of the discrete positions. The locking stylus holder can preferably be selectively disengaged from the stylus to allow for selective withdrawal of the stylus. Each engagement of one of the discrete positions by the locking stylus holder preferably indicates a femoral size. The discrete positions are preferably defined by detents formed on the stylus and a stop member on the locking stylus holder. The locking stylus holder can be provided on an anterior rough cut guide, with the anterior rough cut guide preferably mountable on an intramedullary rod.

15 Claims, 56 Drawing Sheets

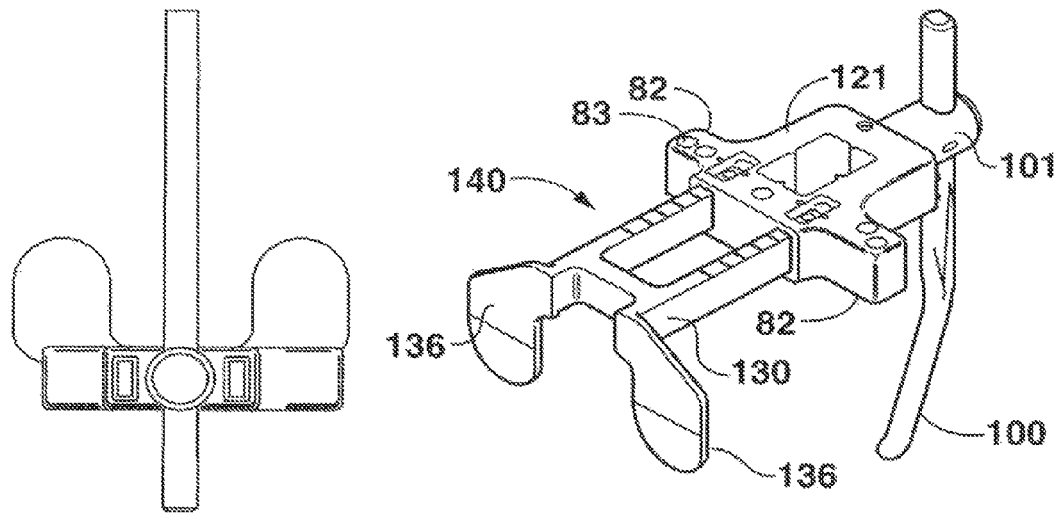
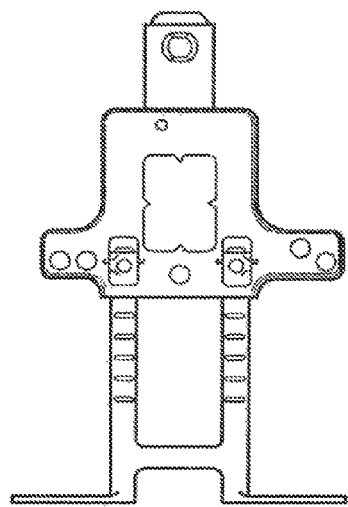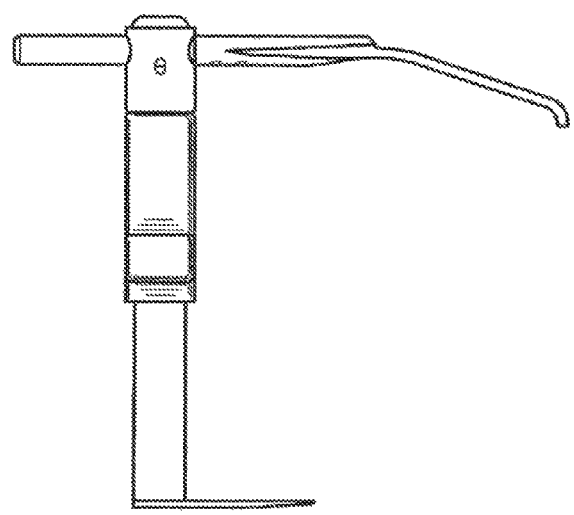
FIG. 4B-2  FIG. 4B-1
FIG. 4B-3  FIG. 4B-4

INSTRUMENTS FOR MINIMALLY INVASIVE SURGERY TOTAL KNEE ARTHROPLASTY

CROSS REFERENCE TO RELATED APPLICATIONS

This application claims priority to and incorporates by reference Provisional Patent Application Ser. No. 60/654,441, filed Feb. 21, 2005 and Provisional Patent Application Ser. No. 60/723,092, filed Oct. 3, 2005.

FIELD OF THE INVENTION

The present invention relates to orthopedic surgery, and more particularly to instruments for use in minimally invasive total knee arthroplasty.

BACKGROUND OF THE INVENTION

Total knee implants have been around for many years. Over the years, various instruments have been developed for preparing the distal femur and the proximal tibia for receipt of knee implants. In recent years, efforts have been made to minimize the length of the incision by applying "minimally invasive surgery" ("MIS") techniques to total knee arthroplasty ("TKA") procedures. MIS TKA procedures minimize trauma to tissues and reduce patient recovery time. MIS TKA procedures attempt to use the smallest incision possible. However, the length of the incision is constrained by several factors, including the size of the implant, the size and type of instruments used to resect the knee, the necessity of making accurate recisions, the need to minimize trauma to the skin in the area around the incision, and the skill and experience level of the surgeon. The present application is directed to MIS TKA instruments that are particularly adapted for making accurate femoral resections within the confined spaces encountered in MIS TKA procedures. The instruments minimize damage to the skin and assist both experienced and less experienced surgeons in successfully carrying out MIS TKA procedures.

The following background material is incorporated from applicant's co-pending U.S. patent application Ser. No. 10/794,188 (Publication No. 2005/0209600), which is incorporated herein by reference. Performance of a knee replacement surgery typically includes modification of one, or both, of the proximal end of the tibia and the distal end of the femur to have a shape that accommodates the tibial and femoral components, respectively, of the knee prosthesis. Modification typically involves some type of cutting procedure, e.g., with a bone saw, to prepare planar surfaces on the femur for attachment of the femoral component. An effective attachment of the femoral component to the femur is facilitated by cutting the femur at appropriate depths and angles that match the dimensions and angles of the attachment (i.e., non-articulating) surfaces on the underside of the femoral component.

The femur, due to its complex geometry (e.g., lateral and medial condyles and intracondylar notch) can be particularly difficult to shape and therefore benefits greatly from accurate cuts. In addition, proper sizing of the components is important to ensure that the knee prosthesis has adequate stability and range of motion. To this end, various calipers and resection guides have been developed that measure the tibia and femur to determine appropriate sizes for the femoral and tibial components.

The ADVANCE® brand single reference point knee replacement system (Wright Medical, Inc., Arlington, Tenn.) includes a femoral caliper that works off of a single reference point to size the femoral component. The knee replacement system also includes a guide for guiding subsequent cuts to the femur. During femur preparation, first, a starter hole is initiated in the femoral (medullary) canal between the condyles using a drill bit. A fluted intramedullary reamer is inserted into the femoral canal and is turned by hand by grasping and twisting a T-handle end attachment to reduce the occurrence of fat embolisms. An intramedullary alignment rod is then inserted into the reamed hole, preferably at a valgus angle of about 3° or 5°, and becomes the single point from which the remaining cuts are referenced.

A distal femoral resection guide is then assembled onto the intramedullary rod and is placed against the most prominent distal femoral condyle. The resection guide includes slots that are sized to support a bone saw (or other) blade as it cuts a section of the distal femur to form a flat surface in a "distal rough cut." After the initial cut, the distal surface can then be gently planed until flat by a planer that is rotated about the intramedullary rod. The preferred amount of distal resection is between 9 mm and 13 mm.

After planing, the femoral sizing caliper is placed over the intramedullary rod and against the flat, resected distal femur. A pair of feet of the femoral sizing caliper are placed adjacent the posterior portion of the medial and lateral femoral condyles, while a feeler gauge is placed in contact with the anterior cortex of the femur. Movement of the feeler gauge and the feet into position registers a size on a sizing guide of the femoral sizing caliper.

Once the component size has been determined, an anterior-posterior resection guide corresponding to the previously measured size of the femoral component is placed over the intramedullary rod. The anterior-posterior resection guide is moved posteriorly until an anterior feeler gauge of the anterior-posterior resection guide contacts the anterior cortex of the femur. Additional anterior-posterior adjustments can be made using an anterior-posterior positioning screw which moves the resection guide in the anterior-posterior direction in small increments with respect to the feeler gauge. Proper positioning is confirmed by examining the anterior-posterior resection guide to ensure that about 2 mm to 4 mm of posterior condyle is visible under the resection guide.

A locking screw is tightened to secure the anterior-posterior resection guide once it has been positioned as desired and slots defined in the guide are used to complete various other cuts, such as the anterior and posterior chamfer cuts. Additional guides are attached in a similar manner to make other cuts. After all of the cuts have been made, the distal femur has a shape congruent to the attachment surface of the femoral component and the femoral component can be attached to the distal femur.

During this process, a sometimes difficult aspect of femoral component sizing is selecting a size for the femoral component when the femur, which has a natural biological variation in size and morphology from patient to patient, falls in between two sizes. The ADVANCE® brand single reference point knee replacement system generally recommends that a smaller size be selected in such a situation to avoid "overstuffing" the knee in flexion, in other words, to avoid a knee that is too tight and resists full extension. Of course, selecting a smaller size can also result in a somewhat increased laxity of the joint at high knee flexion angles.

In addition to the ADVANCE® Single Reference Point brand knee replacement system, other systems are used for preparing the femur for attachment of a femoral prosthesis. Another single reference point system is described in U.S. Pat. No. 4,474,177 to Whiteside. Also, systems that do not use a single reference point can be employed. For example, there is also an ADVANCE® brand distal cut first knee replacement system that uses an intramedullary rod as a reference point to guide an initial distal cut. However, the remaining surgical steps, such as femoral component sizing and the anterior-posterior cuts, are referenced off of the resected distal femoral surface.

Despite the effectiveness of the above-listed knee replacement systems, additional improvements in systems and methods for preparing the distal femur for attachment of a femoral component are always desirable.

OBJECTS AND SUMMARY OF THE INVENTION

It is an object of the invention to provide instruments and methods for use in minimally invasive total knee arthroplasty.

It is another object of the invention to provide instruments that improve the ease and accuracy of minimally invasive total knee arthroplasty procedures.

It is another object of the invention to provide surgeons with various options for performing minimally invasive total knee arthroplasty.

The foregoing and other objects and advantages of the invention are achieved using the various instruments and procedures described herein. Of the various instruments described herein, the claims of the present application are directed to an anti-backout stylus instrument assembly. The anti-backout stylus instrument assembly comprises, generally, a stylus configured for insertion into a locking stylus holder and a locking stylus holder. The locking stylus holder is configured to engage the stylus at a series of discrete positions during insertion of the stylus into the locking stylus holder. The locking stylus holder is also configured to prevent the stylus from being withdrawn to a previous one of the discrete positions, which prevents inadvertent backing out of the stylus from the locking stylus holder. The discrete positions are preferably defined by detents formed on the stylus and a stop member on the locking stylus holder. The locking stylus holder can be provided on an anterior rough cut guide, with the anterior rough cut guide preferably mountable on an intramedullary rod in the femur.

The assembly is preferably provided with a disengagement member on the locking stylus holder. The disengagement member is configured to selectively disengage the locking stylus holder from the stylus, and thereby allow the stylus to be withdrawn through the stylus holder. The disengagement member preferably comprises a part of the stylus bore of the locking stylus holder being formed by a biased button, with the biased button configured such that a user can selectively backout the stylus from the locking stylus holder by depressing the biased button and simultaneously pulling the stylus rearward. The biased button preferably has a stop member on a lower interior wall, the biased button normally biased upward such that the stop member is positioned to engage one of a series of detents formed along a lower surface of an engagement portion of the stylus. The biased button is preferably biased by a captured spring.

In a preferred embodiment, each of the discrete positions matches a particular femoral size, such that each engagement of one of the discrete positions by the locking stylus holder indicates a femoral size. Each engagement of one of the discrete positions by the locking stylus holder produces a sound, such that the sound provides an indication of a femoral size. Femoral size markings can also be provided on the stylus for use in visually determining a femoral size.

BRIEF DESCRIPTION OF THE DRAWINGS

FIGS. 4B-1, 4B-2, 4B-3, and 4B-4 provide a perspective view of one preferred embodiment of a universal anterior-posterior positioning and posterior sizing caliper.

PREFERRED EMBODIMENTS OF THE INVENTION

Figure 1:
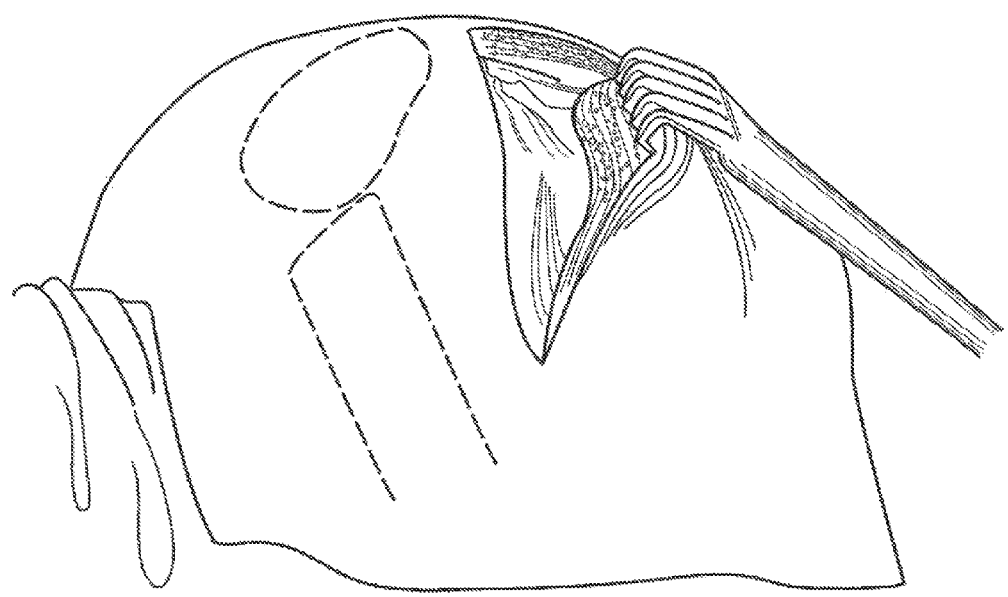
FIG. 1 shows a preferred anterior-medial approach for use in the carrying out the procedures of the invention.

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

As shown in the drawings and discussed in detail below, the invention generally comprises instruments and surgical techniques for performing a minimally invasive resection of a distal femur using a medial approach. The instruments and techniques of the invention allow a total knee arthroplasty ("TKA") to be performed through a single incision.

Quad Sparing Anterior Medial Approach

As indicated in FIG. 1, the preferred approach for the procedures of the invention is generally anterior-medial through an incision commencing at approximately the proximal or superior end of the patella and extending distally in a generally sagittal orientation. The preferred incision is approximately twice the length of the patella (about 4 to 5 inches or 10 to 13 cm).

Patella Resection

Figure 10:
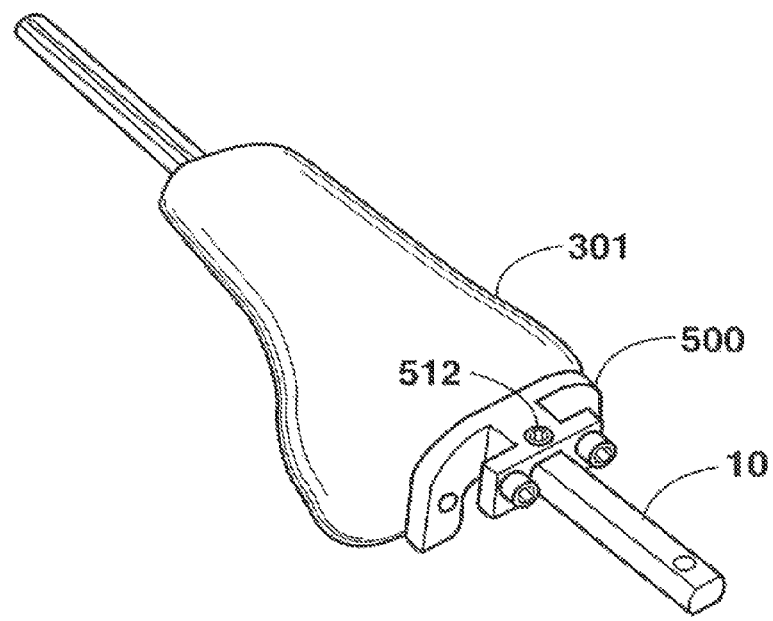
FIGS. 10, 11P, 11B, 12, 13P, 13B, 13C, and 14-18 provide views of steps in a preferred MIS anterior rough cut procedure.

To assist in providing a minimally invasive approach, the patella is resected at the beginning of the procedure. The patella resection can be carried out using instruments and techniques known to those of skill in the art. A preferred embodiment of a patella clamp 500 is shown in FIG. 10. The opposing jaws 501A, 501B of the patella clamp bend downward at approximately 90 degrees. The bent configuration of the jaws 501A, 501B allows the surgeon to grab the patella in an anatomical position and then rotate 30 to 90 degrees to make the resection. The patella clamp 500 also preferably has a depth gage that allows the surgeon to grasp the patella and resect without everting the patella.

Because the patella is prepared at the beginning of the procedure, the patella can potentially be damaged during later stages of the operation. To avoid damage, the patella is optionally fitted with a removable cap that is configured to protect the resected surface and/or the peripheral edges of the patella, in manner known to those of skill in the art.

Alignment of Intramedullary Rod

As indicated in FIG. 1, a fixed reference for the resection procedure is created by inserting an intramedullary rod 10 into the intramedullary canal of the femur. The intramedullary rod 10 is positioned in the bottom of the sulcus in a manner known to those of skill in the art (see e.g. U.S. Pat. No. 4,474,177, which is incorporated herein by reference). The alignment or final rotational position of the intramedullary rod 10 can be set using an alignment guide, such as a modified trochlear axis guide (see e.g. U.S. Pat. No. 6,159,217, which is incorporated herein by reference) or a crosshair alignment guide. As will be discussed in further detail below, the final rotational position of the intramedullary rod 10 provides a fixed reference point that is used to determine the final rotation of the implant, which assists in providing a minimally invasive approach.

Figure 1P:
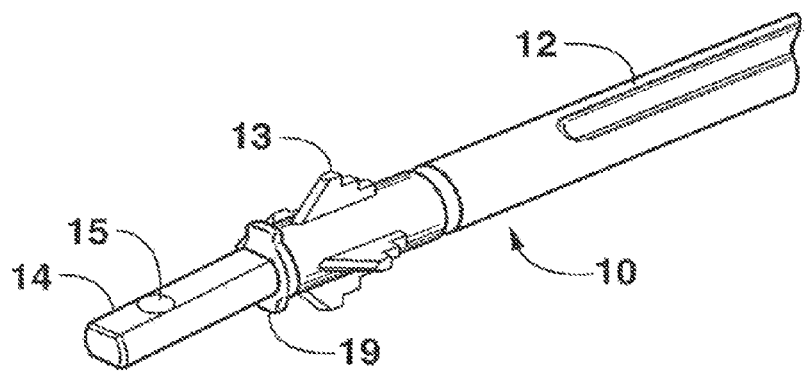
FIG. 1P provides a perspective view of one preferred embodiment of an intramedullary rod for use in carrying out the procedures of the invention.

A preferred embodiment of an intramedullary rod 10 for use in the invention is shown in FIG. 1P. The embodiment of FIG. 1P is a one piece or unibody rod having an intramedullary stem 12 on a proximal end and a guide mount 14 portion on a distal end. The guide mount 14 has a non-circumferential cross-section in order to prevent rotation of cutting guide instruments when mounted on the guide mount 14. In the preferred embodiment shown in FIG. 1P, the cross-section has a race track or modified ellipsoidal configuration having a pair of substantially parallel flat surfaces interposed between oppositely oriented curved surfaces. An aperture 15 preferably extends through the guide mount 14.

As shown in FIG. 1P, a stop member 19 is positioned proximal to the guide mount 14 for preventing the guide mount portion 14 from entering the intramedullary canal. As shown in FIG. 1P, the stop member 19 preferably comprises two or more tabs extending axially from the intramedullary rod. One or a plurality of anti-rotation fins 13 are fixed proximal to the stop 19 for preventing rotation of the intramedullary rod 10 following insertion into the intramedullary canal.

Figure 1B:
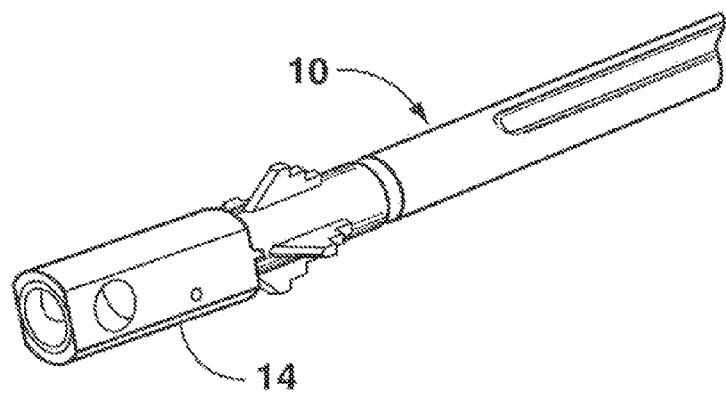
FIG. 1B provides a perspective view of one preferred embodiment of an intramedullary rod having a detachable guide mount.

FIG. 1B shows an alternative embodiment of an intramedullary rod 10 having a removable guide mount 14. The removable guide mount 14 can be selectively locked into a fixed orientation on the stem portion 12 of the intramedullary rod 10. In one embodiment, the removable guide mount 14 threads onto the intramedullary rod 10. The removable guide mount 14 can be removed to allow the knee to be flexed or extended for improved visualization without losing anchor position. In one embodiment, the intramedullary rod 10 is configured to provide a recessed intramedullary rod 10 in which the entire body of the intramedullary rod 10 resides inside of the intramedullary canal, including the distal end of the rod 10. The removable guide mount 14 can be provided with a threaded shaft on a proximal end, the shaft sized to thread into a threaded bore on a distal end of the recessed intramedullary rod 10. A recessed intramedullary rod 10 and removable guide mount 14 combination allows a full distal cut, including a full distal cut first, to be made from an anterior or medial approach without impingement by the recessed intramedullary rod 10. In both the unibody and two part intramedullary rod 10 embodiments, the guide mount 14 is preferably sized and configured to provide a smaller attachment area than that of conventional intramedullary rods, which assists in providing a minimally invasive approach.

Medial Distal Cut

Figure 2P:
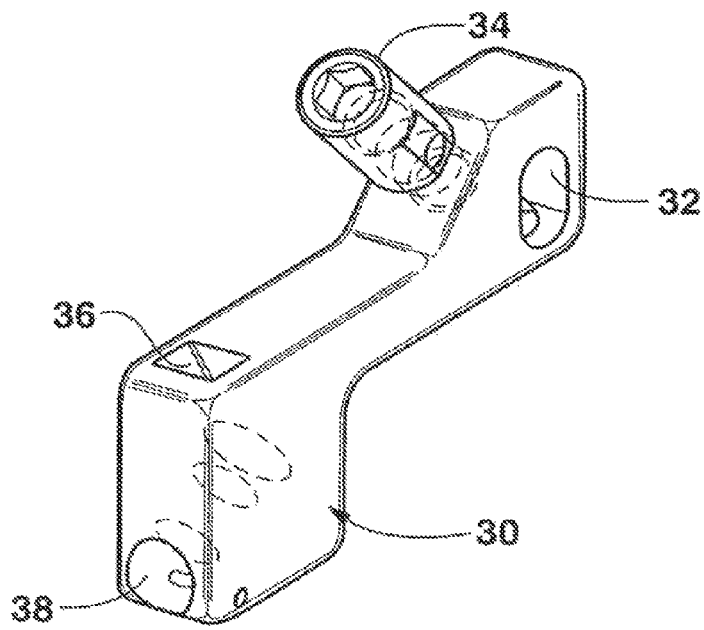
FIG. 2P provides a perspective view of one preferred embodiment of a medial distal cut paddle.
Figure 2:
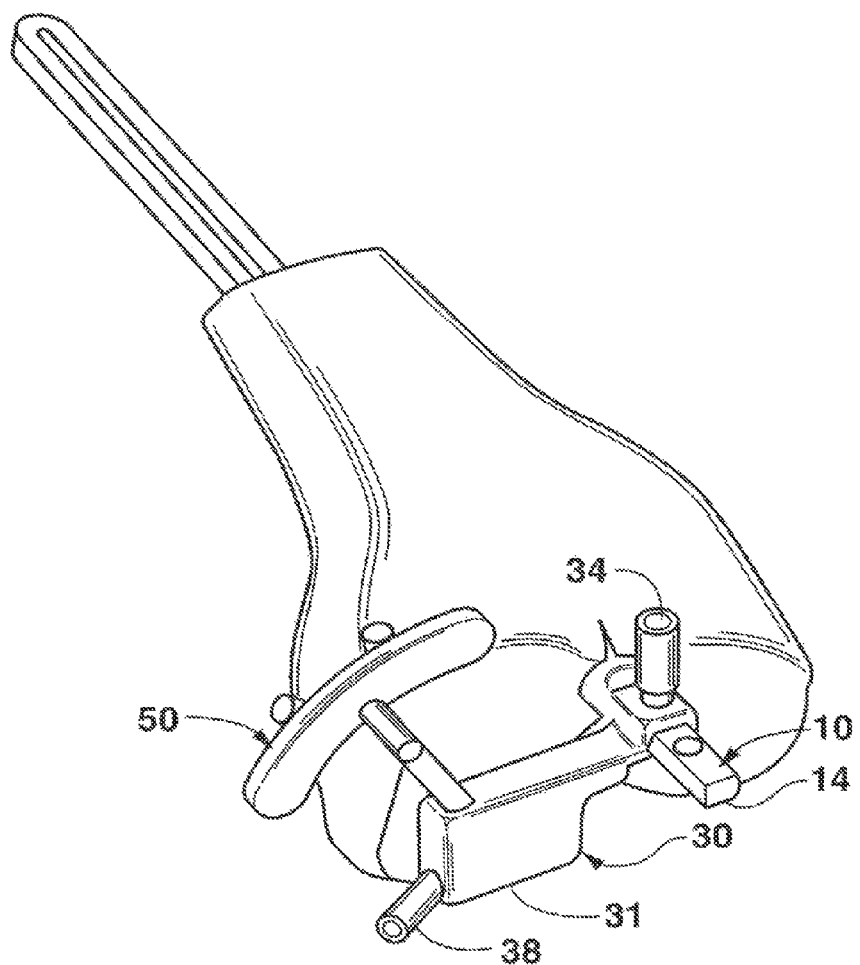
FIG. 2 shows a perspective view of one preferred embodiment of a medial distal cut paddle and a medial distal cut guide mounted on an intramedullary rod, along with a resection of the medial distal femur.

As indicated in FIG. 2, the resection procedure of the invention preferably uses a medial distal cut first. As shown in FIG. 2, a medial distal cut paddle 30 and a medial distal cut guide 50 are attached to the intramedullary rod 10 for use in making the medial distal cut first.

As shown in FIG. 2, the medial distal cut paddle 30 includes a platform 31 which preferably has a flat profile on at least a proximal side thereof. As shown in the preferred embodiment of FIG. 2P, the medial distal cut paddle 30 has an intramedullary rod aperture 32 for use in attaching the medial distal cut paddle 30 to the intramedullary rod 10. As shown in FIG. 2P, the intramedullary rod aperture 32 is sized and configured to closely receive the guide mount 14 of the intramedullary rod 10, to thereby prevent rotation of the medial distal cut paddle 30 relative to the intramedullary rod 10. A clamp bolt 34 threads through the medial distal cut paddle 30 in association with the intramedullary rod aperture 32 such that a distal end of the clamp bolt 34 selectively engages the guide mount 14 of the intramedullary rod 10, thus preventing the medial distal cut paddle 30 from sliding along the guide mount 14. As indicated in FIG. 2, the medial distal cut paddle 30 is seated on the intramedullary rod 10 until the platform 31 contacts the most prominent portion of the medial distal condyle. As will be discussed in further detail below, fixing the medial distal cut paddle 30 on the guide mount 14 of the intramedullary rod 10 provides a fixed frame of reference that is later translated to the medial distal femur.

Figure 2B:
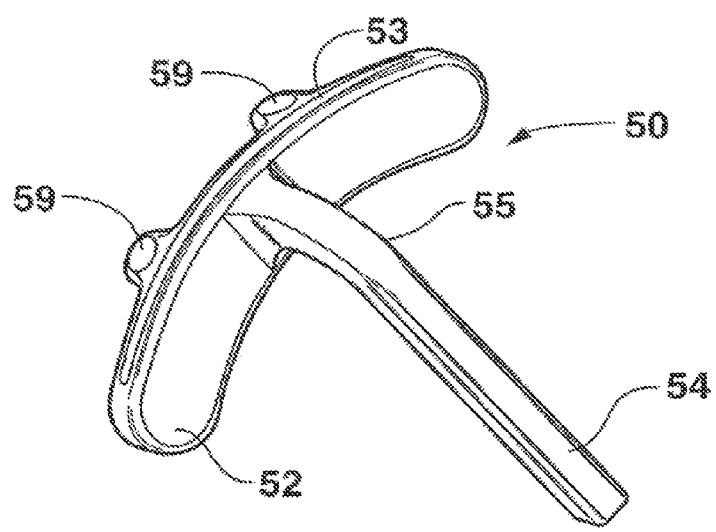
FIG. 2B provides a perspective view of one preferred embodiment of a medial distal cut guide.

FIG. 2B shows a preferred embodiment of a medial distal cut guide 50 for use with the medial distal cut paddle 30. As shown in FIG. 2B, the medial distal cut guide 50 includes a generally flattened cut guide portion 52 having a cutting slot 53 formed therethrough for receiving a conventional saw blade (not shown). The medial distal cut guide 50 includes a stem portion 54, which is connected to the cut guide portion 52 via a curved or offset section 55. In a surgical kit, a plurality of medial distal cut guides 50 are preferably provided, with each guide 50 having a different size offset 55 in order to allow a surgeon to select an appropriate resection depth for the medial distal cut. As indicated in FIG. 2, the curved section of the offset 55 offsets the cutting slot 53 from the stem portion 54, and thus from the platform 31 of the medial distal cut paddle 30. The medial distal cut guide 50 can optionally be provided with one or more fixation bores 59 on a proximal side of the cut guide portion 52 for use in fixing the cut guide portion 52 on the femur with pins or screws. The cut guide portion 52 preferably has a curved or arcuate shape in order to better fit the anatomy of the distal condyle. In a surgical kit, the stem 54 can be provided in a variety of lengths to accommodate different sizes of femurs.

In FIG. 2, the medial distal condyle cut guide 50 is shown attached to the medial distal cut paddle 30. As shown in FIG. 2P, the medial distal cut paddle 30 has a cut guide bore 36 formed through the platform portion 31. The cut guide bore 36 is sized and configured to closely receive the stem portion 54 of the medial distal cut guide 50 in a sliding engagement. The sliding engagement between the stem 54 and cut guide bore 36 allows for selective positioning of the cut guide portion 52 relative to the distal end of the femur. Additionally, the cut guide bore 36 is oriented at a selected angle relative to the guide mount 14 and intramedullary rod aperture 32, such that the cut guide portion 52 can be used through an anterior-medial incision. As shown in FIG. 2, a clamp bolt 38 threads through the distal condyle platform 31 in association with the cut guide bore 36 for use in selectively locking the stem 54 of the distal cut guide 50 relative to distal condyle platform 30. Optionally, a second cut guide bore (not shown) can be added to the distal condyle platform 30 to provide an option for a more medial approach.

Figure 2C:
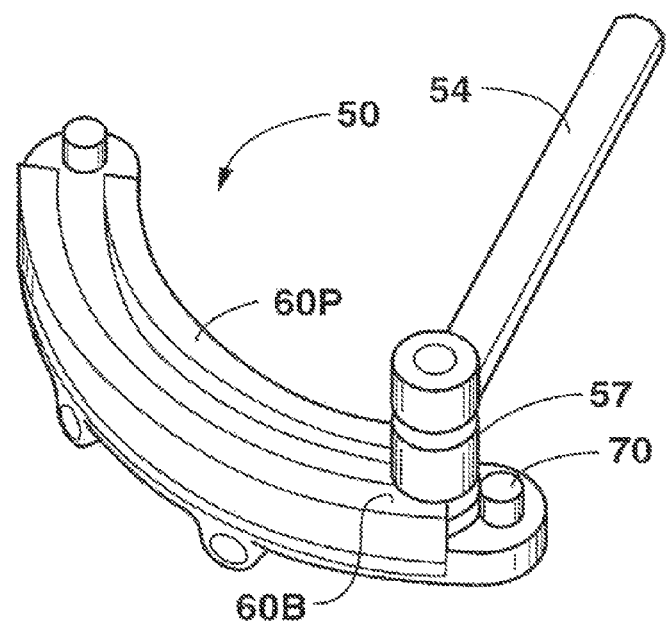
FIG. 2C provides a perspective view of one preferred embodiment of a medial distal cut guide.
Figure 2D:
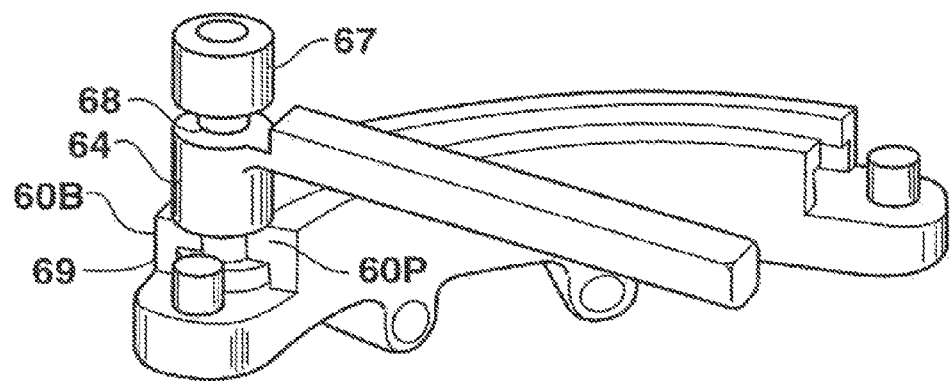
FIG. 2D provides a perspective view of one preferred embodiment of a medial distal cut guide.

FIGS. 2C and 2D show an alternative preferred embodiment in which the stem 54 of the medial distal cut guide 50 is slidingly attached to the cut guide portion 52. This feature allows a surgeon additional options for selectively positioning the cut guide portion 52 in order to optimize the direction of the distal resection. The positionable distal cut guide 50 of FIGS. 2C and 2D has a locking means for use in locking the stem 54 is a selected position relative to the cut guide portion 52. In the preferred embodiment shown in FIGS. 2C and 2D, the locking means includes a pair of retaining tracks 60A, 60B. An eye 57 is formed on a proximal end of the stem 54. A bolt 68 passes through the stem eye 57 in an inverted position, such that the head 69 of the bolt 68 is retained by the opposing tracks 60A, 60B of the cut guide portion 52. A nut 67 is threaded onto the bolt 68. When the nut 67 is rotated to decrease the distance between the nut 67 and the bolt head 69, the nut 67 compresses the eye 57 of the stem 54 against the retaining tracks 60A, 60B, which retains the stem 54 in a fixed position on the cut guide portion 53. The nut 67 can be loosened in order to selectively reposition the stem 54. The adjustable distal cut guide 50 of FIGS. 2C and 2D allows the surgeon to select an approach that is more medial, anterior-medial or anterior, depending on the preference of the surgeon and the needs of the particular case, which further contributes to a minimally invasive approach.

Figure 9:
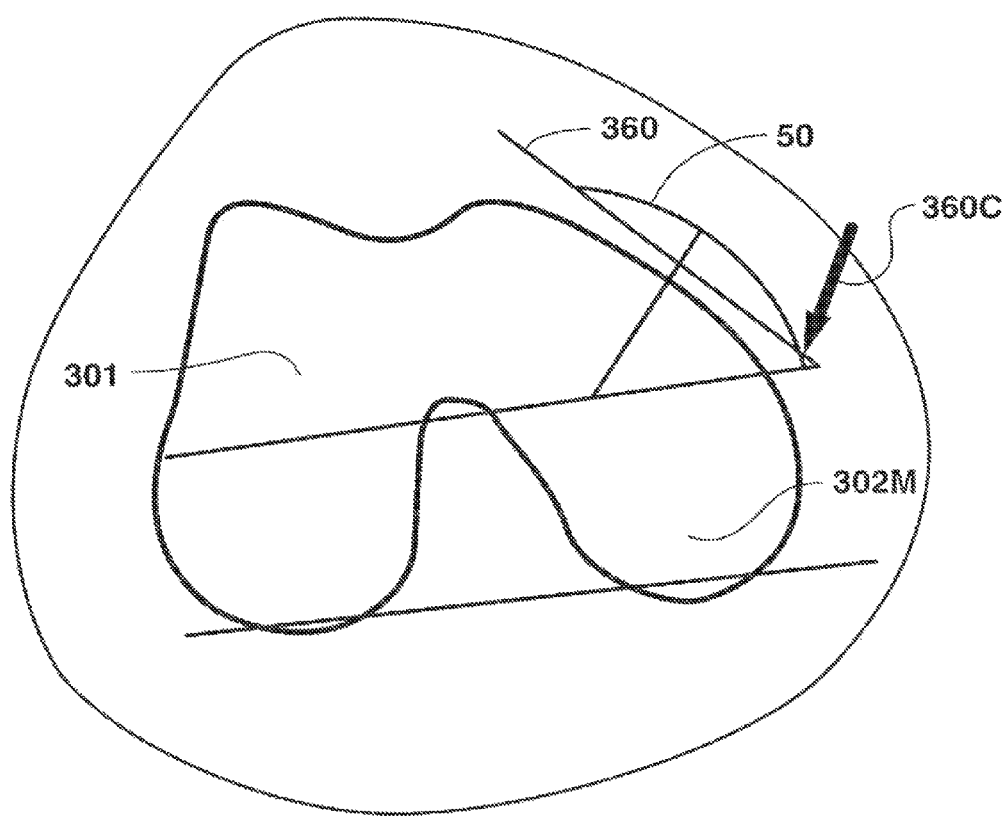
FIG. 9 is a transverse view of the distal femur 301 showing a preferred orientation of the medial distal rough cut.

FIG. 9 is a transverse view of the distal femur 301 showing a preferred orientation of the medial distal rough cut using the instruments and techniques described herein. The approximate anterior-medial slope of the medial distal condyle 302M is indicated by line 360. Line 50 indicates the preferred orientation of the medial distal cut guide 50 relative to the anterior-medial slope 360 of the medial distal condyle 302M. A preferred orientation of the medial distal rough cut is indicated by arrow 360C. As indicated in FIG. 9, the medial distal rough cut 360C is preferably made substantially along the anterior-medial slope 360 of the medial distal condyle 302M. The cut 360C is directed anterior-medially at an angle that is roughly perpendicular to the slope of anterior-medial slope 360 of the medial distal condyle 302M.

Position of Anterior Reference

After the medial distal condyle has been resected, the femur is sized. Sizing is preferably done in a two step procedure that contributes to the minimally invasive approach of the invention. In the first step, shown in FIG. 3, an anterior-posterior positioning caliper or anterior reference jig 80 is used to establish an anterior reference 303 (e.g. a peg position or an arbitrary reference point). In the second step, shown in FIG. 4, a posterior sizing caliper or posterior sizer 120 is used to determine the size of the femoral implant with reference to the anterior reference and the medial posterior condyle (see FIG. 4).

Figure 3P:
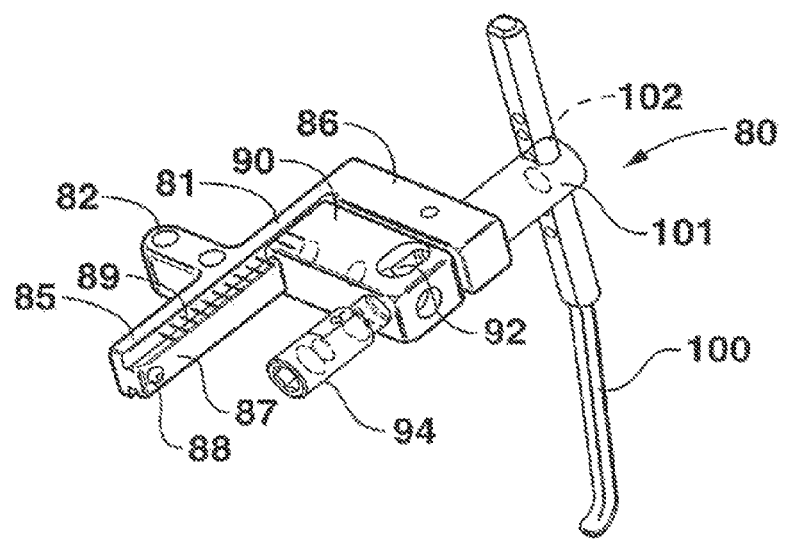
FIG. 3P provides a perspective view of one preferred embodiment of an anterior-posterior positioning caliper, and featuring a view of a removable stylus.
Figure 3:
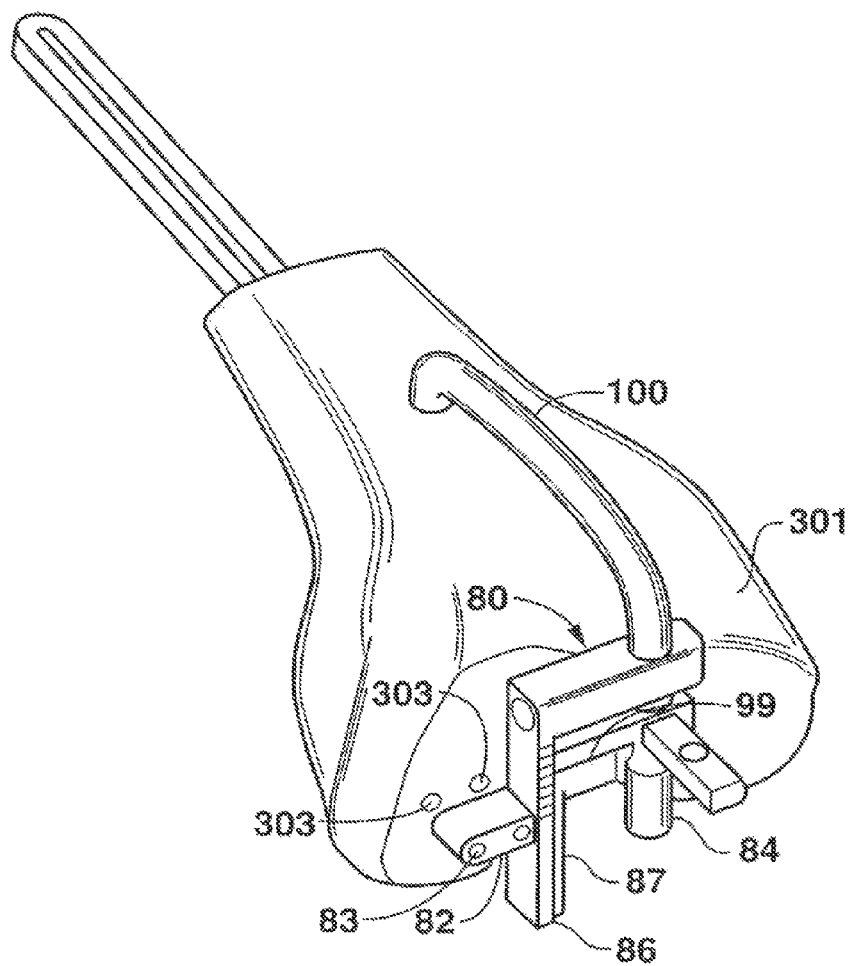
FIG. 3 shows a perspective view of one preferred embodiment of an anterior-posterior positioning caliper mounted on an intramedullary rod for use in sizing a femur and translating a reference point from the intramedullary rod to a secondary reference point on the medial distal cut femur.

FIGS. 3 and 3P show alternative preferred embodiments of an A-P positioning caliper or anterior reference jig 80 for use in establishing an anterior reference on the resected medial distal condyle. The A-P positioning caliper 80 is configured to allow for ready translation of rotation or position from the intramedullary rod 10 to the medial condyle. FIG. 3 shows the A-P positioning caliper 80 positioned on the guide mount 14 of the intramedullary rod 10. As shown in FIG. 3, a proximal end of an anterior stylus 100 contacts the anterior cortex of the femur. As indicated in FIG. 3, a drill guide 82 is used to establish a reference point on the resected medial distal femur. Details of preferred embodiments of the A-P positioning caliper 80 will now be described, with particular reference to FIG. 3P.

The A-P positioning caliper 80 shown in FIG. 3P includes a reference bar 81 that has an inverted "L" configuration. As shown in FIG. 3P, the reference bar 81 includes a vertical bar portion 85 and a horizontal bar portion 86 extending from an upper end of the vertical bar portion 85. A vertical retaining track 87 is formed along a medial side of the vertical bar portion 85 of the reference bar 81. A retaining arm 90 is slidably engaged to the vertical track 87 in a substantially perpendicular relationship to the vertical bar portion 85. A stop 88 preferably retains the retaining arm 90 on the reference bar 81 when the retaining arm 90 reaches the bottom of the vertical track 87. The retaining arm 90 of the A-P positioning caliper 80 includes an intramedullary rod aperture 92, which is sized to closely receive the intramedullary rod 10. A locking means such as a clamp bolt 94 is associated with the intramedullary rod aperture 92 for use in selectively locking the retaining arm 90 on the guide mount 14 of the intramedullary rod 10. As indicated in FIG. 3, the retaining arm 90 remains in a fixed position on the intramedullary rod 10, while the reference bar 81 can be selectively raised or lowered along the retaining arm 90 for use in anterior-posterior positioning.

As shown in FIG. 3P, a set of calibration marks or a calibration scale 89 is provided on the vertical bar portion 85 of the reference bar 81 for use in modifying the A-P position or to provide a reference for the next block. One or more reference marks 99 are also provided on the retaining arm 90 for use in conjunction with the calibration scale 89.

As shown in FIG. 3P, an anterior stylus 100 is attached to an upper portion of the A-P positioning caliper 80. The stylus 100 is preferably removable from the A-P positioning caliper 80. In the embodiment shown in FIG. 3P, the A-P positioning caliper 80 includes a stylus holder 101 which projects upward from the horizontal bar portion 86. The stylus holder 101 includes a stylus bore 102 for receiving an anterior stylus 100. The stylus bore 102 is sized and configured to closely receive a portion of the stylus 100. In the embodiment of FIG. 3P, the stylus 100 can slide proximally and distally to ease insertion, which assists in providing a minimally invasive approach. The anterior stylus 100 is available in various configurations (e.g. standard; +2 mm; −2 mm) for use in making secondary adjustments. Although the stylus 100 is detachable, a locking means may be provided for selectively locking the stylus 100 in position on the A-P positioning caliper 80.

Figure 3B:
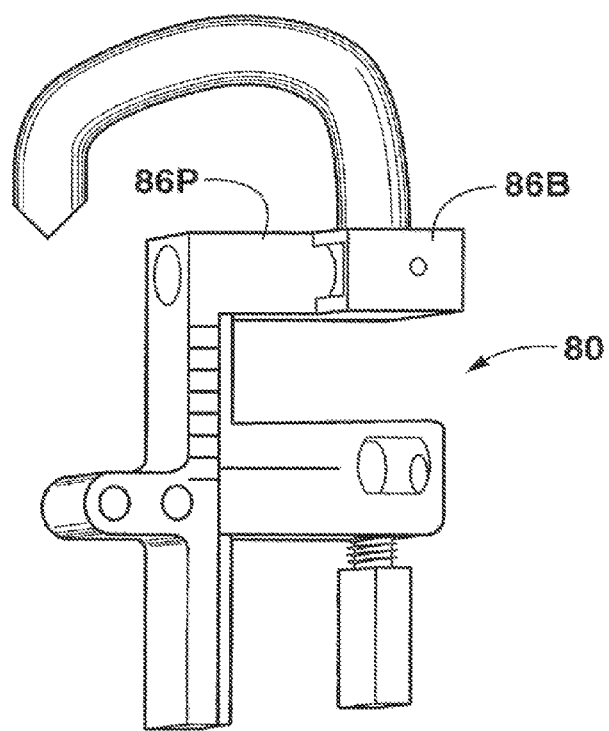
FIG. 3B provides a perspective view of one preferred embodiment of an anterior-posterior positioning caliper.

The embodiment of FIG. 3B includes a two part horizontal bar portion 86A, 86B having a stationary portion 86A and a positionable portion 86B. The positionable portion 86B slidably engages the stationary portion 86A. This embodiment allows the stylus 100 to slide proximally and distally to ease insertion, and thus assists in providing a minimally invasive approach.

As shown in FIG. 3P, a drill guide 82 extends from the vertical bar portion 85 of the A-P positioning caliper 80. The drill guide is provided with one or more drill holes 83 for use in establishing an A-P position or secondary reference point 303 on the medial cut of the distal femur 301, and thus to translate rotation or position from the intramedullary rod 10 to the medial condyle. Because the A-P positioning caliper 80 attaches to the intramedullary rod 10, only one reference hole 83 is required for translating the position of the secondary reference point. Alternatively, a plurality of holes 83 can be used to establish the secondary reference point or points 303, which serves to translate both position and rotation from the primary reference point. The secondary reference point 303 can have a non-symmetric geometry. In a preferred embodiment, the drill guide 82 is provided with two drill holes 83, as shown in FIG. 3. The secondary reference position 303 may or may not be the position of the final implant. Additionally, the A-P positioning caliper 80 can be used with or without an intramedullary rod 10, for example by inserting the peg(s) 123 of the posterior sizing caliper 120 into the hole(s) 83 of the A-P positioning caliper 80.

The A-P positioning caliper 80 preferably has a universal configuration, which allows it to be used for a left or a right knee procedure. A universal configuration reduces the number of instruments that must be provided in an MIS surgical kit.

Posterior Sizing

Figure 4:
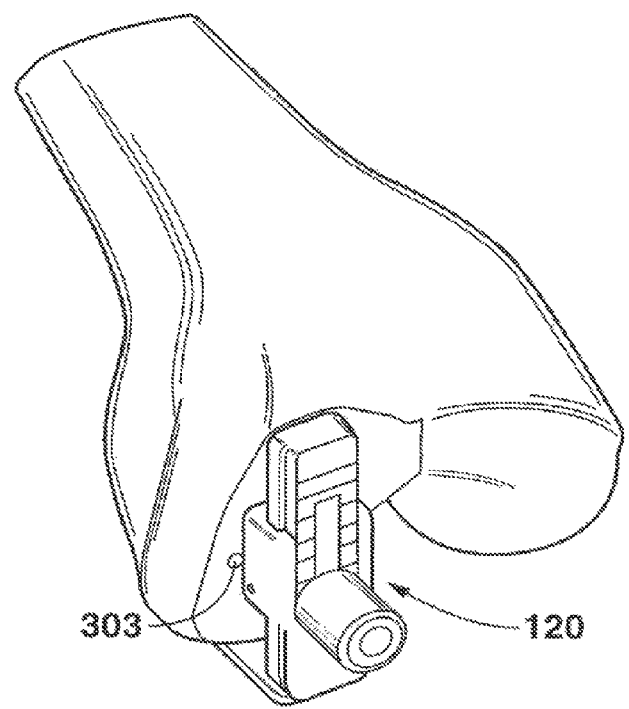
FIG. 4 shows a perspective view of one preferred embodiment of a posterior sizing caliper mounted on the medial distal cut femur with reference to the secondary reference point.

As indicated in FIG. 4, once the secondary reference point 303 has been established on the cut medial distal condyle, sizing is determined using a separate posterior sizing caliper or posterior sizer 120. In order to minimize anterior exposure in a minimally invasive procedure, femoral sizing is preferably carried out using the anterior medial femoral condyle or the anterior medial condyle ridge, rather than the anterior lateral cortex. Sizing can also be carried out using the anterior lateral condyle.

Figure 4P:
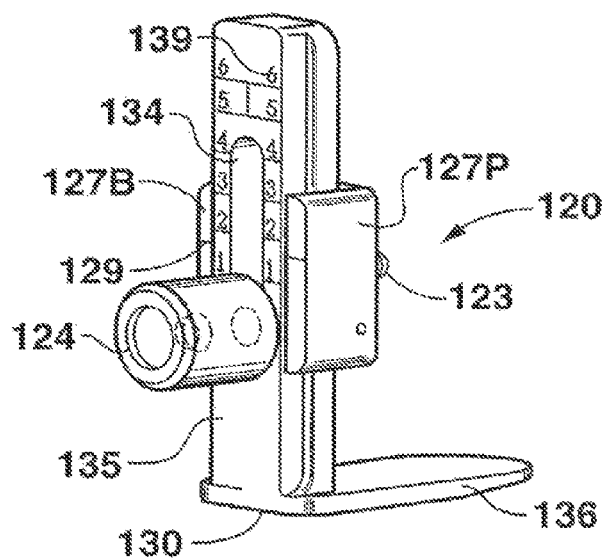
FIG. 4P provides a perspective view of one preferred embodiment of a posterior sizing caliper.

As shown in FIG. 4P, the posterior sizer 120 generally comprises a sizer portion 130 in a sliding relationship with a reference portion 121. As shown in FIG. 4P, a distal surface of the reference portion 121 is provided with pegs or projections 123. The pegs 123 are sized and positioned to match the drill hole or holes 83 of the A-P positioning caliper 80, such that the reference portion 121 is affixed to the cut medial distal femur with reference to the secondary reference point 303 (see FIG. 4). As shown in FIG. 4P, the reference portion 121 is provided with opposing tracks 127A, 127B for slidably engaging a sizer portion 130 of the posterior sizer 120. As shown in FIG. 4P, the sizer portion 130 has a vertical bar portion 135 and at least one posterior paddle portion 136, the bar portion 135 and paddle portion 136 together forming a generally L-shaped configuration. A locking means is preferably provided for use in selectively locking the sizer portion 130 in a selected position on the reference portion 121. In the preferred embodiment shown in FIG. 4P, the locking means is a clamp bolt 124 that is threadably engaged to the reference portion 121. The vertical bar portion 135 is provided with a lengthwise slot 134 to accommodate sliding of the locking means 124.

Calibration marks 139 and reference marks 129 are provided for use in determining the size of the femoral implant.

As shown in FIG. 4P, the calibration marks 139 are on the sizer portion 130 while the reference marks 129 are on the reference portion 121.

As shown in FIG. 4, the peg or pegs 123 of the posterior sizer 120 are inserted into the secondary reference point or points 303 on the medial distal femur. Sizing is achieved by touching the posterior paddle 136 of the posterior sizer 120 to the most prominent portion of the posterior condyle. In a single peg 123 embodiment, the posterior sizer 120 can be rotated about the anterior referencing point to provide optimal sizing.

Alternatively, the peg(s) 123 of the posterior sizer 120 can be inserted into the drill holes 83 of the A-P positioning caliper 80 prior to removal of the caliper 80 from the IM rod 10. The latter technique is particularly suited to making adjustments depending on sizing (e.g. half sizes).

Alternatively, sizing can be accomplished using a combined anterior-posterior positioning and posterior sizing caliper, such as the universal embodiment 140 shown in FIGS. 4B-1 to 4B-4. The combined caliper 140 includes many of the features described above, such as a removable stylus 100 slidably engaged to a stylus holder 101, a reference portion 121 and a sizer portion 130. The combined caliper 140 is preferably provided with a pair of spaced apart posterior paddles 136.

Box Geometry Preparation

Once the proper size of the femoral implant has been determined, an appropriately sized cut block 150 is selected and placed over a single condyle. In the medial approach shown in FIG. 5, the cut block 150 is placed over the medial condyle. As indicated in FIG. 5, although the cut block 150 is mounted only on the medial condyle, the cut block 150 is used to make an anterior cut 354A, a posterior cut 354P, an anterior chamfer cut 355A, and a posterior chamfer cut 355P on both the medial and lateral aspects of the distal femur. After this step, all of the box cuts have been completed with the exception of the distal lateral condyle.

Figure 5P:
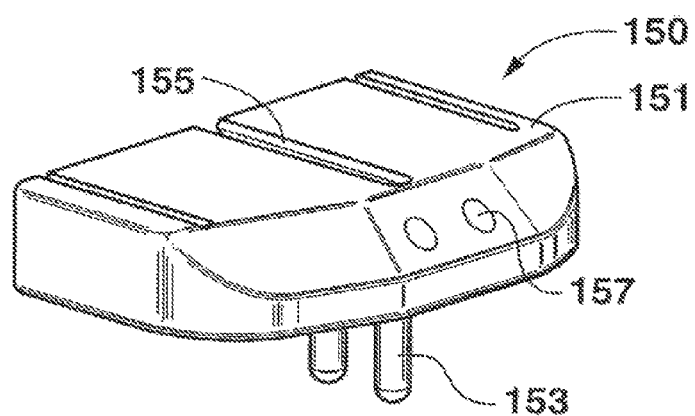
FIG. 5P provides a perspective view of one preferred embodiment of a cut block.
Figure 5:
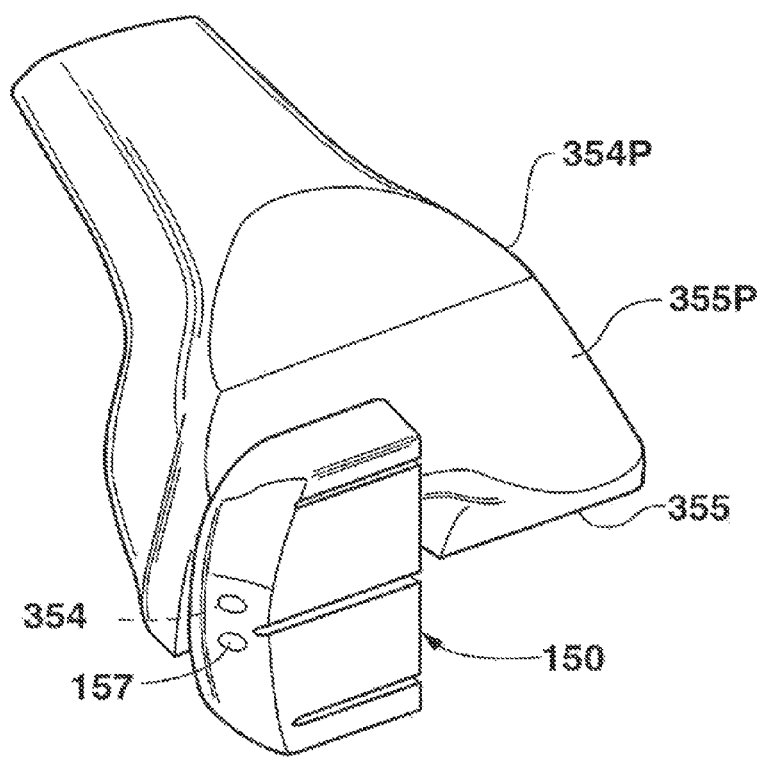
FIG. 5 shows a perspective view of one preferred embodiment of a cut block mounted on the medial distal cut femur with reference to the secondary reference point, and further showing anterior, posterior and chamfer cuts.
Figure 5C:
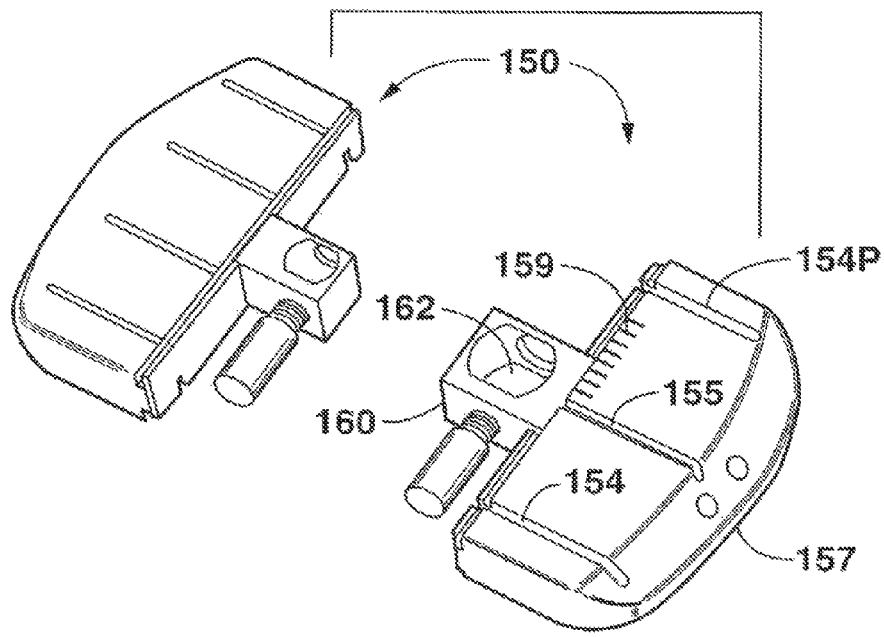
FIG. 5C provides a perspective view of one preferred embodiment of cut blocks having an intramedullary rod aperture and a peg for use in mounting the blocks on the distal femur.
Figure 5D:
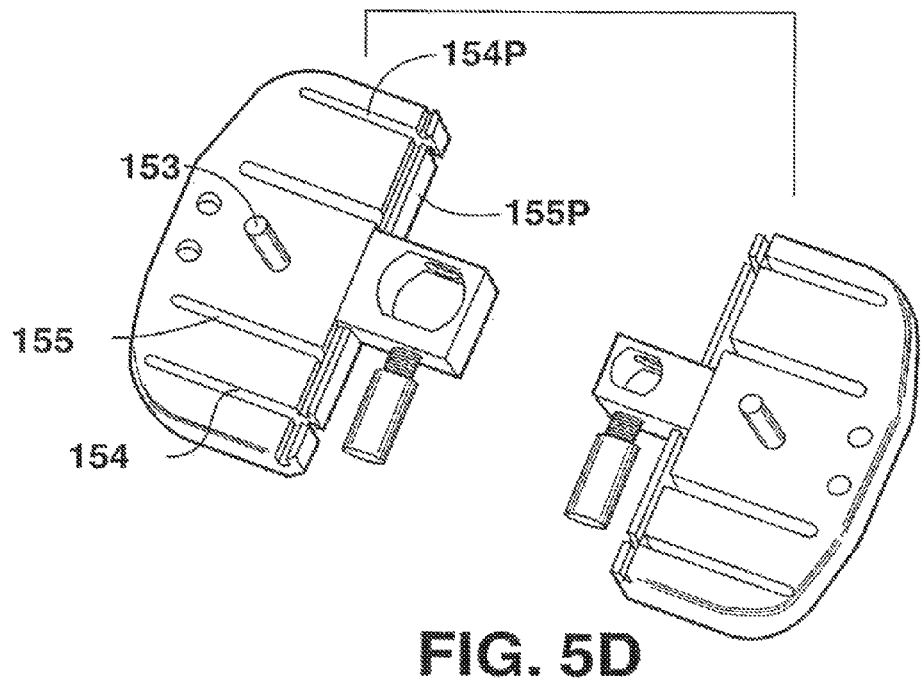
FIG. 5D provides a perspective view of one preferred embodiment of a proximal side of the cut blocks of FIG. 5C.

FIGS. 5C and 5D show left and right versions of preferred embodiments of a cut block 150 that can be attached to the intramedullary rod 10 and to the secondary reference point 303. FIG. 5C shows the distal side of the cut block 150, while FIG. 5D shows the proximal side of the cut block 150. The block portion 151 of the cut block is provided with four slots: an anterior cut slot 154A; a posterior cut slot 154P, an anterior chamfer slot 155A; and a posterior chamfer slot 155P. As viewed from the distal side shown in FIG. 5D, a single entry slot 155 provides common access to both the anterior chamfer slot 155A and the posterior chamfer slot 155P. Each of the slots is open along the patellar groove side of the cut block 150 to allow for resection of the lateral condyle.

As shown in FIG. 5D, a proximal side of the cut block 150 is provided with at least one peg or projection 153 for use in attaching the cut block 150 to the secondary reference point 303 of the distal femur. Fixation apertures 157 are provided for use in temporarily screwing the cut block 150 to the femur in a manner known to those of skill in the art, which stabilizes the cut block 150 during resection. The cut block 150 shown in FIGS. 5C and 5D has an intramedullary rod retaining member 160. The intermedullary rod retaining member 160 includes an IM rod aperture 162 that is sized and configured to closely receive the cut guide mount 14 of the intramedullary rod 10. In the embodiment shown in FIG. 5C, the intramedullary rod retaining member 160 is slidably engaged to the patellar groove side of the cut block 150 for use in selecting an anterior-posterior position. Alternatively, the intramedullary rod retaining member 160 may be fixed to the cut block 150.

As shown in FIG. 5C, a calibration scale is provided on the distal side of the cut block 150. The calibration scale 159 matches the scale of the A-P positioning caliper 80. As indicated in FIGS. 5C and 5D, the cut block 150 is provided in left and right configurations.

FIG. 5P shows a 4-in-1 cut block 150 that uses a particular geometry, rather than an IM rod, to prevent rotation and maintain the established femoral external rotation. The block portion 151 of the two peg cut clock 150 has a configuration and features that are similar or identical to those of the cut block portion 151 of the intramedullary rod cut block shown in FIGS. 5C and 5D. However, the cut block 150 lacks an intramedullary rod retaining portion 160, and instead is provided with two or more pegs 153 on the proximal side. In the preferred embodiment shown in FIG. 5P, the cut block 150 has two pegs 153. Use of a multi-pegged cut block 150 allows box cuts to be made after the intramedullary nail 10 has been removed. The pegs 153 are preferably sized and configured to match the secondary reference points 303 that were created with the drill guide 82 of the A-P positioning caliper 80. Since the intramedullary rod 10 is not available as a reference point, the pegs 153 and holes 303 provide the reference point. Together, the pegs 153 prevent rotational displacement of the cut block 150 relative to the reference points, which allows the surgeon to prepare the box geometry in the correct rotation and orientation. In addition to circular pegs, non-circular geometries can be used to maintain orientation of the cut block 150, including, for example, a slot and fin or an oval hole and oval peg.

In addition to the features described above, the geometry of the cut block 150 is configured to provide for minimized instrument size and for optimizing positioning when using MIS techniques. The cut blocks 150 shown in the drawings include rounded edges along the outer edge, as well as chamfers along the distal side.

Lateral Condyle Resection

After completion of the medial and lateral resections, the cut block 150 is removed. At this point, all of the box geometry cuts have been made with the exception of the distal lateral condyle resection. As shown in FIGS. 6B, 6C, 6D, 6P, 7 and 8, a lateral distal cut guide 170 is used to make the lateral distal condyle resection. As shown in FIGS. 6B, 6C, 6D and 6P, the lateral distal cut guide 170 is placed on the medial distal condyle 351M. As will be explained in further detail below, the lateral condyle cut guide 170 is configured to allow use of the resected bone of the medial distal condyle as the proximal wall or bottom of the distal lateral cut slot 174. This feature minimizes the size of the lateral condyle cut guide 170, which assists in providing a minimally invasive approach.

Figure 6P:
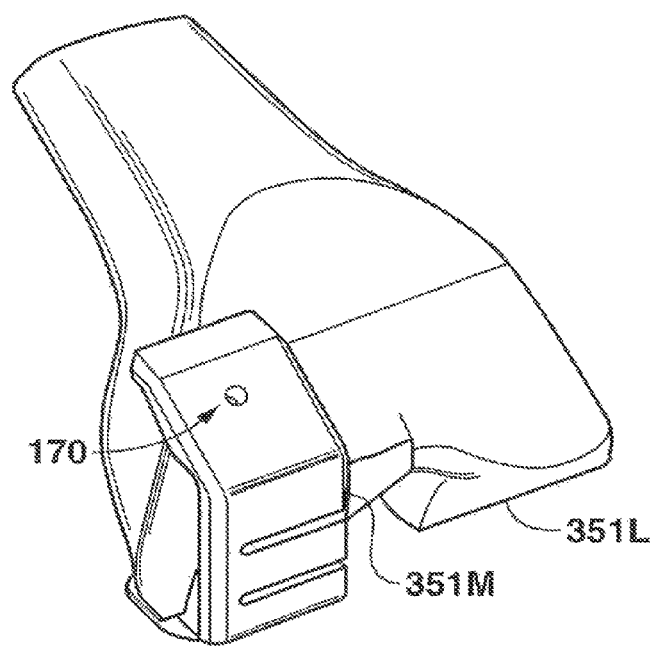
FIG. 6P shows a perspective view of one preferred embodiment of a lateral distal cut guide mounted on the medial distal cut femur for use in resecting the lateral distal femur.
Figure 6B:
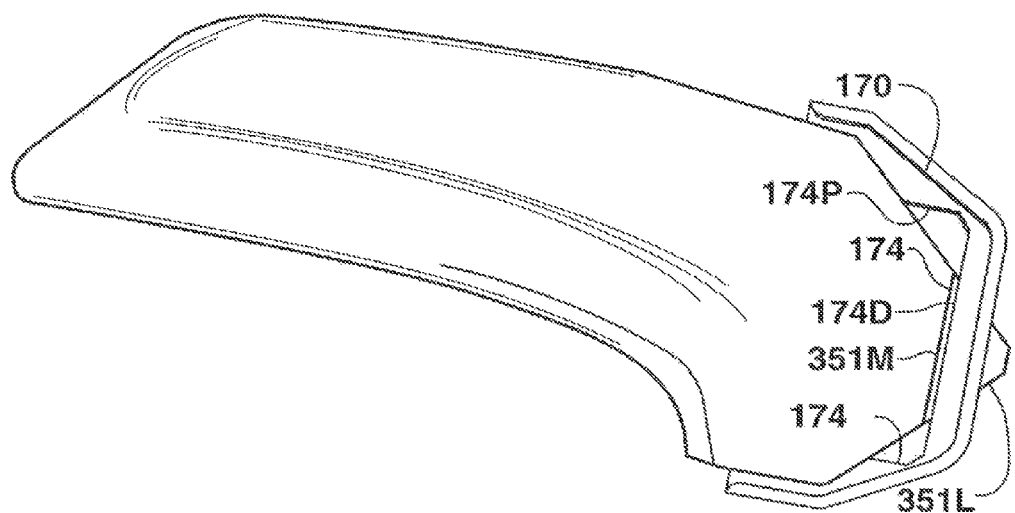
FIG. 6B shows a medial side view of the lateral distal cut guide of FIG. 6A, and further shows a distal lateral cut slot formed between the lateral distal cut guide and the resected surface of the medial distal cut femur.

FIGS. 6B, 6C, 6D, and 6P shows one preferred embodiment of a lateral distal cut guide 170. In FIGS. 6B, 6C, 6D and 6P, the lateral distal cut guide 170 is shown mounted on the medial distal cut femur 351M prior to resection of the lateral condyle 351L. FIG. 6B provides a medial view of the and the lateral distal cut guide 170 mounted on the femur 300. As can be seen in FIG. 6B, the lateral distal cut guide 170 is configured such that a distal lateral cut slot 174 is formed between a distal wall portion 174D of the lateral distal cut guide 170 and the flat surface of the medial distal cut femur 351M (in the drawings, item number "174" is underlined to indicate that the distal lateral cut slot 170 is a space rather than a physical object). Additionally, the lateral distal cut guide 170 is configured to provide an anterior wall portion 174A which forms the anterior limit of the distal lateral cut slot 174, and a posterior wall portion 174P, which forms the posterior limit of the distal lateral cut slot 174. As shown in FIG. 6B, distal portions of the cut guide 170 are configured to closely receive the cut portions of the medial distal cut femur 351M, to thereby assist in securely mounting the cut guide 170 on the distal femur. Additionally, the cut guide 170 is sized and configured to provide a desired width or tolerance to the distal lateral cut slot 174 when the cut guide 170 is mounted on the femur, the desired width being selected to maximize guidance and use of a surgical saw during the distal lateral resection.

Figure 6C:
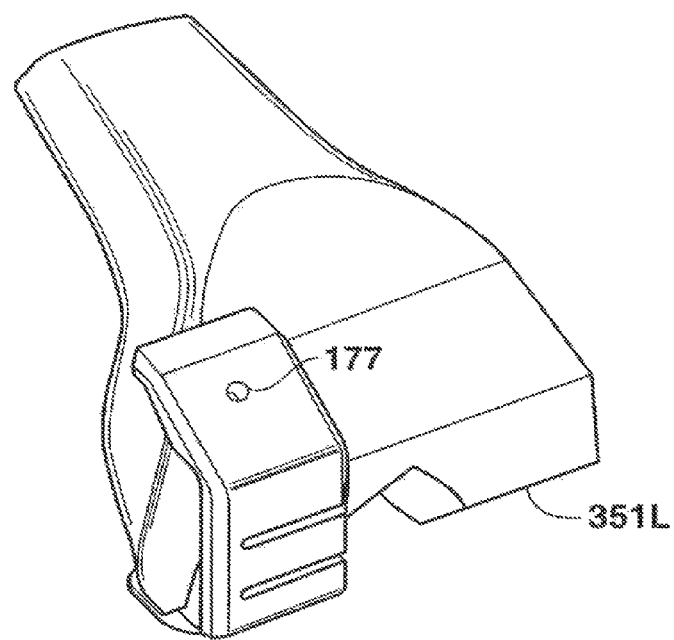
FIG. 6C shows a perspective view of the lateral distal cut guide of FIG. 6A after completion of the resection of the lateral distal femur.

As can be appreciated from the medial view of FIG. 6B, by inserting a saw into the distal lateral cut slot 174 from the medial approach, the surgeon can readily access and resect the lateral distal condyle 351L without inadvertently damaging surrounding tissues. In FIG. 6C, the lateral distal femur has been resected to provide a cut lateral distal femur 351L that is planar or substantially planar with the cut medial distal femur 351M.

Figure 6D:
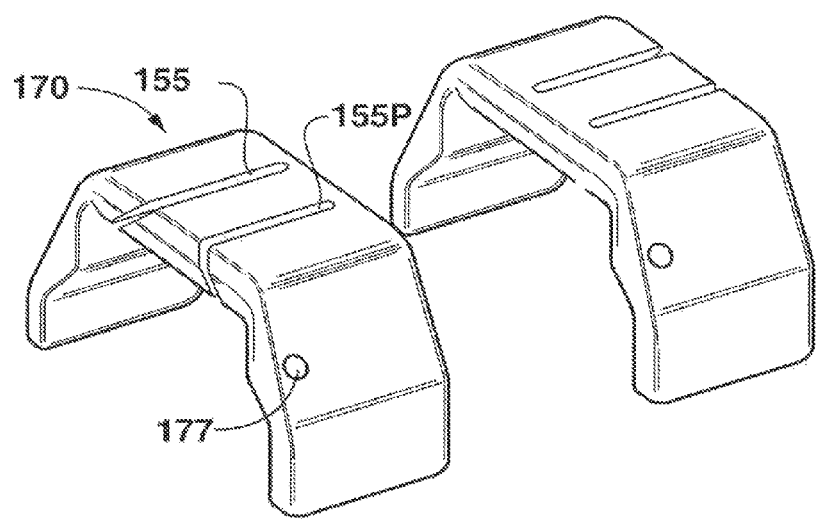
FIG. 6D provides a perspective view of one preferred embodiment of a left and right pair of lateral distal cut guides.

Fixation apertures 177 are provided on the lateral distal cut guide 170 for use in selectively securing the cut guide 170 to the femur with screws. The location of the fixation apertures 177 will vary depending on the size and configuration of the lateral distal cut guide 170, but the locations will preferably be selected to maximize the use of available bone, maximize the structural strength of the lateral distal cut guide 170, and minimize trauma to the patient's bone. As shown in FIG. 6D, the lateral condyle cut guide 170 is available in left and right embodiments. The lateral condyle cut guide 170 is size specific.

As shown in FIGS. 6C and 6D, the lateral distal cut guide 170 can optionally be provided with anterior and posterior chamfer cut slots or guides 155A, 155P, which can be used in lieu of the chamfer cut slots 155A, 155P on the cut block 150. Thus, in the embodiment of FIG. 6C, the lateral distal cut guide 170 can be used to make the chamfer cuts 354A, 354P as well as the lateral distal cut 351L. The chamfer cut slots 155A, 155P open toward the patellar groove in order to provide access to the lateral limits of the femur.

Figure 7:
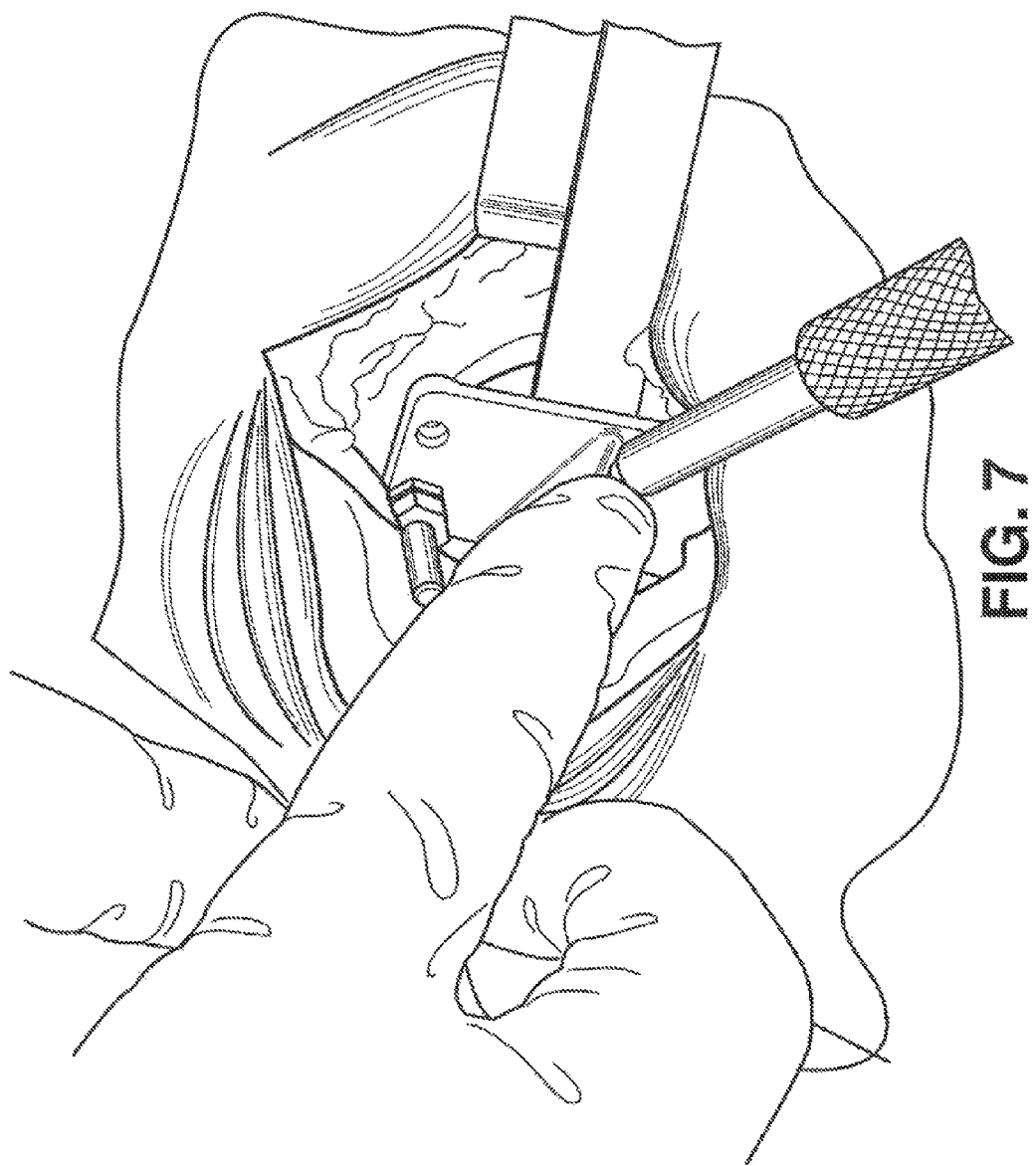
FIG. 7 shows an alternative preferred embodiment of a lateral distal cut guide.
Figure 8:
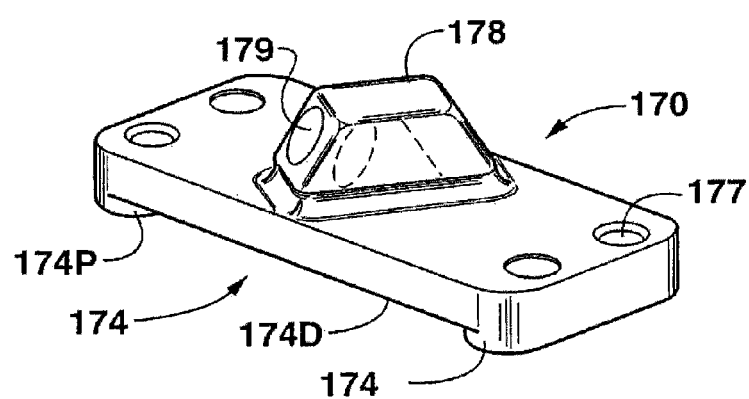
FIG. 8 provides a perspective view of one preferred embodiment of a lateral distal cut guide.

FIG. 7 shows an alternative lateral distal cut guide 170 which presents a smaller profile than that of FIGS. 6B, 6C, 6D, and 6P, thus further contributing to a minimally invasive approach. The embodiment of FIG. 7 forms a distal lateral cut slot 174 between a distal wall 174D and the medial distal cut femur 351M. However, the size of the anterior and posterior walls 174A, 174P of the distal lateral cut slot 174 is minimized in comparison to the embodiment of FIGS. 6B, 6C, 6D, and 6P. In a preferred embodiment, the anterior and posterior walls 174A, 174P are substantially equal to the selected width of the distal lateral cut slot 174, and are configured to rest on the plateau of the medial distal cut femur 351M. As can be seen in FIG. 8, the fixation apertures 177 preferably pass through or adjacent to the anterior and posterior walls 174A, 174P in order to maximize use of available bone for fixation of the instrument.

A handle mount member 178 is fixed or formed on the distal surface of the lateral distal cut guide 170. The handle mount member 178 is provided with a handle engagement means 179 for selectively mounting the lateral distal cut guide 170 on a conventional instrument handle. The handle engagement means 179 can be selected from those available in the prior art, such as threaded, dovetail or quick-connect. As indicated in FIG. 8, the handle mount 178 is oriented to optimize the angle of entry through the incision, which further contributes to the minimally invasive approach.

When using the embodiment of FIG. 7, it may be preferable to complete the lateral distal cut prior to making the box cuts, since more bone will be available for mounting the lateral distal cut guide 170. If used after the box cuts, the anterior-posterior dimension of the lateral distal cut guide 170 of FIG.

8 may be sized substantially to the A-P dimension of the medial distal cut femur 351M, in order to minimize the size of the instrument while providing for maximal use of available bone.

Figure 30:
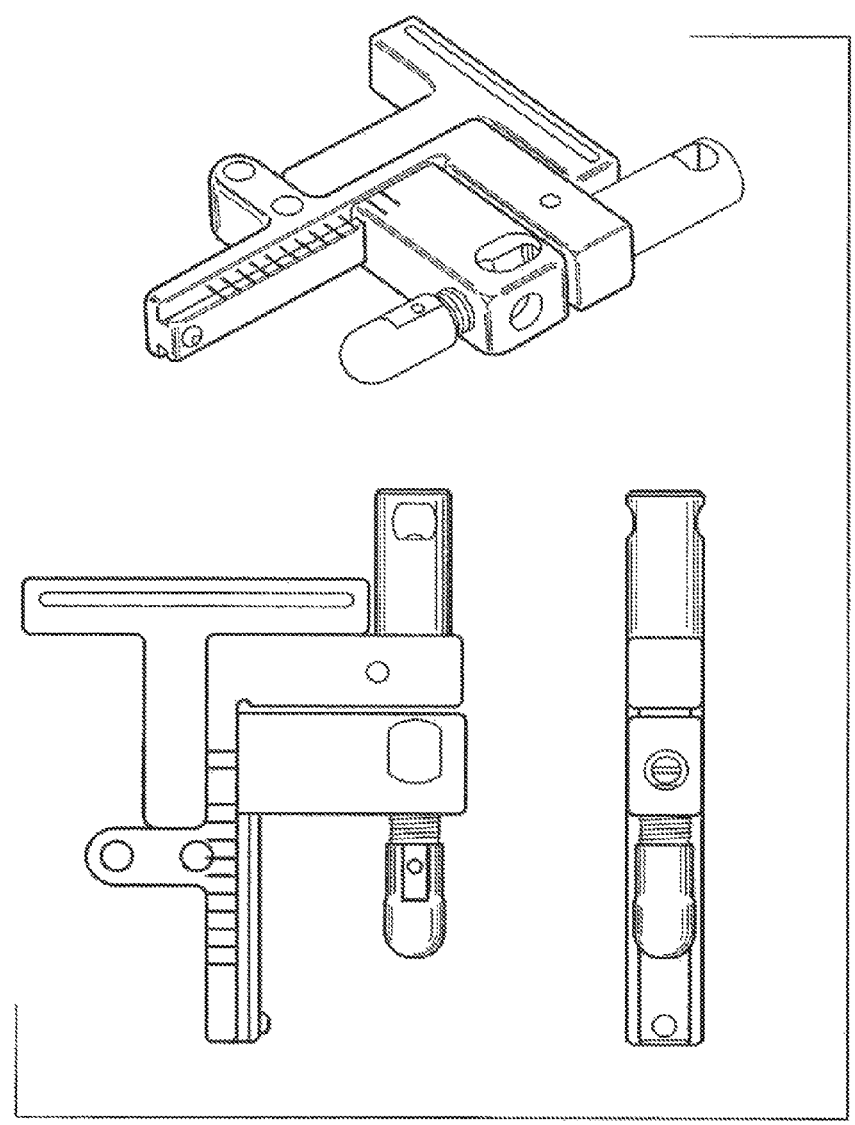
FIG. 30 shows views of a cut guide for use in making an anterior rough cut.
Figures 31, 32:
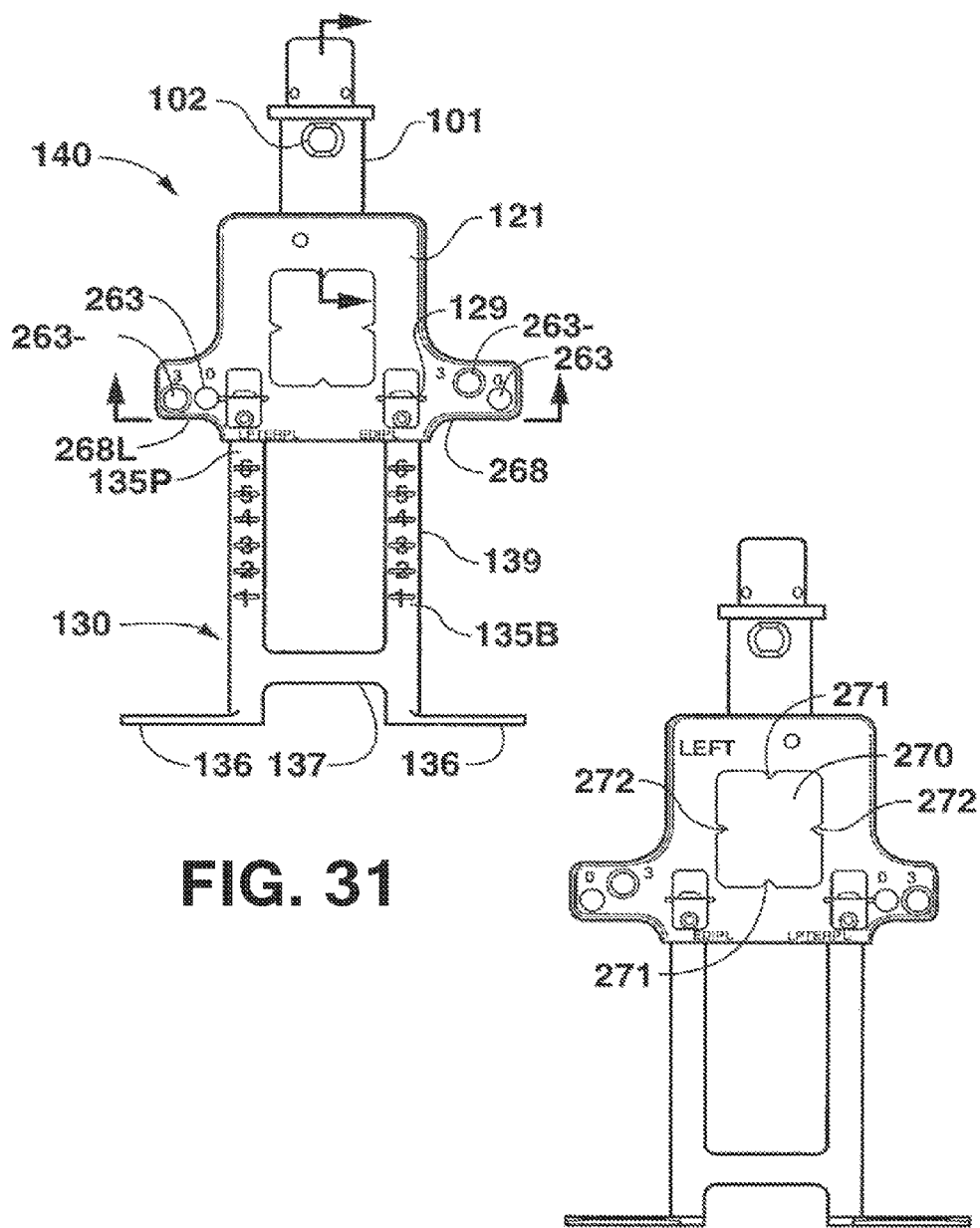
FIG. 31 shows a front elevational view of a universal anterior-posterior positioning and posterior sizing caliper.
FIG. 32 shows a rear view of the universal anterior-posterior positioning and posterior sizing caliper shown FIG. 31.

FIG. 30 shows views of a cut guide for use in making an anterior rough cut. The cut guide has a T configuration with a slot formed through the top of the T. The cut guide is mounted on an A-P positioning caliper such as the caliper shown in FIG. 3P.

Figure 19P:
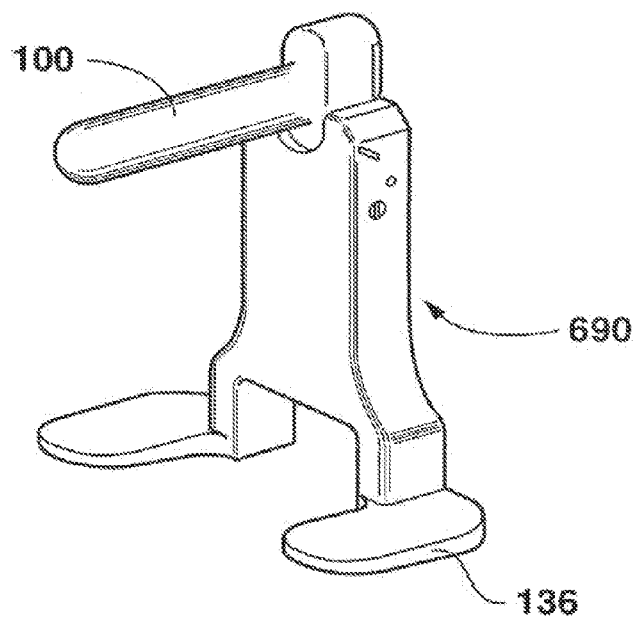
FIGS. 19P and 19B show a preferred configurations of a sizer for use in MIS anterior rough cut procedures.
Figure 19B:
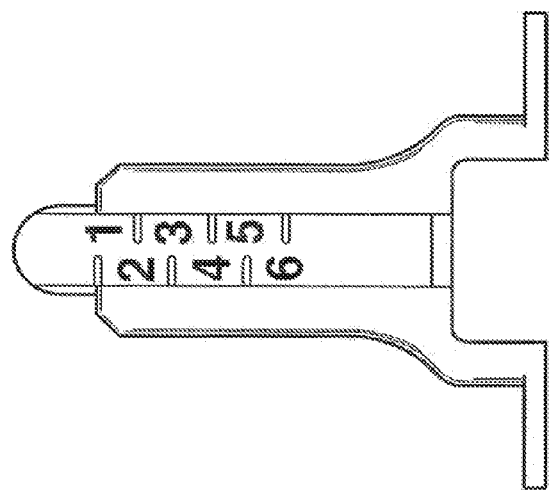
Figure 20P:
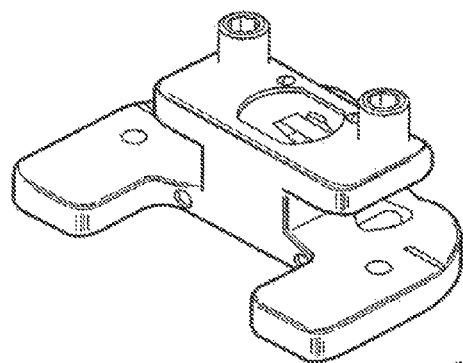
FIGS. 20P, 20B, 20C and 20D show preferred embodiments of a distal IM paddle configured for use in an MIS anterior rough cut procedure.
Figure 20B:
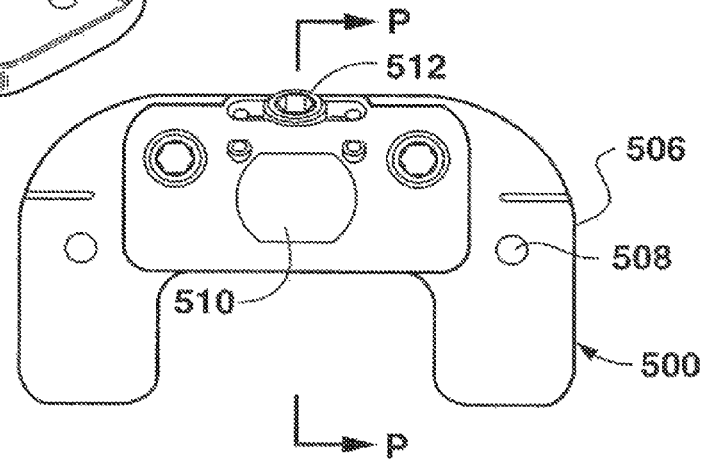
Figure 20C:
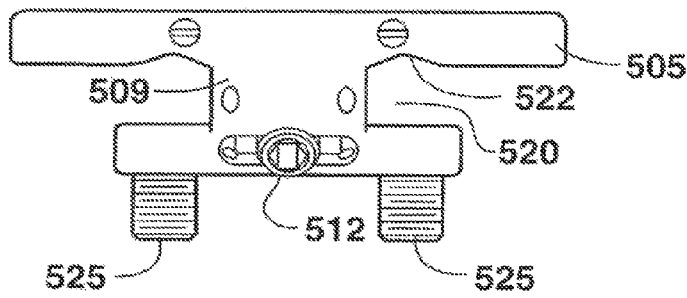
Figure 20D:
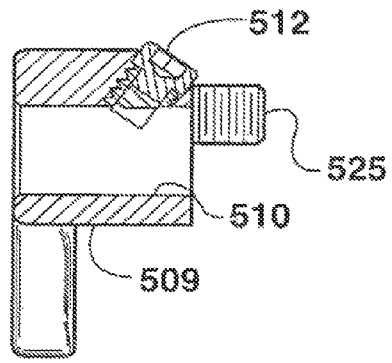
Figure 21P:
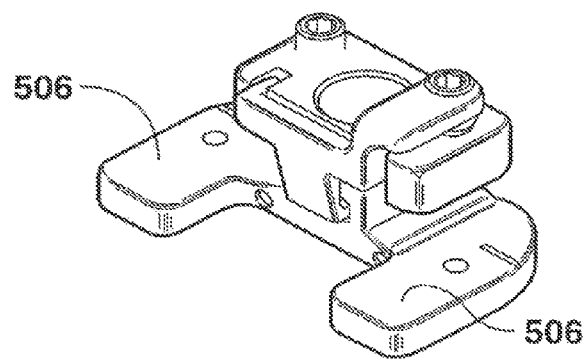
FIGS. 21P, 21B, 21C, 21D, 21E, 21F, and 21G show embodiments of a rotatable distal IM rod paddle which can be rotated about the IM rod and secured into a correct orientation using a self-alignment feature.
Figure 21C:
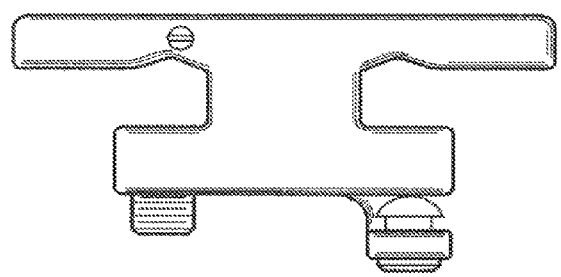
Figure 21B:
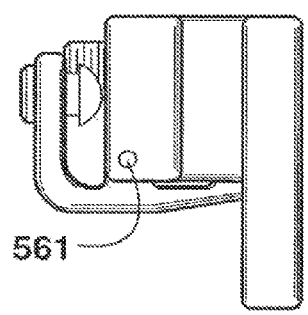
Figure 21D:
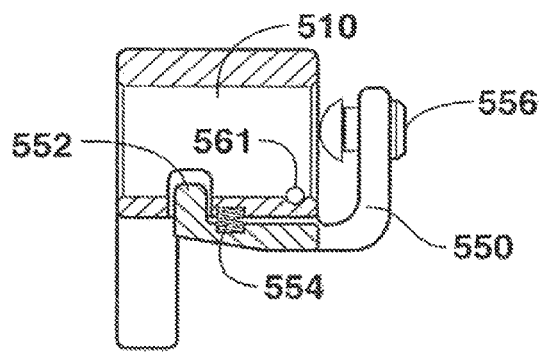
Figure 21E:
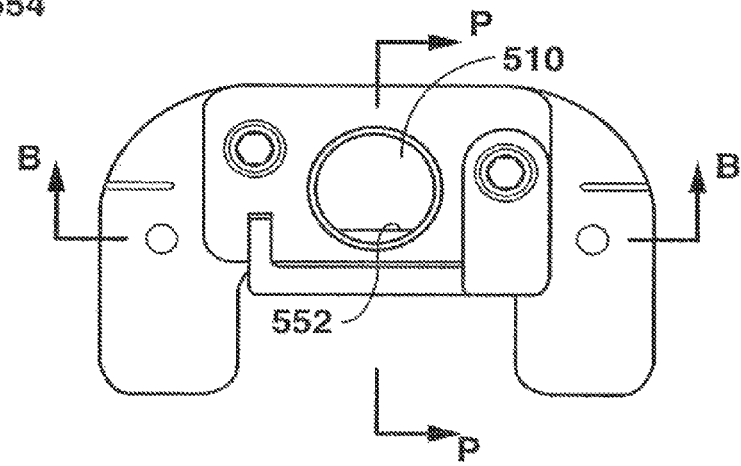
Figure 21F:
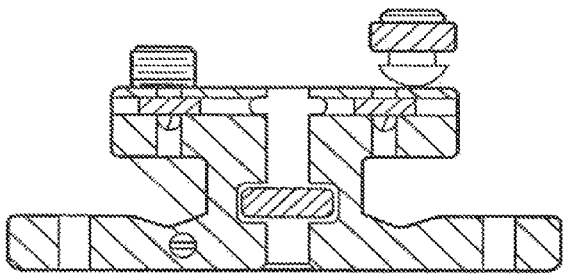
Figure 21G:
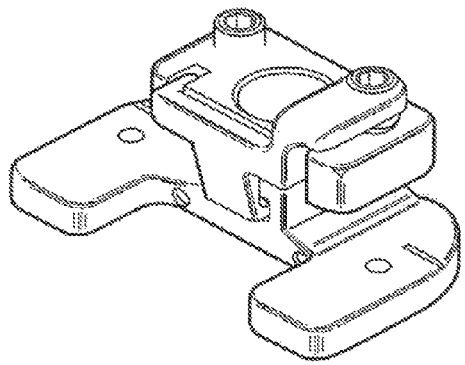

FIGS. 19B and 19P show views of a sizing caliper that is used to size the distal femur after making an anterior rough cut and a distal cut. The lower paddles are configured to rest against the femoral condyles. The upper extension rests on the anterior rough cut.

Variations in the order of the foregoing steps can be made without departing from the spirit and scope of the invention. For example, at the surgeon's discretion, the distal lateral cut may be made prior to the box geometry cuts. Further, some surgeons may find it advantageous to prepare the tibial plateau prior to carrying out the foregoing procedures, in order to provide additional space within the knee cavity for the minimally invasive femoral procedure.

The resections can be limited to just the distal cut or to a combination of distal, anterior, posterior and chamfer cuts. Depending on the cuts performed, this invention will allow the surgeon to size, prepare bone surfaces, etc. in the preferred external femoral rotation. The concepts disclosed herein can be used with different MIS TKA surgical techniques, such as distal cut first, anterior rough cut, etc. The concepts can also be applied to non-MIS TKA instrumentation, as well as other orthopedic applications, including tibial instrumentation.

Although this procedure has been described with reference to a medial approach, the foregoing techniques and instruments can be adapted to a lateral approach. In a lateral approach, the initial cut is made on the lateral distal femur, and the lateral distal cut femur 351L is then used to align and make the anterior, posterior, anterior chamfer, posterior chamfer and medial distal cuts, in the manner described above for the medial approach.

Anterior Rough Cut Procedure

Figure 33:
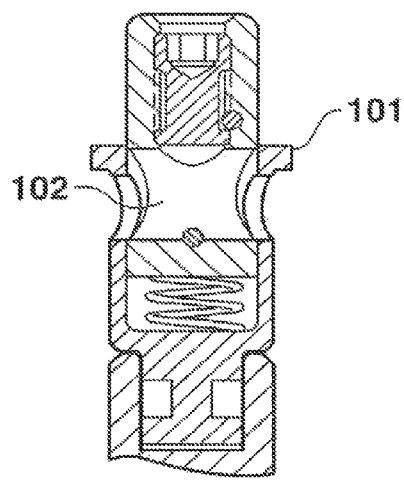
FIG. 33 shows a cross-sectional view of the stylus holder of the universal anterior-posterior positioning and posterior sizing caliper shown FIGS. 31 and 32.
Figure 34:
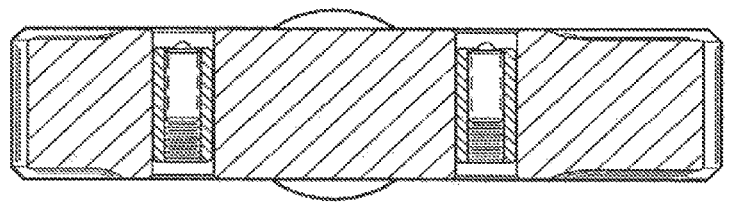
FIG. 34 shows a cross-sectional view of a reference portion of the universal anterior-posterior positioning and posterior sizing caliper shown FIGS. 31 and 32.
Figure 35:
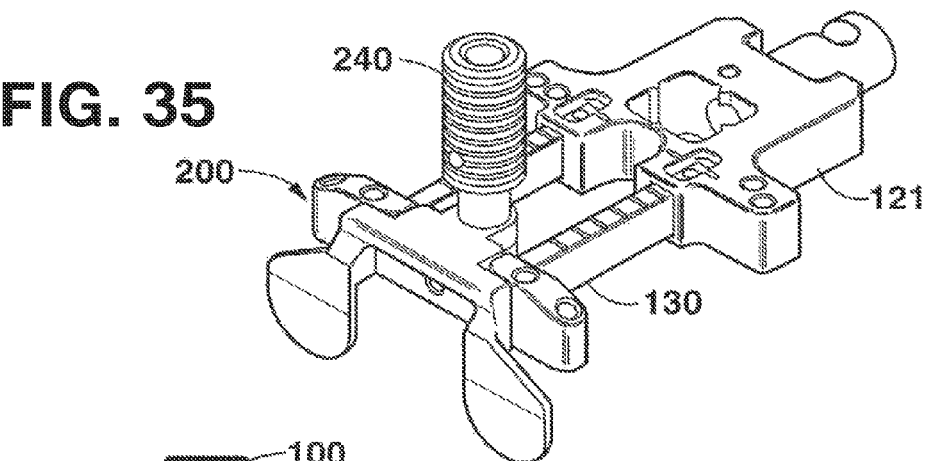
FIG. 35 shows a perspective view of a top loading sizing caliper.
Figure 36:
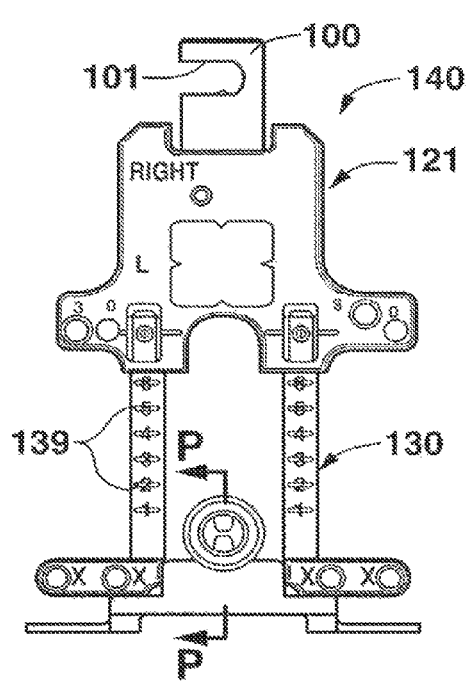
FIG. 36 shows a front elevational view of the top loading sizing caliper of FIG. 35.
Figure 37:
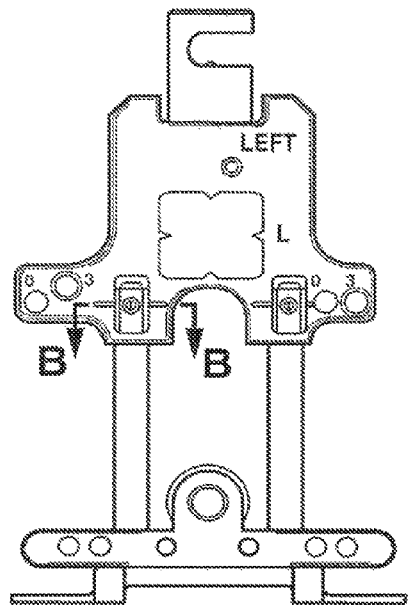
FIG. 37 shows a rear view of a top loading sizing caliper of FIGS. 35 and 36.
Figure 38:
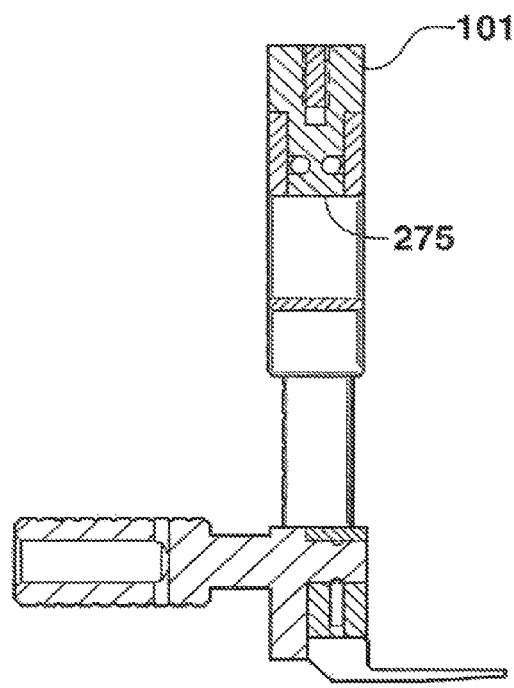
FIG. 38 shows a side view of a top loading sizing caliper.
Figures 39, 40:
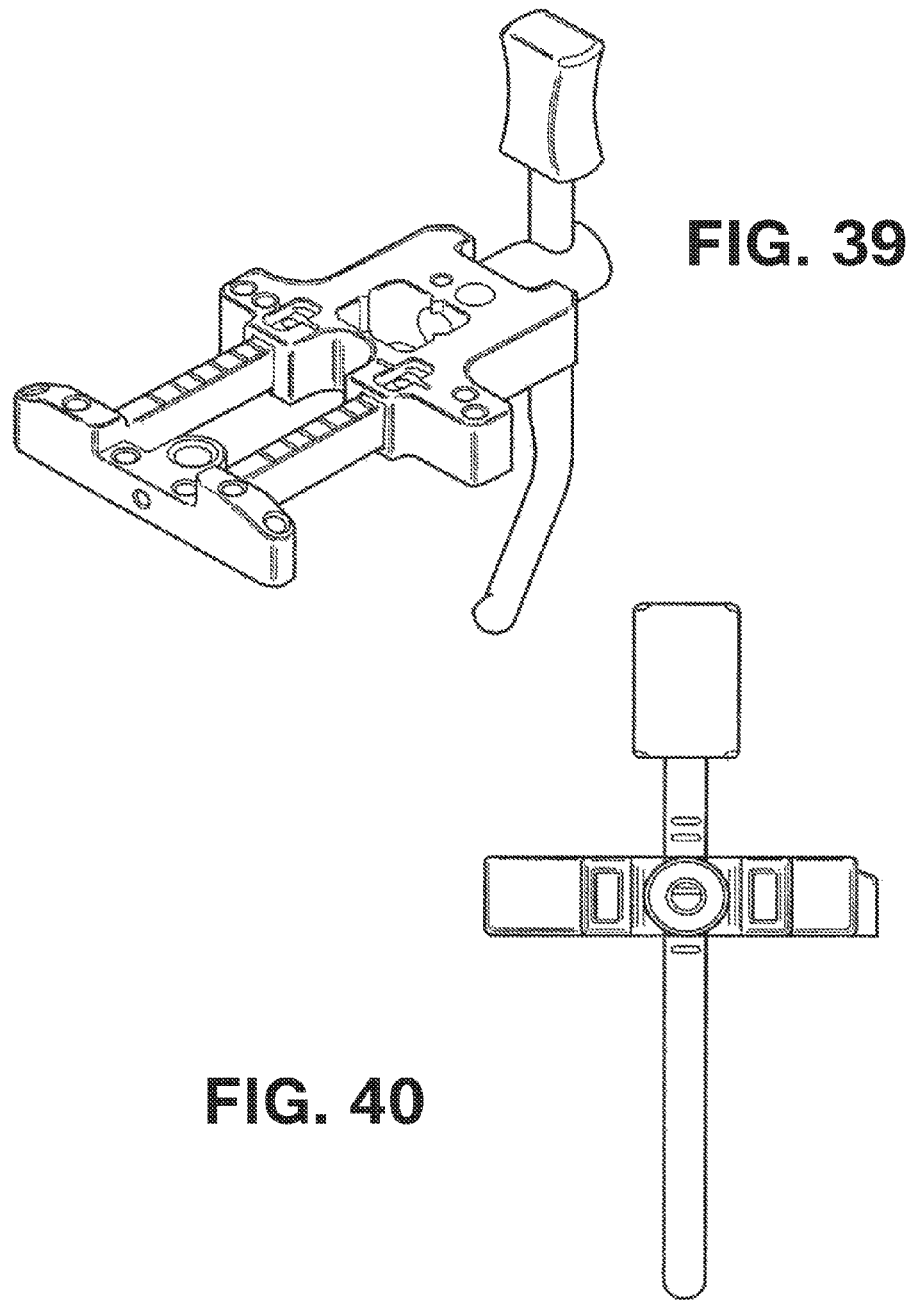
FIG. 39 shows a perspective view of a portion of the top loading sizing caliper of FIGS. 35 and 36.
FIG. 40 shows a top view of a top loading sizing caliper.
Figure 41:
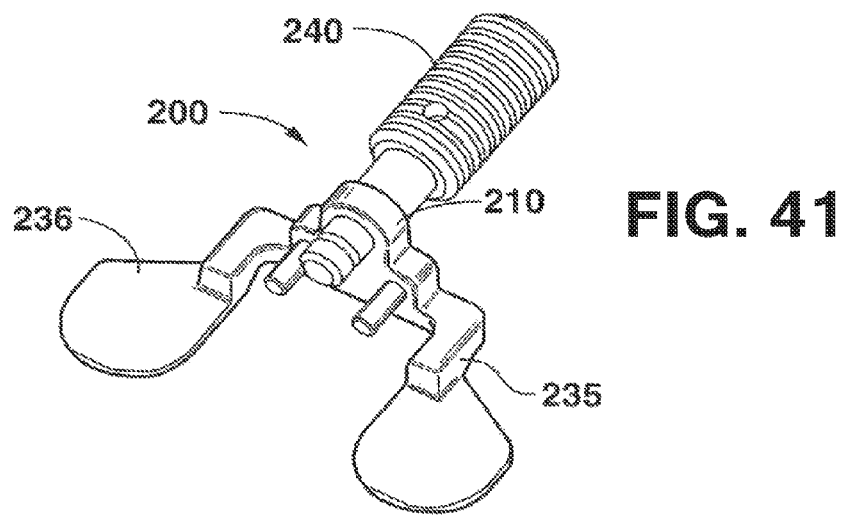
FIG. 41 shows a perspective view of a paddle portion top loading sizing caliper of FIGS. 35 and 36.
Figure 42:
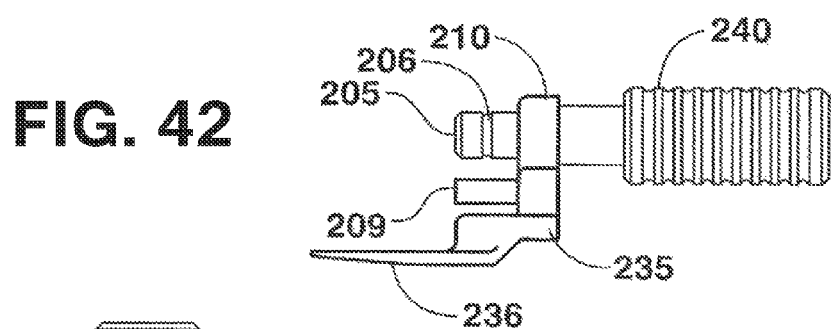
FIG. 42 shows a side view of the paddle portion top loading sizing caliper of FIG. 41.
Figure 43:
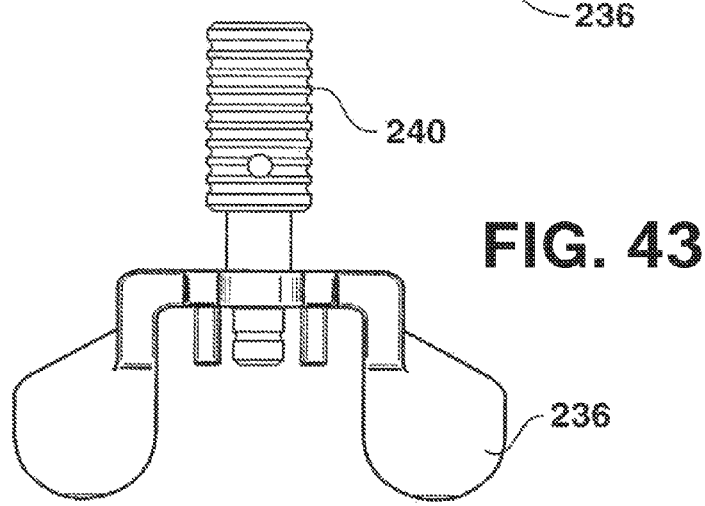
FIG. 43 shows a top view of the paddle portion top loading sizing caliper of FIGS. 41 and 42.
Figure 44:
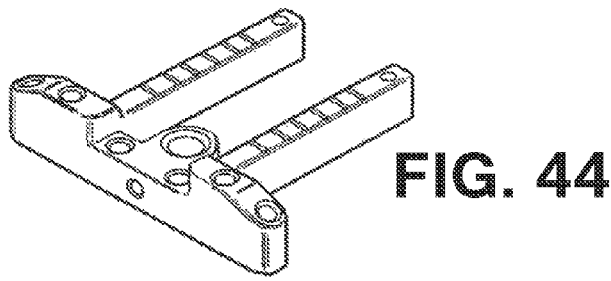
FIG. 44 shows a perspective view of a sizer portion of the paddle portion top loading sizing caliper of FIGS. 35 and 36.
Figure 45:
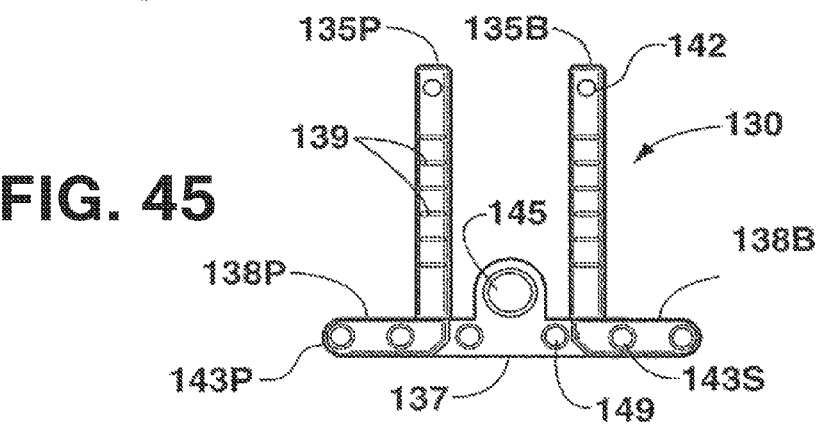
FIG. 45 shows a side view of a sizer portion of the paddle portion top loading sizing caliper of FIGS. 35 and 36.
Figure 46:
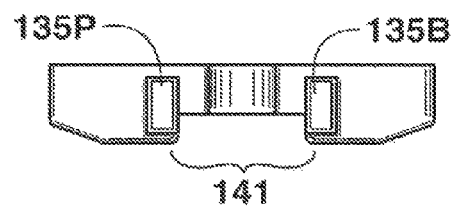
FIG. 46 shows a top view of a sizer portion of the paddle portion top loading sizing caliper of FIGS. 35 and 36.
Figure 47:
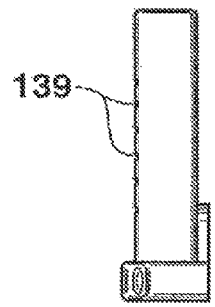
FIG. 47 shows an edge on view of a sizer portion of the paddle portion top loading sizing caliper of FIGS. 35 and 36.

FIGS. 10-18 provides views of the steps used in an anterior rough cut ("ARC") procedure using the ARC instruments disclosed herein. As shown in FIG. 10, the IM rod 10 is installed and properly oriented in the femur 300. Alignment can be achieved using the two handle alignment guide shown in FIGS. 29P and 29B, which is particularly suited for use in MIS knee procedures. As shown in FIG. 10, a distal IM paddle/IM alignment body 500, such as the paddles 500 shown in FIGS. 33, 34 and 35, is slid down the shaft of the valgus portion of the IM rod 10 until it contacts the distal femur. The distal IM paddle 500 is then locked to the flats of the valgus rod 10 by tightening the locking set screw 512. For additional stability, pins may be placed in the pin holes 508 on the distal face of the distal IM paddle 500.

Figure 11P:
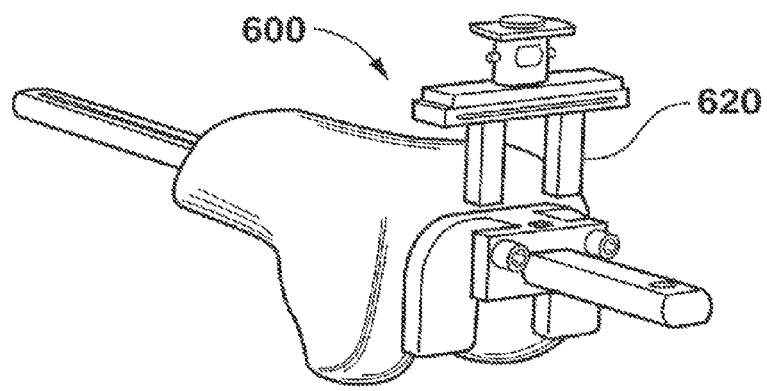
Figure 11B:
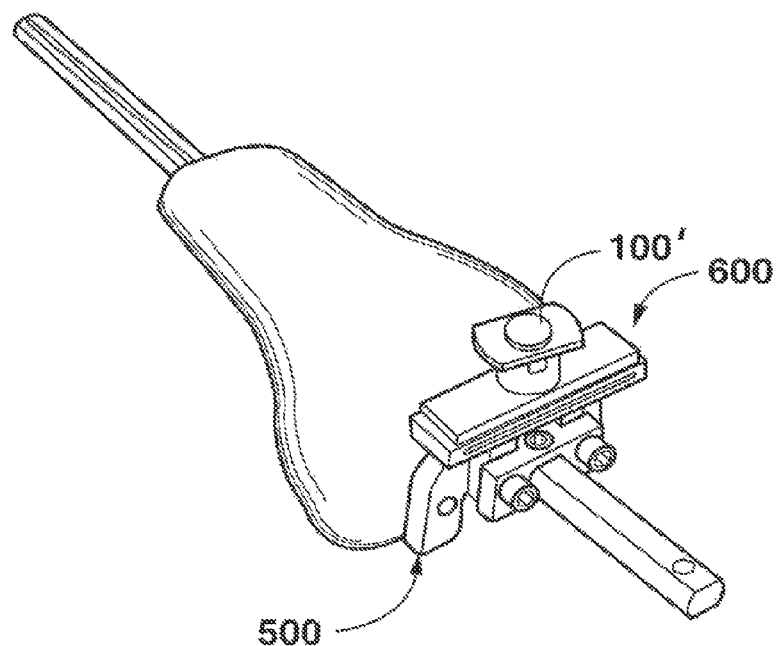
Figure 12:
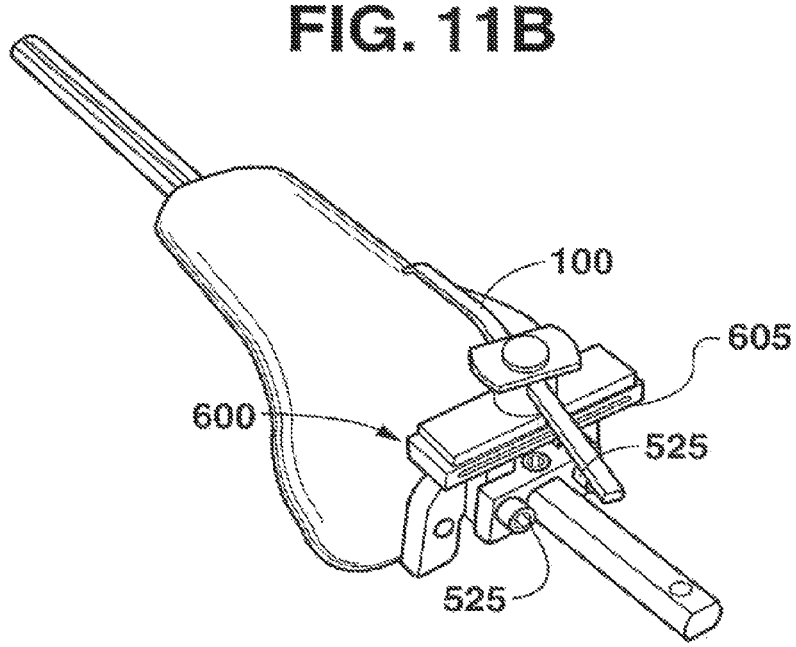
Figure 67:
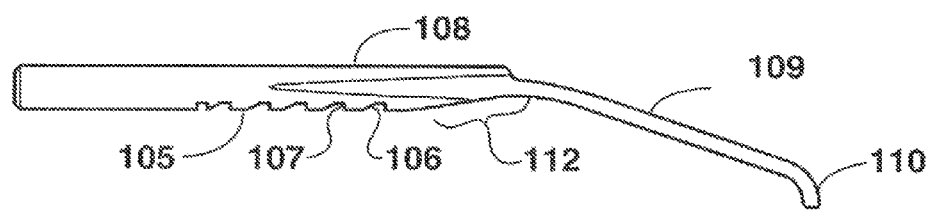
FIG. 67 shows a side view of a stylus configured for use with an anti-backout stylus.

As shown in FIGS. 11P-11B, an anterior rough cut guide 600, such as the type shown in FIG. 67, is slid into the distal IM paddle 500. The support bars 602 of the anterior rough cut guide 600 are slid into the support bar openings 520 of the distal IM paddle 500. As shown in FIG. 12, the tip 100 of an anterior stylus 100 is slid through the stylus bore 102 of the ARC guide 600 for use in sizing the femur.

Figure 68:
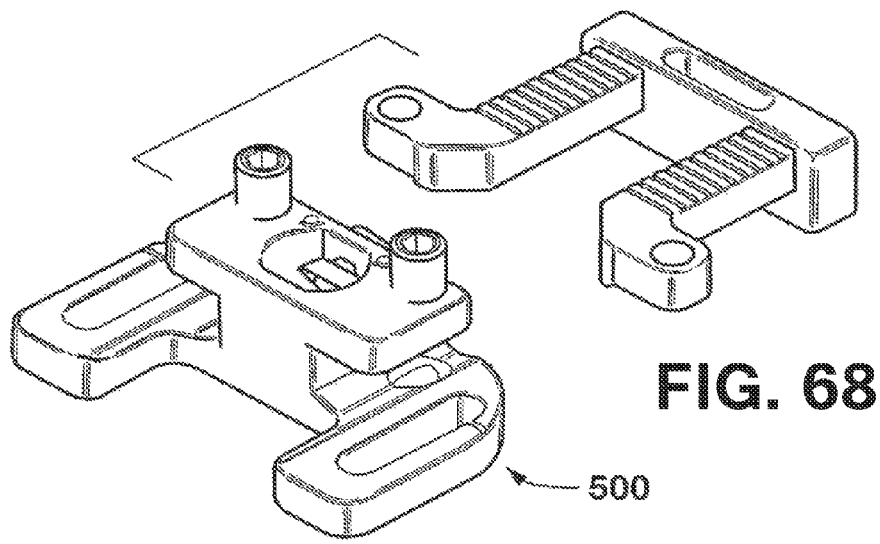
FIG. 68 shows an exploded view of a patella clamp and inseret portion thereof.

In a preferred embodiment, the ARC guide 600 is provided with a locking stylus holder 101' for use with an anti-backout stylus 100'. The anti-backout stylus 100' provides several functions that are useful in MIS procedures. The anti-backout stylus 100' is easy to insert into the stylus bore 102 in MIS incisions, prevents inadvertent backing out of the stylus (which could result in an inaccurate anterior resection), and provides both audio and visual sizing information. As shown in FIG. 67, part of the stylus bore 102 of the locking stylus holder 101' is formed by a biased button 610. The biased button 610 includes a bore 612 for receiving the anti-back out stylus 100'. The bore 612 of the biased button 610 has a stop member 611 on a posterior wall. The biased button 610 is normally biased anteriorly or upwards, such as by a captured spring biasing means 614, such that the stop member 611 normally engages detents 105 formed along a posterior surface of an engagement portion of the anti-backout stylus 100'. As shown in FIG. 68, each of the detents 105 of the anti-backout stylus 101' has an inclined proximal side 106 configured to slide over the stop member 611 when pushed forward, as well as a flat or declined distal side 107 configured to abut against the stop member 611 of the biased button 610. The detents 105 allow the surgeon to slide the stylus 100' forward (proximally), but prevent the surgeon from inadvertently backing out the stylus 100' (distally). However, the surgeon can selectively back out the anti-backout stylus 100' simply by depressing the stylus button 610 while simultaneously pulling the stylus 100' distally. Depressing the biased button 610 disengages the stop member 611 from the detents 105, permitting withdrawal of the stylus 100'. In FIG. 67, the locking stylus holder 101' is shown mounted on an anterior rough cut guide 600, but the anti-backout concepts disclosed herein can be used with other types of styluses or sizing calipers. Additionally, while the anti-backout stylus has been described for use with TKA instruments, an anti-backout stylus could be adapted for use with other orthopedic instruments.

Each of the detents 105 on the anti-backout stylus 101' is preferably positioned to match a particular femoral size, which allows the stylus 101' to provide both visual and audio sizing information. For visual reference, femoral size markings are preferably provided on the anterior portion of the stylus 100, preferably where the stylus meets the stylus holder 101. Additionally, as the stop member 611 snaps into position against a detent 105, the instrument makes a clicking sound. As the surgeon pushes the anti-backout stylus 100' into the stylus bore 102, each click represents one femoral size. The stylus 100 is pushed until the number of clicks equals the estimated femoral size. The clicks provide the surgeon with a non-visual means of verifying the size of the femoral implant, which is useful in MIS procedures.

Other features of the anti-backout stylus 101' that assist in MIS procedures include reduced profiles. When viewed from the side, the anti-backout stylus 101' has a substantially flat portion 108 for sliding through the locking stylus holder 101', a tip 110 on a forward end, and a downwardly sloped portion 109 between the flat portion 108 and the tip 110. To promote ease of insertion when inserting the stylus 101' into an incision, an upwardly sloped cutout 112 is preferably formed along a posterior or lower side of the flat portion 108 in the area adjacent the sloped portion 109 of the stylus 100'. A cutout 112 at this location allows the stylus 100' to slide over anatomical structures encountered in MIS TKA procedures. Additionally, when viewed from the top or bottom, the downwardly sloped portion 109 has a forward taper, i.e. the downwardly sloped portion 109 narrows toward the tip 110. This taper also allows the stylus 100' to slide over or around anatomical structures encountered in MIS TKA procedures.

Once the depth of the anterior resection has been determined using the anterior stylus 100, the anterior rough cut resection slot 605 is fixed into position by tightening the two set screws 525 on the distal face of the distal IM paddle 500. The ARC guide 600 is then removed from the distal IM paddle 500.

Figure 13P:
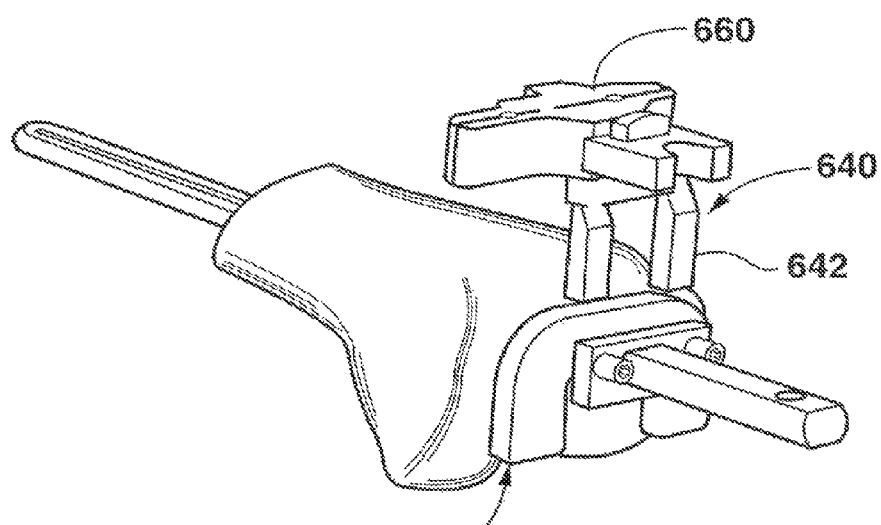
Figure 13B:
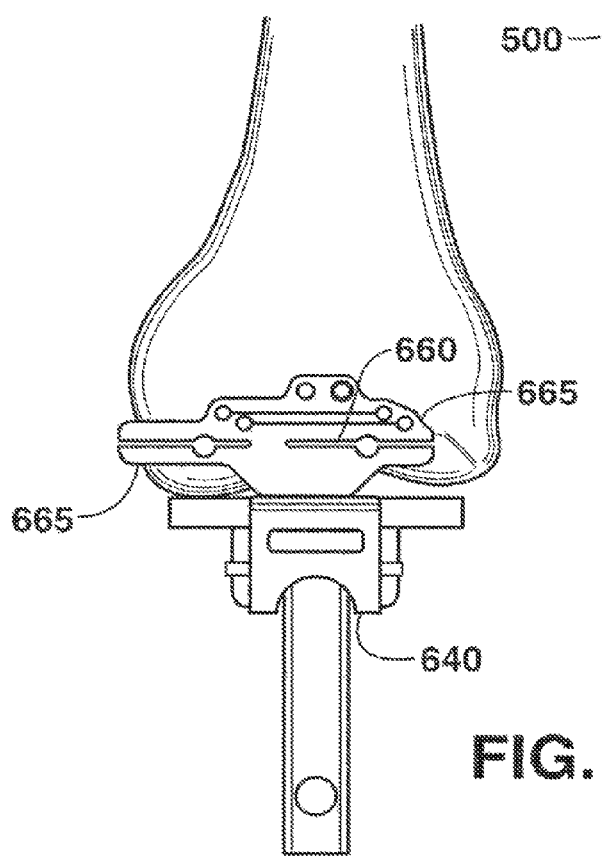
Figure 13C:
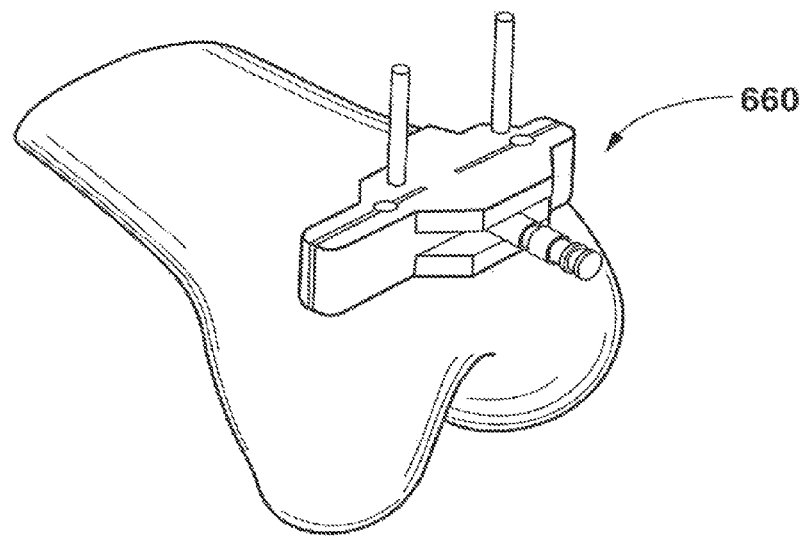
Figure 22P:
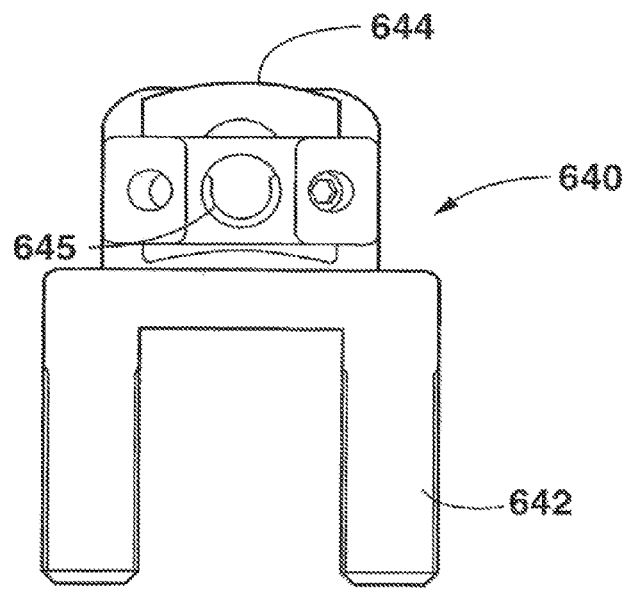
FIGS. 22P and 22B show preferred embodiments of a modular quick connector configured for use in an MIS anterior rough cut procedure.
Figure 22B:
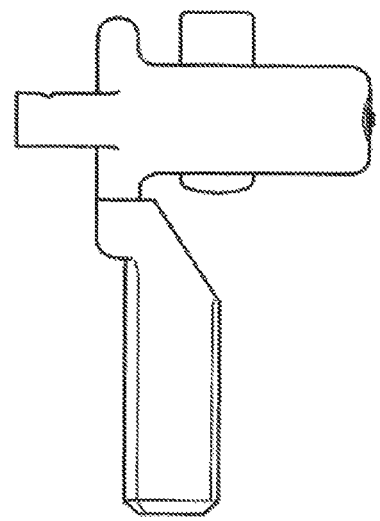
Figure 23:
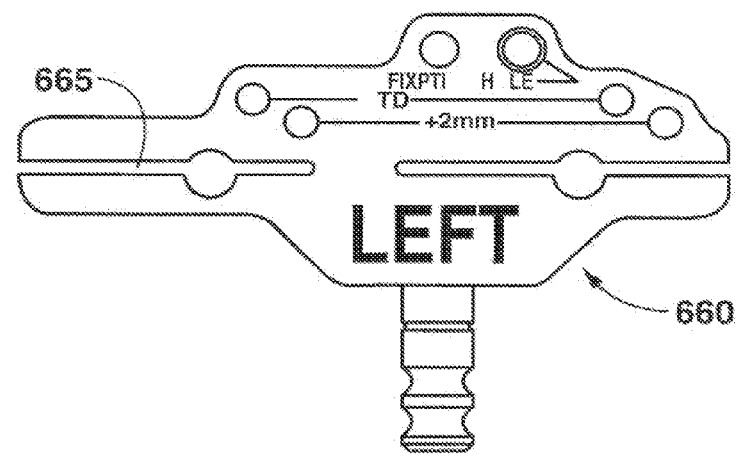
FIG. 23 shows preferred embodiments of a distal cut resection guide configured for use MIS TKA procedures.

As shown in FIGS. 13B, 13C and 13P once the anterior rough cut has been made, a modular quick connector 640, preferably of the type shown in FIGS. 22B and 22P, with an attached distal crosshead 660 is inserted into the distal IM paddle 500. Support bars 642 of the modular quick connector 640 are configured to match the support bar openings 520 of the distal IM paddle 500. The modular connector 640 is configured to receive a distal resection guide 660, such as the distal cut guide shown in FIG. 23, and to hold the guide 660 in a fixed position relative to the distal paddle 500. The modular connector 640 includes a sliding locking button 644. The sliding locking button 644 includes a stop portion 645 configured to selectively engage an annular recess in the mounting stem of the crosshead. In the embodiment shown in FIGS. 22B and 22P, the locking button 644 engages the mounting stem when the button is pushed upward, and disengages when the button is pushed downward. The modular quick connector 640 can be used in ARC or DCF procedures.

As indicated in FIG. 13B, the crosshead 660 is lowered as close as possible to the anterior rough cut. In some cases, the crosshead 660 will not touch the anterior rough cut. In a preferred embodiment, with the crosshead 660 in the standard or primary position, 9 mm of the distal femur will be resected from the prominent distal condyle. If a deeper resection (e.g. 11 mm; 13 mm) is needed, the crosshead 660 may be repositioned for a deeper secondary resection position by pushing the locking button 644 of the modular quick connector 640 down and sliding the crosshead proximally. The location of the secondary position is preferably indicated with a marker (e.g. a "+4 mm" mark becomes visible). The mounting stem of the crosshead 660 includes a second annular recess positioned to engage the stop portion 645 with the crosshead resection slot set at the secondary/deeper resection position. The crosshead 660 is then locked into the secondary resection position by pushing the locking button 644 up.

Figure 14:
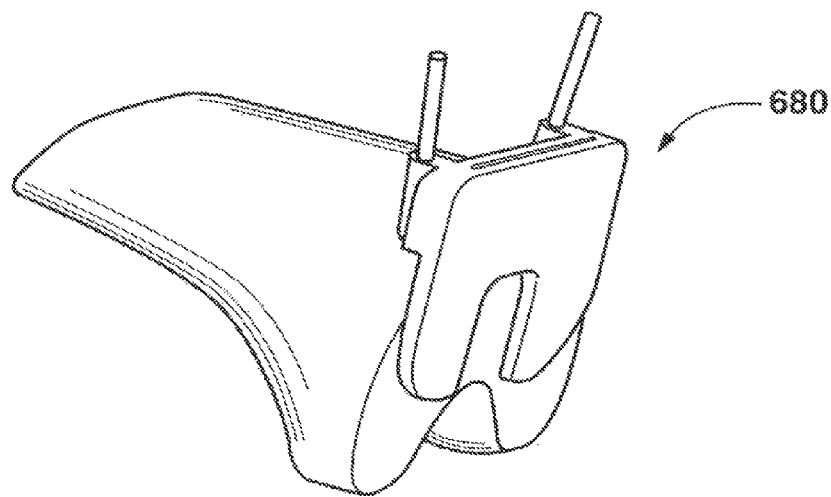
Figure 15:
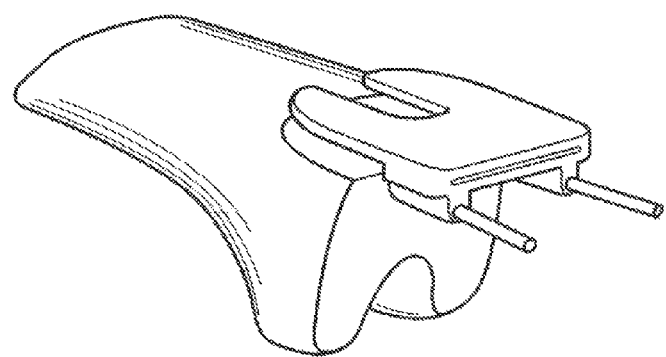

After the resection amount is set, the crosshead 660 is pinned to the anterior cortex of the femur, preferably with two headless pins. Before making the distal resection, the distal IM paddle 500, the modular quick connector 640, and the IM rod 10 are removed from the femur. Pushing down on the locking button 644 unlocks the crosshead 660 from the modular quick connector 640, which allows the remaining components to be removed without dislodging the crosshead 660. With the distal IM paddle 500 and modular quick connector still affixed to the valgus portion of the IM rod 10, a slap hammer and hook can be used to remove the IM rod 10 and attached components from the femur. This leaves the crosshead 660 on the anterior rough cut femur in the configuration shown in FIG. 13C. In a preferred embodiment, the crosshead 660 can be readjusted proximally by lifting the crosshead 660 from the headless pins and then sliding the headless pins through a second set of holes, which are preferably marked to indicate the amount of reset, e.g. "+2 mm." A divergent pin hole is preferably provided in the crosshead 660, and is preferably used to achieve additional stability. A distal resection is then made using the resection slot 665 in the crosshead 660. Once the distal resection has been made, the crosshead 660 is removed from the femur. As shown in FIGS. 14-15, if additional resection is needed, anterior or distal recuts can be made, preferably using the recut guide 680 shown in FIGS. 24B and 24P.

Figure 16:
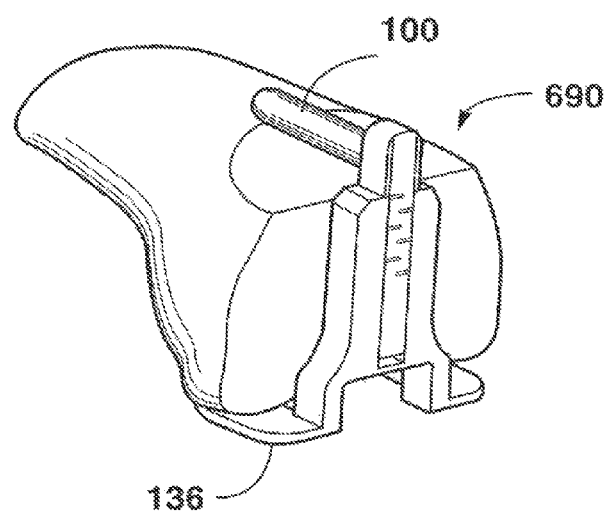

After the anterior rough cut and the distal cut have been made, the surgeon sizes the femur. The A-P sizer 690 shown in FIG. 16 is particularly adapted for sizing an anterior rough cut and distal cut femur in MIS procedures. The small size and rounded edges of the A-P sizer 690 allow it to be maneuvered into position in the confines of an MIS procedure. As indicated in FIG. 16, the A-P femoral sizer 690 is placed flush against the resected distal femur. The A-P sizer 690 is adjusted so that the feet or paddles 136 contact the posterior condyles and the anterior stylus 100 rests on the anterior rough cut. The femoral size is indicated on the distal face of the A-P sizer 690. Resecting the proximal tibia before femoral sizing may facilitate placement of the posterior paddles 136 of the sizer under the posterior femoral condyles.

Figure 17:
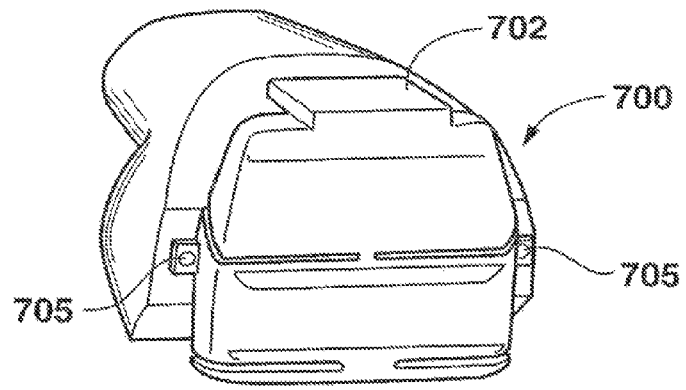
Figure 18:
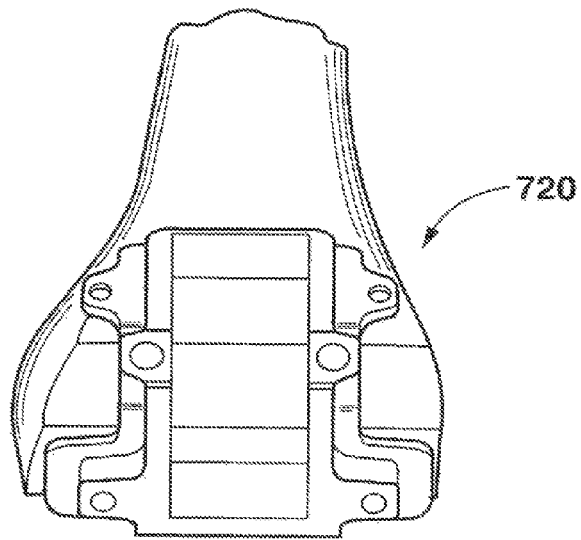

As shown in FIG. 17, after sizing, an appropriately sized ARC femoral resection block 700, preferably of the type shown in FIGS. 25B-D and 25P or FIGS. 26B-D and 26P, is placed flush against the distal and anterior femoral surfaces. The femoral resection block 700 shown in FIG. 17 and FIGS. 25B-D and 25P has several features that make the resection block 700 particularly suited for anterior rough cut MIS procedures. The femoral resection block 700 is universal, i.e. it can be used on either a left or right femur, which reduces instrument inventory. An anterior flange 702 of the femoral resection block 700 is sized and configured to rest against the anterior rough cut when the proximal face of the resection block 700 is flush against the distal rough cut. These features stabilize the femoral resection block 700 when operating in the confined spaces of MIS procedures. Additionally, the femoral resection block features pin outriggers 705 fixed to opposing medial and lateral edges of the block 700 for use in pinning the block 700 to the femur. The through bores of the pin outriggers 705 are preferably offset so as to provide enhanced fixation. The distance between the pin outriggers 705 is substantially the same as the M/L width of the corresponding femoral implant, which allows the resection block to be narrower and thus easier to use in MIS procedures. The narrower size and the pin outriggers 705 allow the surgeon to visualize the bone along the M/L edges of the resection block 700, to verify proper M/L sizing using the pin outriggers 705, and to pin the block 700 to the distal cut femur via the pin outriggers 705. The resection block 700 includes posterior 154P, posterior chamfer 155P, anterior 154A, and anterior chamfer 155A resection slots. The recommended order of resections in the ARC procedure is posterior, posterior chamfer, anterior, and anterior chamfers. Use of unthreaded pins in the pin outriggers 705 is recommended in order to avoid potential pin cross-threading and shearing. A narrow saw blade (12.5 mm) is recommended for the chamfer resections. For added stability, the resection block 700 can also be provided with secondary fixation holes 710 through the face of the block 700. The pins must be removed from the secondary fixation holes 710 prior to the chamfer resections.

The sulcus resection is preferably carried out using a sulcus resection guide 720, such as the sulcus resection guide 720 shown in FIG. 18 and FIGS. 28B-D and 28P. The surgeon selects a sulcus resection guide 720 that corresponds in size to the femoral resection block 700 that was used to make the resections. The sulcus resection guide 720 shown in FIGS. 28B-D and 28P includes cut-out areas 722 along the medial and lateral sides of the sulcus cut guide 720. The outer medial and lateral edges of the sulcus resection guide 720 substantially match the M/L dimension of the femoral implant. The cut out areas 722 allow the surgeon to see the medial and lateral portions of the femur, which allows the surgeon to better visualize placement of the guide 720 as well as the quality of the bone. The top of the sulcus resection guide 720 rests on the resected anterior femoral cortex. The sulcus resection guide 720 is preferably lateralized on the femur to reacquire the Q-angle. The sulcus resection guide 720 is pinned to the femur using the anterior and distal pairs of holes. The trochlear groove is resected using a saw blade on either the anterior or posterior angled surface and along the sides 726 of the central opening 725 of the sulcus resection guide 720.

FIGS. 27B-D and 27P show a femoral trial sulcus resection guide 720 that can be used both as a femoral trial and to make a sulcus cut. The trial sulcus resection guide 720 features a removable patella groove portion 727, which slides into the opening 725 in the body of the trial. The removable patella groove 727 can be used to check patella fit, and can also be removed from the trial body 720 in order to provide access for the sulcus cut. A removable cut guide 730 can be mounted into holes on the face of the implant for use in supporting a saw blade when making a sulcus cut. The cut guide 730 can be provided with a resection slot (not shown) or a support bar 731. Once the sulcus cuts are complete, the surgeon trials and implants in the conventional manner.

Aspects of preferred embodiments of instruments used in the anterior rough cut procedure will now be described in further detail.

FIGS. 20B-D and 20P show an alternative embodiment of a distal IM rod paddle 500 for mounting on an IM rod 10 for use in making anterior and distal cuts. FIG. 10 shows the distal paddle 500 on an IM rod. Each of the support bar openings 520 are preferably provided with a grooved portion 522, which is sized and configured to closely receive a matching ridge 622 of the support bars 620 of modular inserts, such as of the anterior rough cut guide 600, the insert portion 580, or the modular quick connector 640.

FIGS. 21B-G and 21P show an embodiment of a rotatable distal IM rod paddle 500 which can be rotated about the IM rod 10 and secured into a correct orientation using a self-alignment feature. The rotatable IM rod paddle 500 is particularly suited to MIS procedures because it allows the surgeon to insert the paddle 500 onto the IM rod 10 in any degree of rotation, rotate the paddle 500 on the IM rod 10 until a correct orientation is achieved, and then secure the paddle 500 on the rod 10 in the correct orientation. Prior art paddles 500 were non-rotatable, and therefore had to be placed on the IM rod 10 in the correct orientation, which can be difficult when operating under the confines encountered in MIS procedures. Prior art non-rotatable paddles tend to abut against tissues within the incision, which makes it difficult to achieve the orientation needed for slipping the paddle onto the rod. With a rotatable paddle 500, the surgeon can simply rotate the paddle within the incision until the IM rod aperture 510 passes over the end of the valgus portion of the IM rod 10, without regard to the orientation of the paddle 500. This allows the surgeon to maneuver the rotatable paddle 500 onto the rod 10 while avoiding contact between tissues and protruding parts of the paddle 500, such as the paddle legs 506.

Rotation is achieved by providing the paddle 500 with an IM rod aperture 510 that is configured to allow the paddle 500 to rotate on the IM rod 10. The IM rod aperture 510 preferably has a round or cylindrical configuration, which permits 360 degree rotation on the rod 10. The circumference of the IM rod aperture 510 is preferably selected to closely fit the opposing rounded sections of the applicable IM rod 10, such that lengthwise contact between the rounded sections of the IM rod 10 and the round aperture 510 of the rotatable paddle 500 serves to substantially prevent rotation of the paddle 500 on the rod 10, except about the axis of the valgus portion of the IM rod 10.

Additionally, the rotatable IM paddle 500 is provided with a means 550 for selectively securing the paddle 500 in the correct orientation, i.e. for selectively preventing rotation of the rotatable paddle 500 about the axis of the valgus portion of the IM rod 10. The securing means 550 is preferably self-aligning, such that the surgeon does not have to be concerned with placing the rotatable paddle 500 in the correct orientation prior to securing the paddle 500 in place. In the embodiment shown in FIGS. 21B-G and 21P, the locking means includes a generally L-shaped locking member 550. A proximal end of the locking member 550 is provided with an upwardly extending stop member 552. The locking member 550 is configured to selectively lodge the stop member 552 in the IM rod aperture 510. The locking member 550 is pivotally mounted to the paddle 500, such as via a cross-pin 561. The locking member 550 is preferably normally biased into an open position, such as by a captured spring 554. Turning down a buttress screw 556 forces the locking member 550 to pivot the stop member 552 into the IM rod aperture 510 and into contact with a posterior side of the IM rod 10. The stop member 552 abuts against a flat portion of the IM rod 10, which serves to selectively lock the rotatable paddle 500 in a non-rotational relationship with the IM rod 10. The stop member 552 also prevents translation or sliding of the rotatable distal IM paddle 500 along the valgus portion of the IM rod 10. When the surgeon is finished using the distal IM paddle 500, the paddle 500 is removed simply by reversing the buttress screw, which allows the stop member 550 to pivot out of the IM rod aperture 510.

Figure 24P:
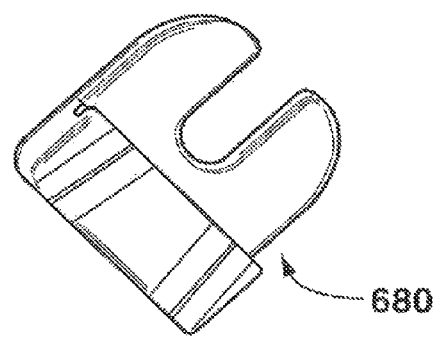
FIGS. 24P, 24C, and 24B show preferred embodiments of a recut guide configured for use in MIS TKA procedures.
Figure 24C:
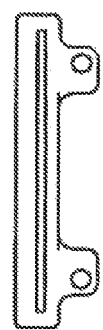
Figure 24B:
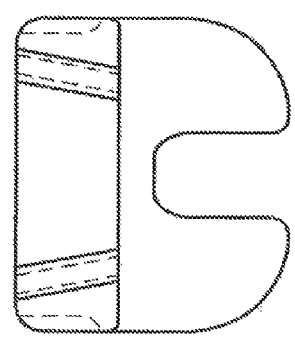
Figure 25P:
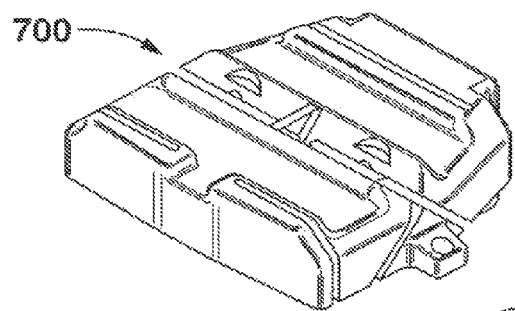
FIGS. 25P, 25B, 25C and 25D show preferred embodiments of an anterior rough cut femoral resection block.
Figure 25B:
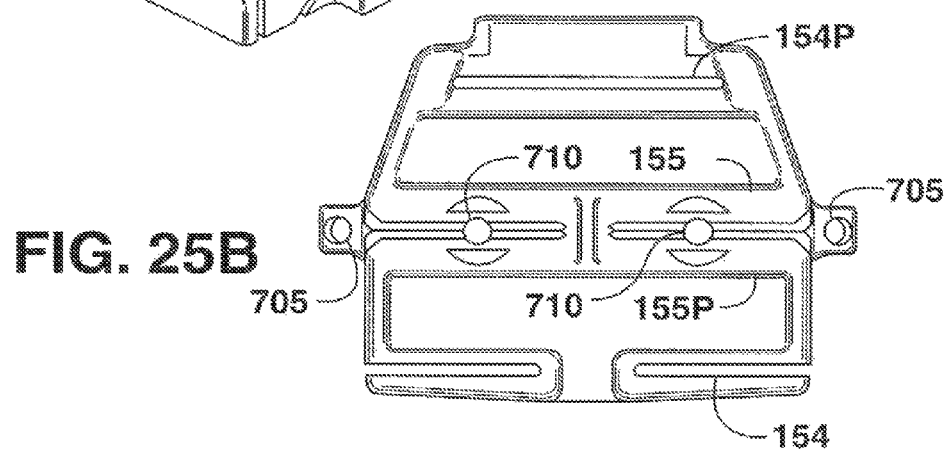
Figure 25C:
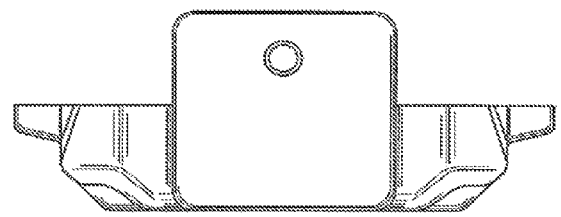
Figure 25:
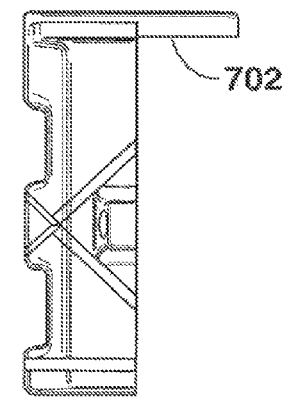
Figure 26P:
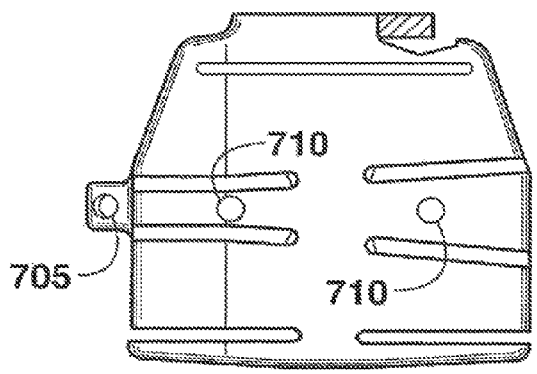
FIGS. 26P, 26B, 26C, and 26D show preferred embodiments of an anterior rough cut femoral resection block having a medialized configuration.
Figure 26B:
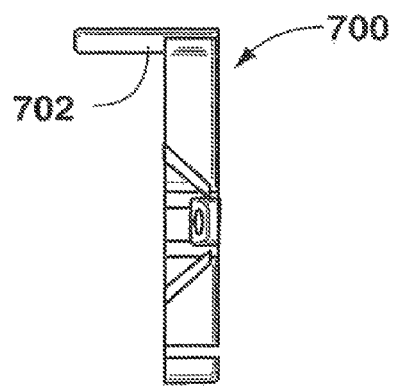
Figure 26C:
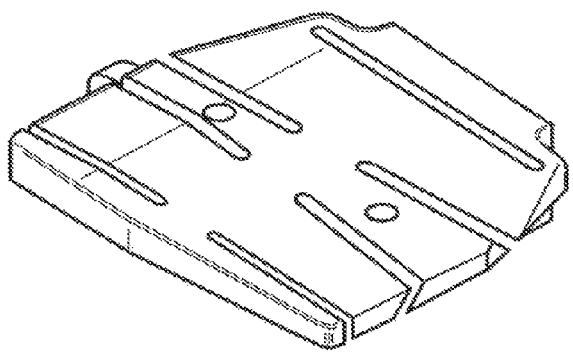
Figure 26D:
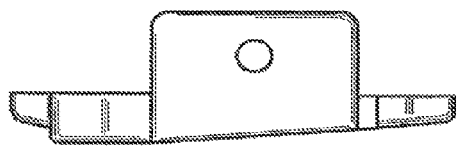
Figure 27P:
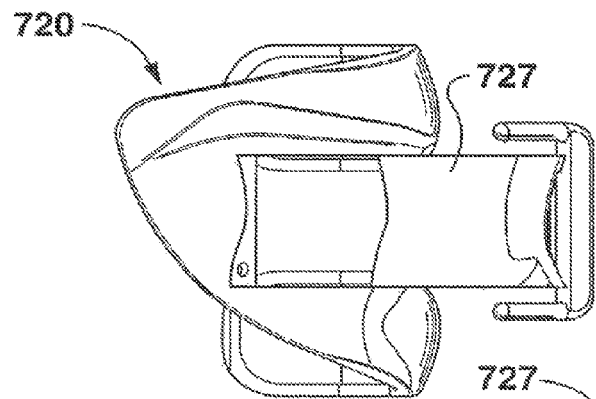
FIGS. 27P, 27B, 27C, and 27D show preferred embodiments of a trial sulcus resection guide configured for use in MIS TKA procedures.
Figure 27B:
Figure 27C:
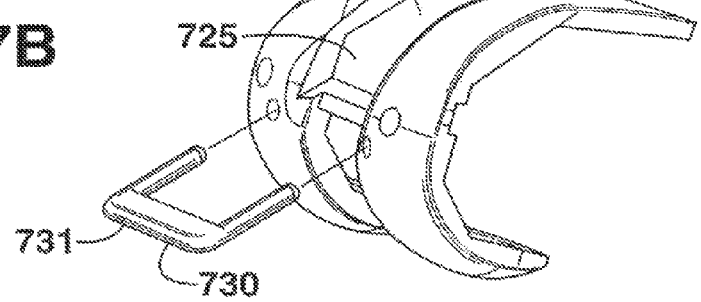
Figure 27C:
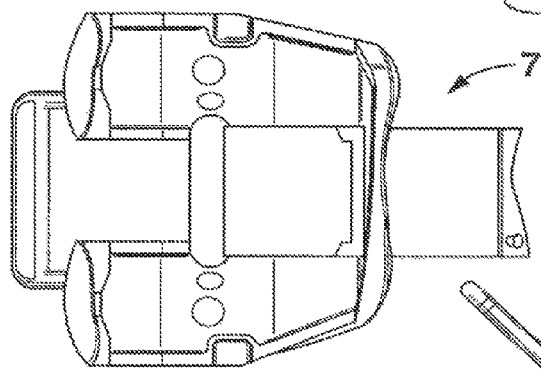
Figure 27D:
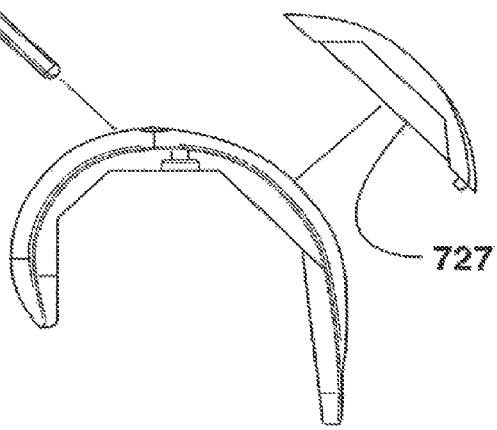
Figure 28P:
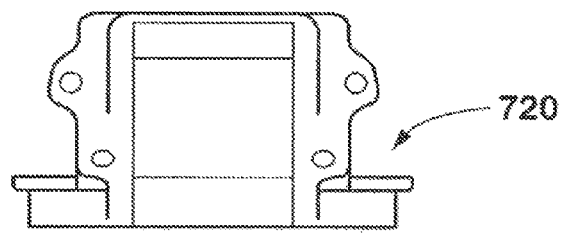
FIGS. 28P, 28B, 28C, and 28D show preferred embodiments of a sulcus resection guide configured for use in MIS TKA procedures.
Figure 28B:
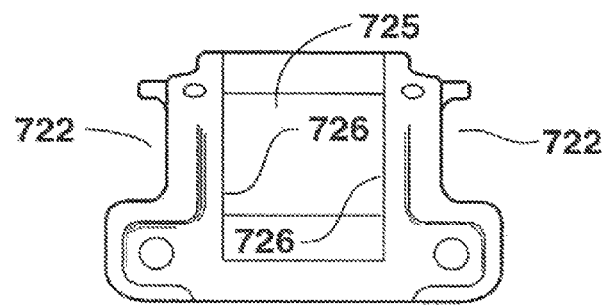
Figure 28C:
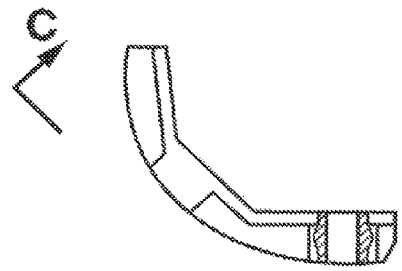
Figure 28D:
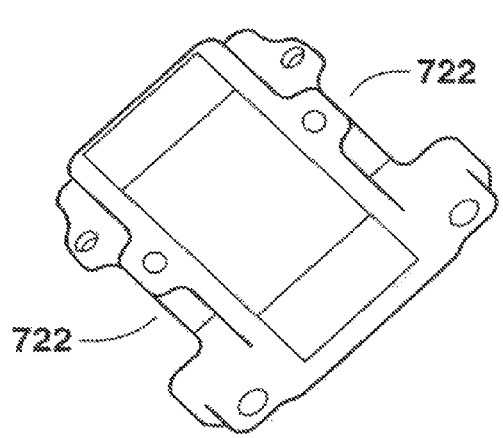

FIGS. 24B, 24C and 24P show a re-cut guide 680 that can be readily pinned to the femur for use in making a distal re-cut (FIG. 14) or an anterior re-cut (FIG. 15). The re-cut guide 680 features a relatively large, flat paddle with a central cutout. The central cutout assists in maneuvering the recut guide 680 under MIS conditions. The large flat surface allows for accurate placement of the recut guide 680 against the flat of an anterior or distal cut femur. An abutment shoulder along the proximal face of the guide 680 matches the right angle formed between the anterior and distal cut surfaces, which further assists in accurate placement of the guide 680 on the femur. The recut guide 680 is preferably provided with divergent pin bores, which serve to provide a more secure attachment of the recut guide 680 to the femur.

FIG. 26 shows an alternative embodiment of an ARC femoral resection block 700 that is downsized and configured for use in an MIS medial approach. The 4-in-1 cut block of FIG. 26 is not universal. The block shown in FIG. 26 is for a left knee. The lateral side of the resection block 700, which is the right side of the block in FIG. 26, is downsized relative to the medial side, since there is less space available on the lateral size when using a medial, quad sparing approach. A pin outrigger 705, preferably having an offset through bore, is preferably provided along the medial side of the block 700. The foregoing features would be reversed for a right knee femoral resection block 700. For added stability, the resection block 700 can also be provided with secondary fixation holes 710 through the face of the block 700. Overall, the cut block features a thin side profile for MIS procedures.

Figure 29P:
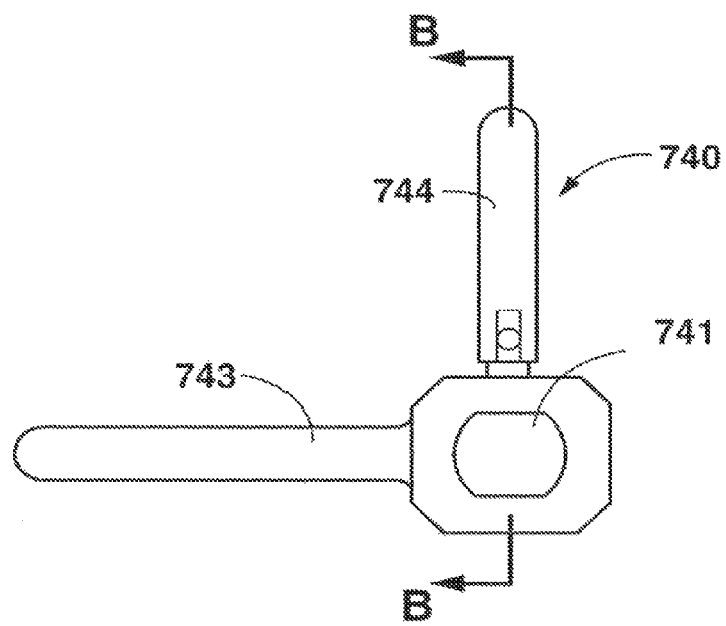
FIG. 29P and 29B show preferred embodiments of a two arm alignment guide configured for use in an MIS TKA procedures.
Figure 29B:
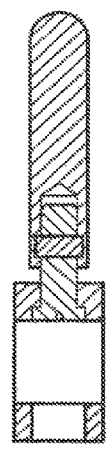

FIGS. 29P and 29B show a preferred embodiment of a two arm alignment guide 740 that is configured particularly for use in a medially oriented MIS incision. The alignment guide 740 has an IM rod holder portion 741 having an IM rod aperture 742 therethrough. A horizontal arm 743 extends from one side of the IM rod holder portion 741. A vertical arm 744 extends from an adjacent side of the IM rod holder portion 741. The horizontal arm 743 is located along a curved portion of the IM rod aperture 742, while the vertical arm 744 is located along a flat portion of the IM rod aperture. The vertical arm 744 is threaded into the IM rod holder portion 741, and is configured for use in securing the alignment guide 740 on the IM rod 10, i.e. by a leading end of the vertical arm threading against the flat of the IM rod 10. The side and vertical arms 743, 744 are set at a right angle relative to one another. In use, the surgeon slides the alignment guide 740 into the incision with the horizontal arm 743 oriented generally medially and the vertical arm 744 oriented generally anteriorly. Unlike prior art alignment guides, the two arm alignment guide 740 does not have protruding structures on the posterior and lateral sides, which makes it easier to position the alignment guide 740 on the IM rod when operating in MIS conditions. The surgeon slides the IM rod aperture 742 onto the valgus portion of the IM rod 10, preferably until the IM rod holder portion abuts against a stop member 19 on the IM rod 10. The surgeon secures the alignment guide onto the rod by threading down the vertical arm 744 until a leading end of the vertical arm 744 abuts against the anterior flat surface of the IM rod 10. The surgeon aligns the vertical arm 744 with the trochlear groove (A/P axis). The horizontal arm 743 can optionally be used to reference the medial epicondyle as a secondary landmark. When the vertical arm 744 is aligned with the trochlear groove and the surgeon is satisfied with the alignment, the IM rod 10 is impacted until the fins of the rod are no longer visible.

The components of the two arm alignment guide 740 are minimized in size for use in MIS procedures. The two arm alignment guide 740 is preferably configured as a universal alignment guide, i.e. it can be used on a right or a left knee simply by flipping the guide 740. The embodiment shown in FIGS. 29P and 29B is configured for use on an IM rod in which the flats of the rod are positioned anteriorly and posteriorly (A-P). If used with an IM rod in which the flats are positioned medially and laterally (M-L), the vertical arm 744 would be positioned over a curved portion of the IM rod aperture 742, while the horizontal arm 743 would be positioned along a flat portion of the IM rod aperture 742 and would be configured to thread against the flat. The horizontal arm 743 is preferably formed integrally with the IM rod holder portion 741. Alternatively, the horizontal arm 743 can thread into the holder portion 741, and can be configured for use in securing the alignment guide 740 to the IM rod 10. If both arms 743, 744 thread into the IM rod holder portion 741, then the alignment guide 740 can be used with either an A-P or M-L oriented IM rod. Additionally, the IM rod aperture 742 can be annular, so as to provide a rotatable feature similar to that of the rotatable paddle described herein, with one or both arms 743, 744 configured to thread down to the flat of the IM rod 10 to prevent rotation. The vertical arm 744 could be configured to pivot medially for insertion in MIS incisions, with a lower portion of the vertical arm 744 configured to abut against the flat of the IM rod when pivoted to a vertical position.

Figure 69:
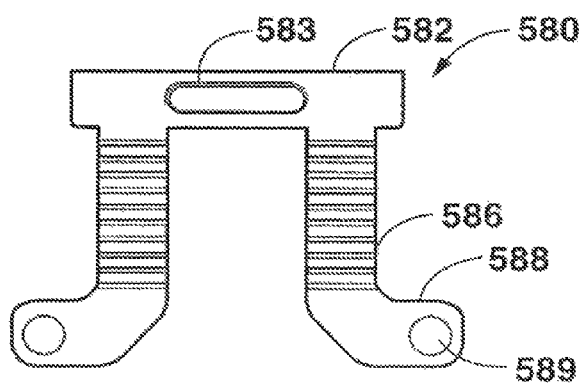
FIG. 69 shows a top view of an insert portion of the patella clamp shown in FIG. 68.
Figure 70:
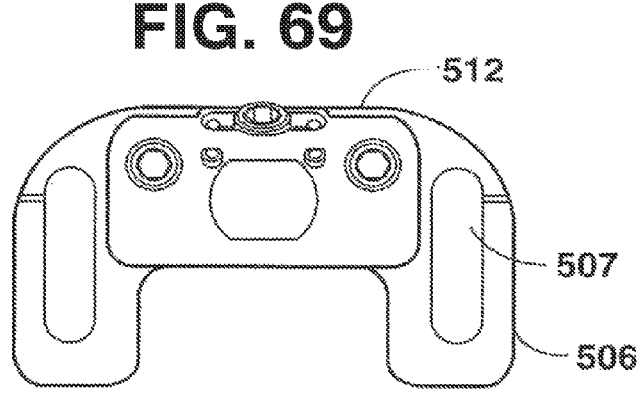
FIG. 70 shows a top view of the patella clamp shown in FIGS. 68 and 69.

FIG. 68-70 shows views of a distal IM rod paddle 500 and an insert portion 580. The embodiments of FIG. 68-70 are particularly suited for making distal cuts, such as in a distal cut first procedure. The insert portion 580 has an upper bar 582 and downwardly depending legs 586, with the legs 586 ending in lateral feet or paddles 588. The upper bar 582 has a slot or window 583 for receiving a stylus or pin for use in setting a reference point on an anterior or high point of the femur. Each of the lateral feet 588 has a hole 589 for use in establishing a reference point on the femur. The holes 589 are positioned to match pegs on proximal face of a femoral cut block. The distal IM paddle 500 shown in FIG. 68-70 is similar to the paddle 500 shown in FIGS. 20B-D and 20P. However, the paddle legs 506 of the distal IM paddle 500 are provided with a lengthwise slot 507. When the insert portion 580 is inserted into the distal IM paddle 500, the holes 589 of the insert portion 580 are positioned in the lengthwise slot 507, which allows the surgeon to drill through the hole 589 and slot 507 and into the distal face of the femur to form the reference holes. The insert portion 580 is then removed. A distal cut is made, such as by using the modular quick connector 640 and the distal resection guide 660. After the distal resection, the pegs of a femoral cut block are inserted into the reference holes. The femoral resection block is secured to the distal cut femur, and the box cuts are then made.

Modular Universal Caliper

Figure 57:
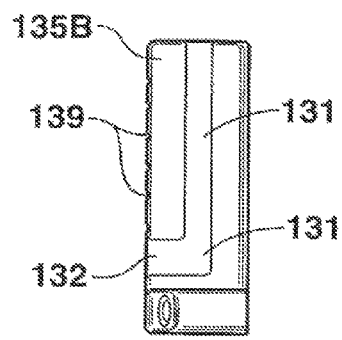
FIG. 57 shows a side view of a sizer portion of the paddle portion top loading sizing caliper of FIGS. 35 and 36.

FIG. 57 provides views of a preferred embodiment of a modular universal sizing caliper 140. As shown in FIG. 57A, the caliper 140 includes a sizer portion 130, a reference portion 121, and a stylus holder 101 on an anterior end of the sizer portion 130. The reference portion 121 is slidably engaged to the sizer portion 130. As will be described in further detail below, the reference portion 121 can be separated from the sizer portion 130 by pulling the reference portion 121 upward relative to the sizer portion 130. The reference portion 121 can then be rotated 180 degrees about its vertical axis and top-loaded back onto the sizer portion 130. As will be described below, this feature contributes to the use of the caliper on either a left or right knee.

The sizer portion 130 has a pair of vertical bar portions 135A, 135B. The vertical bar portions 135A, 135B are joined or fixed to one another in a substantially parallel and spaced apart relationship, such as by a cross-bar 137. Anterior portions of the vertical bar portions 135A, 135B are unimpeded so as to provide a sliding engagement with the reference portion 121. The unimpeded anterior bar portions are of sufficient length to allow for sizing over a selected range of anatomical variation (e.g. from sizes 1 to 6). A series of calibration marks 139 are formed or imprinted on a posterior side of at least one, and preferably both, of the vertical bar portions 135A, 135B.

The sizer portion 130 includes at least one posterior paddle 136 configured to abut against the posterior femoral condyles of a patient during the sizing procedure. The sizer portion 130 preferably includes a pair of posterior paddles 136, as shown in FIG. 57. The posterior paddles 136 are spaced apart a distance sufficient to allow one paddle 136 to rest on the medial posterior condyle and the other paddle 136 to rest on the lateral posterior condyle during sizing of the femur. The posterior paddles 136 extend distally from the sizer portion 130. An upper surface of the posterior paddles 136 is preferably a flat planer surface. The posterior paddles 136 are preferably set at an orientation of about 90 degrees relative to the vertical bar portions 135A, 135. The lower surface of the posterior paddles 136 may be angled or sloped in order to facilitate placement of the paddles 136 on the posterior condyles during an MIS procedure. As shown in FIG. 57A, the cross-bar 137 is elevated above the paddles 136, a feature that provides room for clearance between the cross-bar 137 and the tubercle/intercondylar eminence of the tibial plateau.

The reference portion 121 is also provided with features that are used to set external rotation for a 4-in-1 cut block. As shown in FIG. 57A, a medial external orientation wing 268M extends from a medial side of the top-loading reference portion 121. A lateral external orientation wing 268L extends from a lateral side of the top loading reference portion 121. The medial and lateral external orientation wings 268M, 268L are provided with a set of drill holes 263 that match the position of a pair of fixation holes on a 4-in-1 cut block and which provide zero degrees of offset between the reference portion 121 and the 4-in-1 cut block. The medial and lateral external orientation wings 268M, 268L are provided with a second set of drill holes 263-O that also match the position of the pair of fixation holes on the 4-in-1 cut block, but which are offset so as to provide a selected degree of offset between the reference portion 121 and the 4-in-1 cut block. The selected degree of offset is preferably 3 degrees. The offset holes 263-O are used when external rotation is set based on the posterior condyles. The zero degree holes 263 are typically used when the surgeon elects to visually set external rotation, such as in situations where the posterior condyles are worn or otherwise deteriorated. To assist in visually determining the external rotation, an orientation opening 270 and associated reference marks 271, 272 can be provided through the body 260 of the reference portion. The orientation opening 270 allows the surgeon to view the underlying distal cut femur, and is preferably positioned to provide the surgeon with a view of the trochlear groove. A pair of opposing trochlear groove reference marks 271 are provided along anterior and posterior aspects of the rim of the orientation opening 270 for use in making a visual check of the position of the reference portion 121 relative to the trochlear groove. A pair of opposing M-L reference marks 272 are provided on medial and lateral aspects of the rim of the orientation opening 270 for use in making a visual check of the position of the reference portion 121 relative to the medial-lateral orientation, such as when using the zero degree holes 263 or when sizing worn or deteriorated condyles.

Top Loading Caliper

Figure 58:
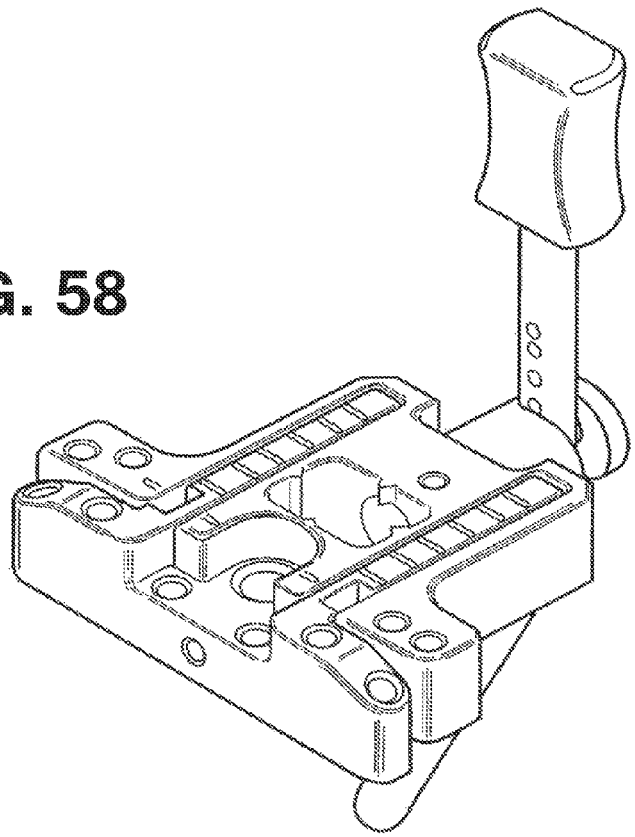
FIG. 58 shows a perspective view of a portion of the top loading sizing caliper similar to FIGS. 39 and 40.

FIG. 58 provides views of a top-loading sizing caliper 140 that is particularly adapted for use in MIS knee procedures. The top-loading sizing caliper 140 comprises three separable components: a paddle portion 200, a sizer portion 130, and a reference portion 121. The separable components 200, 130, 121 allow the top loading caliper 140 to be used in MIS knee procedures that are performed through a very small incision.

The paddle portion 200 of the top loading sizing caliper 140 includes a base portion 210 that includes means for selectively engaging the sizer portion 130. In the embodiment shown in FIG. 58, the base portion 210 is a generally planar structure that serves to orient and support the various functional components of the paddle portion 210 in a fixed orientation.

A proximal side of the base portion 210 includes means for selectively engaging the sizer portion 130. In the embodiment shown in FIG. 58, the means is a shaft 205 and a pair of pegs 209. The shaft 205 extends from the proximal side of the base portion 210 adjacent an anterior end of the base portion 210. The shaft 209 includes a groove 206, which is preferably annular and which is sized and positioned to selectively engage a spring plunger on the sizer portion 130. The shaft 205 is sized to closely match a bore on the sizer portion 130. The pegs 209 extend from the proximal side of the base portion 210. The pegs 209 are preferably positioned below the shaft 205. The shaft 205 and pegs 209 are spaced apart from one another in a substantially parallel orientation, and extend substantially perpendicularly from the base portion 210. The generally triangular orientation of the shaft 205 and pegs 209 shown in FIG. 58 prevents rotational movement between the sizer portion 130 and the paddle portion 200. The shaft 205 and pegs 209 are preferably round, but they could have other configurations, such as square or keyed. While other types of engagement means could be used (e.g. screws; bores keyed to pegs on the sizer portion 130; quick connect couplings; square drives), the embodiment shown in FIG. 58 is simple to use and provides sufficient engagement between the sizer portion 130 and the paddle 200.

In a preferred embodiment, a handle portion 240 extends from the distal side of the base portion 210, preferably in a substantially perpendicular orientation. As indicated in FIG. 58, the handle portion 240 can be provided with a textured surface (e.g. plurality of annular rings; knurls; grooves; cross-hatching) to assist the surgeon in gripping the handle portion 240. The handle portion 240 assists the surgeon in affixing the paddle portion 200 to the sizer portion 130, inserting the paddle-sizer portion complex 200, 130 through the incision, positioning the posterior paddles 236 against the posterior femoral condyles, holding the paddle-sizer portion complex 200, 130 during fixation of the sizer portion 130 to the distal cut femur, and in separating the paddle portion 200 from the fixed sizer portion 130. For ease of manufacture, the handle portion 240 and the engagement shaft 209 can be machined as a single component, with a threaded portion formed between the handle portion 240 and the engagement shaft 209 for use in threading the component into a threaded receiving bore in the base portion 210 of the paddle portion 200. Alternatively, the threaded portion can be eliminated, and the handle portion 240 can be pinned or otherwise fixed in the receiving bore of the base portion 210.

Figure 59:
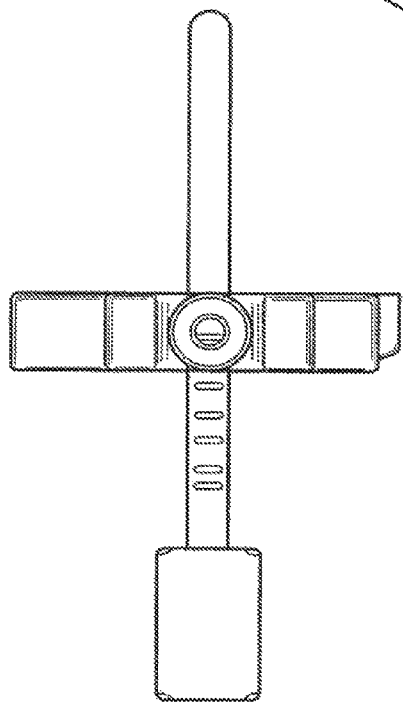
FIG. 59 shows a top view of a top loading sizing caliper similar to FIGS. 39 and 40.

The paddle portion 130 includes at least one posterior paddle 236 positioned and configured to abut against the posterior femoral condyles during the sizing procedure. The sizer portion 130 preferably includes a pair of posterior paddles 236, as shown in FIG. 59. The posterior paddles 236 preferably have the characteristics described above with reference to the universal sizing caliper of FIG. 57. In the preferred embodiment shown in FIG. 59, each of the posterior paddles 236 is joined to a posterior end of the paddle base portion 210 by a distal arm 235. The distal arms 235 are configured to have a minimal profile while still providing adequate support for the posterior paddles 236. As indicated in the side view of FIG. 59B, the distal arm 235 can be configured to provide an offset between the posterior end of the paddle base portion 210 and the upper or anterior surface of the posterior paddle 236, which allows for tubercle clearance. Upper or anterior surfaces of the distal arms 235 are preferably flat and are substantially level with one another. As indicated in FIGS. 59A-C, the flat anterior surface of the distal arms 235 can be configured to abut against the distal surface of the sizer portion 130, which provides further rotational stability to the paddle-sizer portion 200-130 complex. Since rotational stability is secured by the shaft 205 and the distal arms 235, the pegs 209 could be eliminated from the paddle portion 200.

The base portion 210 is sized and configured to support the functional components of the paddle portion 200 while also providing a small profile that is suitable for use in DCF MIS knee procedures. With reference to FIG. 59, preferred characteristics of the base portion 210 include a posterior portion having a width sufficient to allow the posterior paddles 236 to abut against the medial and lateral posterior condyles, a central portion of sufficient width to support and space the pegs 209, and an anterior region that closely encircles the shaft 205.

Figure 60:
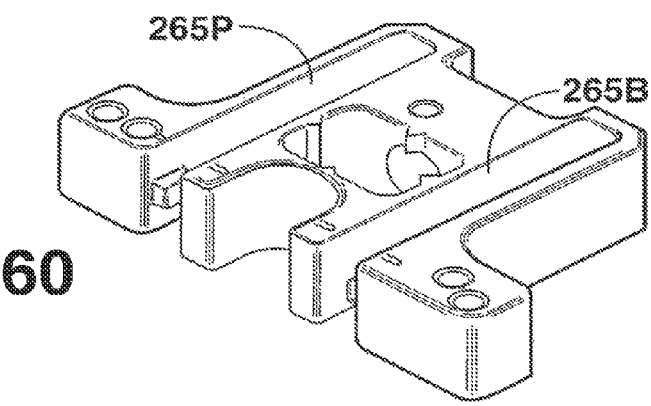
FIG. 60 shows a perspective view of a reference portion of the paddle portion top loading sizing caliper.

As shown in FIG. 60, the sizer portion 130 of the top-loading sizing caliper 140 has a pair of vertical bar portions 135A, 135B. Alternatively, the sizer portion 130 could have one bar or a plurality of bars 135. As shown in FIG. 60B, the vertical bar portions 135A, 135B are joined or fixed to one another in a substantially parallel and spaced apart relationship, such as by a cross-bar 137. Anterior portions of the vertical bar portions 135A, 135B are unimpeded so as to provide a sliding engagement with the reference portion 121. The unimpeded anterior bar portions 135A, 135B are of sufficient length to allow for sizing over a selected range of anatomical variation (e.g. from sizes 1 to 6). The vertical bar portions 135A, 135B can be provided with a ball plunger 142, which serves to abut against the reference portion 121 and thereby provide some resistance to sliding between the sizer portion 130 and the reference portion 121. A series of calibration marks 139 (e.g. bars; or bars and associated size numbers) are formed, laser marked or otherwise imprinted on a posterior side of at least one, and preferably both, of the vertical bar portions 135A, 135B.

Unlike the sizer portion 130 shown in FIG. 57, the top-loading sizer portion 130 does not include posterior paddles 136, since the paddles are provided by the separate paddle portion 200 described above. The top-loading sizer portion 130 instead has means for selectively attaching the top-loading sizer 130 portion to the paddle portion 200. In the embodiment shown in FIG. 58F, the means includes peg bores 149 sized to closely receive the pegs 209 of the paddle portion 200, as well as a shaft bore 145 sized to closely receive the shaft 205 of the paddle portion 200. As shown in the top view of FIG. 60C, the crossbar 137 includes a proximal indent 141 that is sized to receive at least a portion of the base portion 210. As shown in FIG. 58A, with the base portion 210 lodged in the proximal indent 141 of the sizer portion 130, the anterior surfaces of the distal arms 235 preferably abut against the posterior surface of the crossbar 137, which provides additional stability to the paddle-sizer portion complex 200, 130. Additionally, the proximal indent contributes to the minimal profile of the paddle-sizer portion complex 200, 130, and thus contributes to its use in MIS procedures.

As shown in FIG. 60B, the sizer portion 130 includes fixation wings 138A, 138B, which preferably extend from opposing sides of the sizer portion 130. The fixation wings 138A, 138B are preferably positioned along or adjacent the posterior end of the sizer portion 130. In the embodiment of FIG. 60, the fixation wings 138A, 138B are formed as extension portions of the cross bar 137.

Each of the fixation wings 138A, 138B is provided with at least one fixation bore 143A, 143S for use in affixing the sizer portion 130 to the distal cut femur. In the embodiment shown in FIG. 60B, each fixation wing 138A, 138B is provided with two fixation bores. One of the bores, which is preferably positioned medially, is a straight bore 143S. The other bore, which is preferably positioned laterally, is an angled bore 143A. The angled bores 143A preferably angle inward (varus) relative to the midline of the femur. This configuration provides the surgeon with several options for fixing the sizer portion 130 to the distal cut femur, which may prove useful when operating under MIS conditions. For example, when working from a medial or anterior medial approach through an MIS incision, the surgeon may find it preferable, due to the limited amount of space, to insert a first pin in the medial angled bore 143A and a second pin in the lateral straight bore 143S. Depending on operating conditions, the surgeon could choose other combinations, such as the two straight bores 143S, two angled bore 143A, three bores, four bores etc.

Once the sizer portion 130 has been pinned to the distal cut femur, the surgeon can remove the paddle portion 200 from the sizer portion 130 by pulling the paddle portion 200 away from the distal femur. This leaves the sizer portion 130 properly positioned on the distal femur. In most circumstances, the sizer portion 130 will be pinned with the top-loading reference portion 121 already in place. However, sizer portion 130 could be pinned without the top-loading reference portion 121 in place. In a subsequent step, the top-loading reference portion 121 would then be placed in the incision and top-loaded onto the vertical bar portions 135A, 135B of the sizer portion 130. A stylus 100 is inserted in the stylus holder 101 of the reference portion 121. The sizer-reference portion complex 130, 121 is then used to determine the size of the femur.

Figure 48:
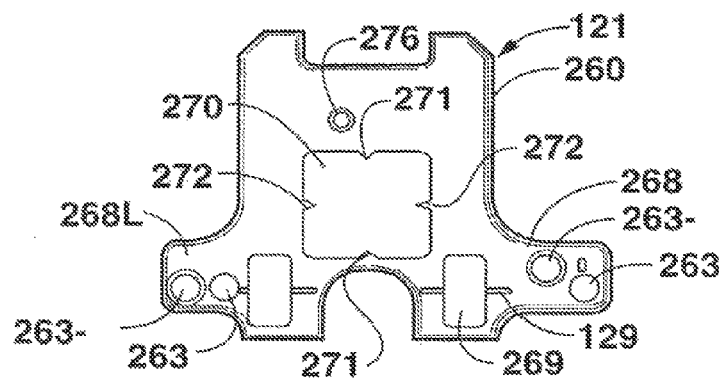
FIG. 48 shows a side view of a reference portion of the paddle portion top loading sizing caliper of FIGS. 35 and 36.
Figure 49:
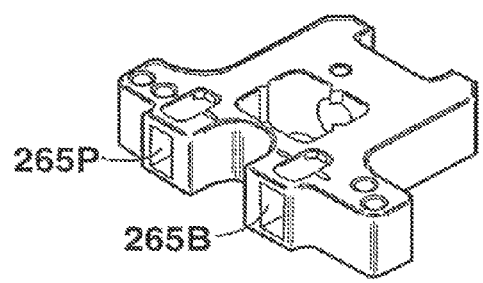
FIG. 49 shows a perspective view of a reference portion of the paddle portion top loading sizing caliper of FIGS. 35 and 36.
Figure 50:
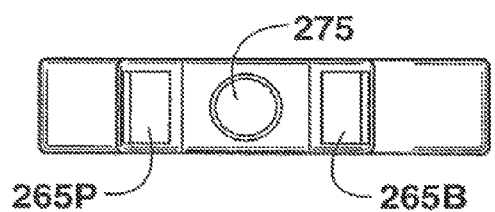
FIG. 50 shows an end view of a reference portion of the paddle portion top loading sizing caliper of FIGS. 35 and 36.
Figure 51:
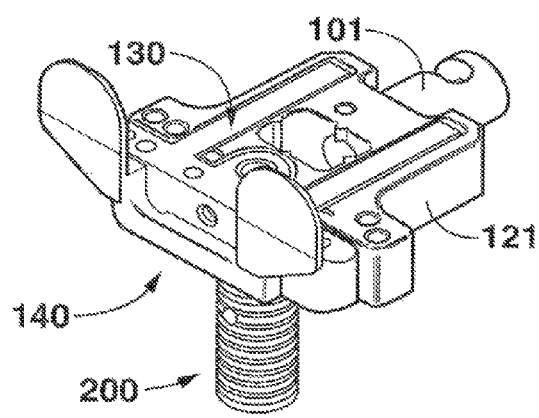
FIG. 51 shows a perspective view of a combined caliper portion of the paddle portion top loading sizing caliper of FIGS. 35 and 36.
Figures 52, 53:
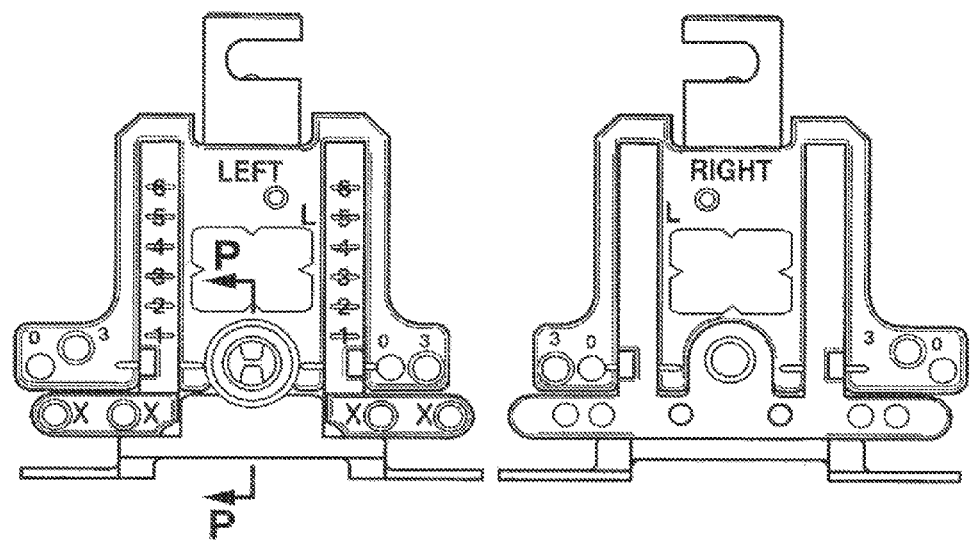
FIG. 52 shows a top side view of a combined caliper portion of the paddle portion top loading sizing caliper of FIGS. 35 and 36.
FIG. 53 shows a bottom side view of a combined caliper portion of the paddle portion top loading sizing caliper of FIGS. 35 and 36.
Figure 54:
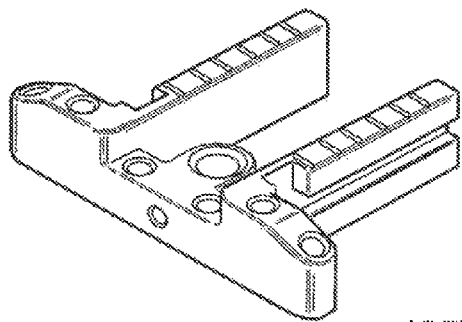
FIG. 54 shows a perspective view of a sizer portion of the paddle portion top loading sizing caliper of FIGS. 35 and 36.
Figure 55:
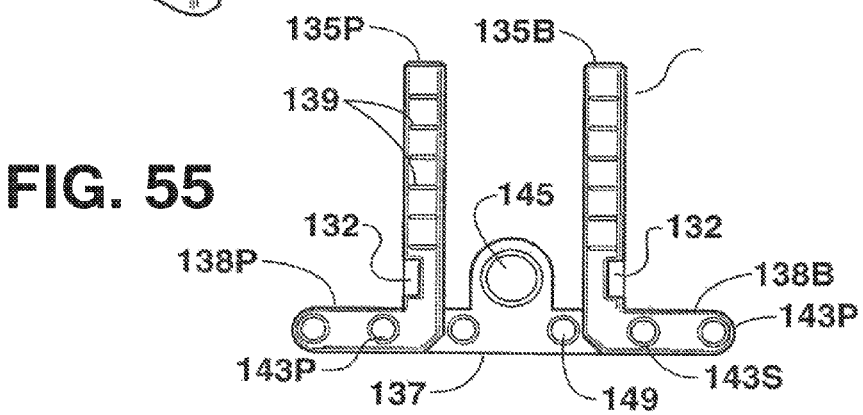
FIG. 55 shows a side view of a sizer portion of the paddle portion top loading sizing caliper of FIGS. 35 and 36.
Figure 56:
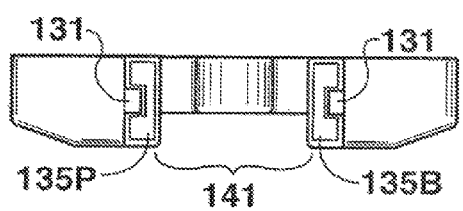
FIG. 56 shows a top view of a sizer portion of the paddle portion top loading sizing caliper of FIGS. 35 and 36.
Figure 61:
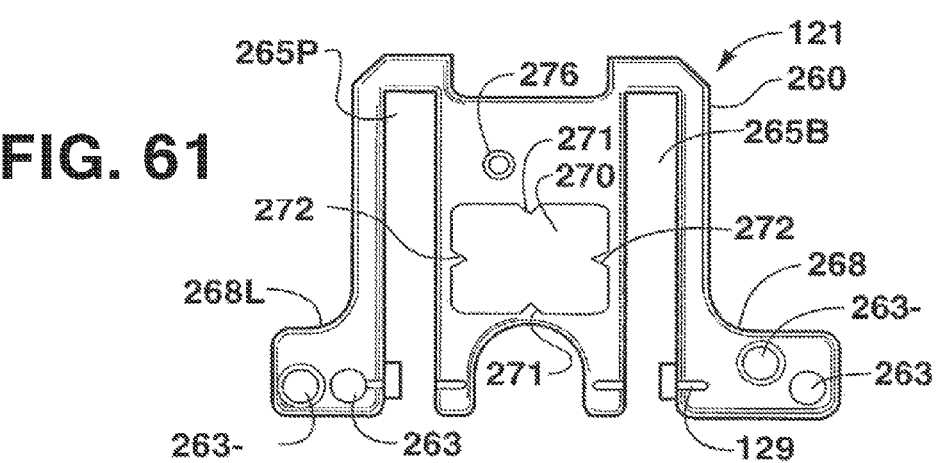
FIG. 61 shows a top side view of a reference portion of the paddle portion top loading sizing caliper.

As shown in FIG. 48-50, the reference portion 121 is preferably a generally planar body 260 having a pair of generally vertical tracks 265A, 265B formed therein. The tracks 265A, 265B are sized and positioned to slidably engage the vertical bar portions 135A, 135B of the sizer portion 130. The tracks 135A, 135B are preferably enclosed along most of their length by the body 260 of the reference portion 121. The tracks 265A, 265B and associated bars 135A, 135B could be any configuration (e.g. square, round, hex). The body 260 is preferably provided with at least one and preferably two reference windows 269A, 269B. Each of the reference windows 269A, 269B communicates with a track 265A, 265B, such that calibration marks 139 on the vertical bar portions 135A, 135B of the sizer portion 130 are visible through the reference window 269A, 269B. As shown in FIGS. 58 and 61, a reference mark 129 is formed or imprinted on the body 260 adjacent the reference window 265, such that the position of the reference mark 129 can be read relative to the calibration marks 139 on the bars 135A, 135B of the sizer portion 130. Reference windows 269A, 269B are preferably provided on opposing faces of the reference portion body 260, which allows the reference bar 121 to be flipped 180 degrees for use in sizing either a left or a right knee.

The top-loading reference portion 121 is also provided with features that are used to set external rotation for a 4-in-1 cut block. A medial external orientation wing 268M extends from a medial side of the top-loading reference portion 121. A lateral external orientation wing 268L extends from a lateral side of the top loading reference portion 121. The medial and lateral external orientation wings 268M, 268L are provided with a set of drill holes 263 that match the position of a pair of fixation holes on a 4-in-1 cut block and which provide zero degrees of offset between the reference portion 121 and the 4-in-1 cut block. The medial and lateral external orientation wings 268M, 268L are provided with a second set of drill holes 263-O that also match the position of the pair of fixation holes on the 4-in-1 cut block, but which are offset so as to provide a selected degree of offset between the reference portion 121 and the 4-in-1 cut block. The selected degree of offset is preferably 3 degrees. The three degree holes 263-O are used when external rotation is set based on the posterior condyles. The zero degree holes 263 are typically used when the surgeon elects to visually set external rotation, such as in situations where the posterior condyles are worn or otherwise deteriorated. To assist in visually determining the external rotation, an orientation opening 270 and associated reference marks 271, 272 can be provided through the body 260 of the top-loading reference portion. The orientation opening 270 allows the surgeon to view the underlying distal cut femur, and is preferably positioned to provide the surgeon with a view of the trochlear groove. A pair of opposing trochlear groove reference marks 271 are provided along anterior and posterior aspects of the rim of the orientation opening 270 for use in making a visual check of the position of the reference portion 121 relative to the trochlear groove. A pair of opposing M-L reference marks 272 are provided on medial and lateral aspects of the rim of the orientation opening 270 for use in making a visual check of the position of the reference portion 121 relative to the medial-lateral orientation, such as when using the zero degree holes 263 or when sizing worn or deteriorated condyles.

Means are also provided for attaching a stylus holder 101 to the reference portion 121, preferably in a rotatable relationship. In the embodiment shown in FIG. 61 and FIG. 58D, the means includes an anterior bore 275 sized to receive a lower end of a stylus holder 101. The lower end of the stylus holder 101 includes an annular groove 103. The body 260 of the reference portion 121 has a set pin bore 276. The set pin bore 276 is positioned to receive a set pin such that the pin engages the annular groove 103 of the stylus holder 101, thus retaining the stylus holder 101 on the reference portion 121 while allowing the stylus holder 101 to rotate relative to the reference portion 121.

Front and Top Loading Caliper

Figure 62:
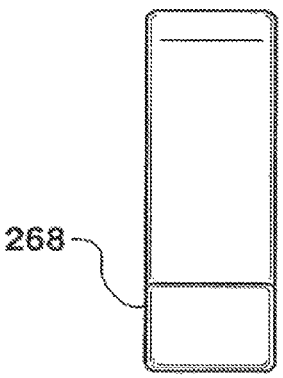
FIG. 62 shows an edge view of a reference portion of the paddle portion top loading sizing caliper.

FIG. 62 provides views of a front and top-loading caliper 140 that is particularly adapted for use in MIS knee procedures. The front and top-loading caliper 140 includes many of the features of the top loading caliper 140 described above, but has the added benefit of allowing the reference portion 121 to be loaded onto the sizer portion 130 from the front. The front and top-loading sizing caliper 140 comprises three separable components: a paddle portion 200, a sizer portion 130, and a reference portion 121. As will be described in further detail below, sequential use of the three components 200, 130, 121 allows the top loading caliper 140 to be used in MIS knee procedures that are performed through a very small incision. In the limited space available in MIS knee procedures, front loading can confer a significant advantage.

Figure 63:
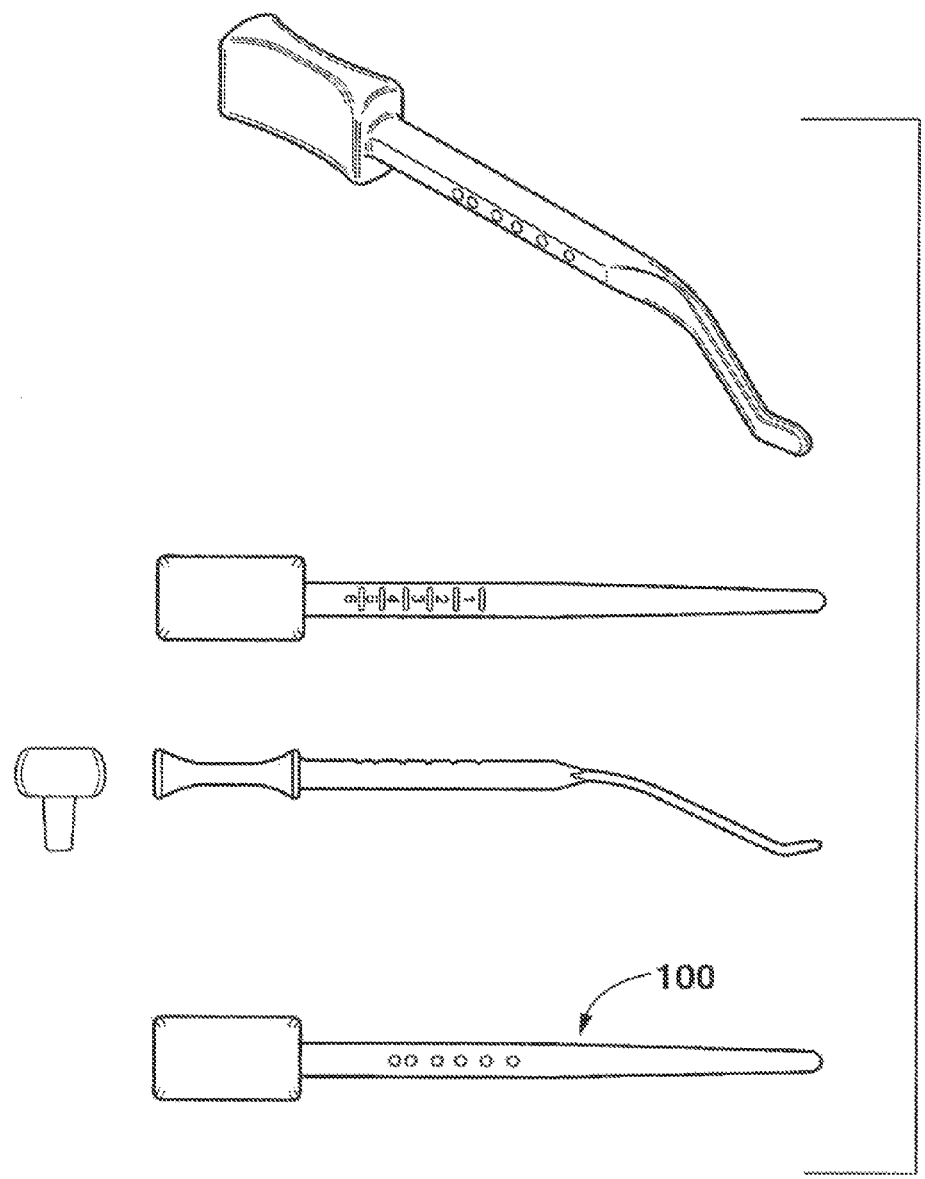
FIG. 63 shows an anterior stylus for use with of the paddle portion top loading sizing caliper.

As indicated in FIG. 62, the paddle portion 200 described above is preferably used as the paddle portion 200 of the front loading caliper 140. As shown particularly in FIGS. 62 and 63, the sizer portion 130 of the front loading caliper 140 is similar to that of the sizer portion 130 that is used with the top loading caliper, but additionally has features that enable front-loading (compare FIG. 63 with FIG. 60). As shown in FIG. 63, the sizer portion 130 of the front-loading sizing caliper 140 has a pair of vertical bar portions 135A, 135B. As shown in FIG. 63B, the vertical bar portions 135A, 135B are joined or fixed to one another in a substantially parallel and spaced apart relationship, such as by a cross-bar 137. Anterior portions of the vertical bar portions 135A, 135B are unimpeded so as to provide a sliding engagement with the reference portion 121. The unimpeded anterior bar portions 135A, 135B are of sufficient length to allow for sizing over a selected range of anatomical variation (e.g. from sizes 1 to 6). A series of calibration marks 139 (e.g. cross-hatches; or cross-hatches and associated size numbers) are formed or imprinted on a posterior side of at least one, and preferably both, of the vertical bar portions 135A, 135B.

Figure 64:
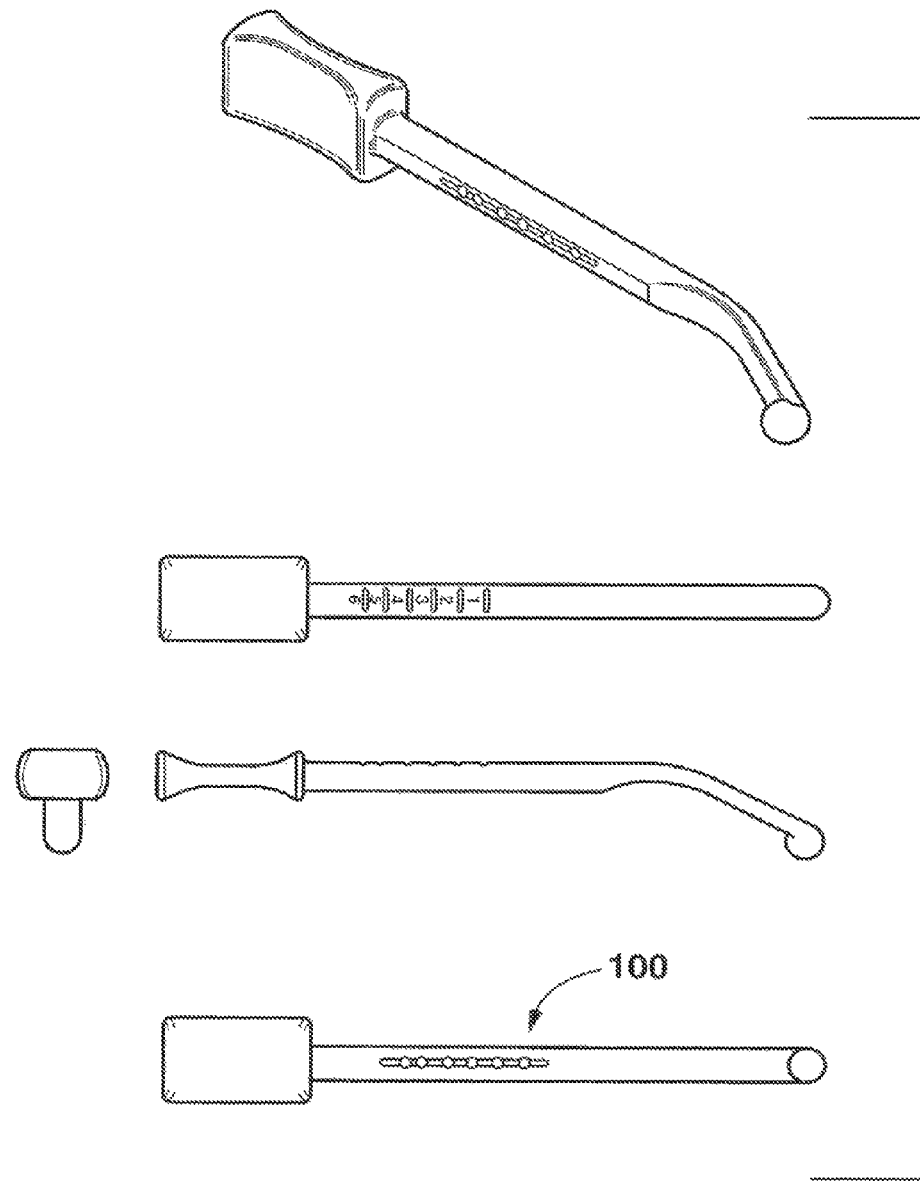
FIG. 64 shows further aspects of the anterior stylus for use with of the paddle portion top loading sizing caliper.

To enable front loading, a generally L-shaped track 131 is provided on an outer side of each of the vertical bar portions 135A, 135B of the sizer portion 130. As shown in the side view of FIG. 63D, the L-shaped track 131 includes a substantially vertical lengthwise portion and a posterior portion 131P that opens on the distal side of the sizer portion 130. A distal end of the posterior portion 131P of the L-shaped track 131 provides a front-load opening 132 for use in front loading a reference portion 121 onto the sizer portion 130. Turning now to FIG. 64, it can be seen that the reference portion 121 of the top loading caliper 140 is provided with a pair of tracks 265A, 265B. The tracks 265A, 265B are in the form of lengthwise slots formed in the body 260 of the reference portion 121. A tab 266A, 266B is provided adjacent a posterior end of each track 265A, 265B. The tabs 266A, 266B are sized such that the A-P dimension of the tabs 266A, 266B can pass through the front-load opening 132 of the sizer portion 130. The tabs 266A, 266B are also sized such that they closely fit the width of the vertical portion of the L-shaped slot 131, which prevents the reference portion 121 from wobbling unduly in the sizer portion 130. Alternatively, the mechanism could be reversed, such that the slot 131 resides in the reference portion 121 and the tabs 266 are located on the bars 135A, 135B of the sizer portion 130. In another embodiment, the slot 131 and tabs 266 can be eliminated and the vertical bars 135A, 135B can reside without distal restraint within the tracks 265A, 265B of the reference portion 121.

Once the sizer portion 130 has been pinned to the distal cut femur, the surgeon removes the paddle portion 200 from the sizer portion 130 by pulling the paddle portion 200 away from the distal femur. This leaves the sizer portion 130 properly positioned on the distal femur. The front-loading reference portion 121 is then placed in the incision and front-loaded onto the vertical bar portions 135A, 135B of the sizer portion 130. A stylus 100 is inserted in the stylus holder 101 of the reference portion 121. The sizer-reference portion complex 130, 121 is then used to determine the size of the femur.

The embodiment shown in FIG. 62 also includes features that allow the caliper to be loaded from the top, such that the caliper of FIG. 62 can function as both a front and top loading caliper. For example, the anterior portion of the L-shaped slot 131 can communicate with the top or anterior end of the sizer portion 130 such that the tabs 266A, 266B can be inserted into the L-shaped slot 131 from the top.

The foregoing modular calipers provide various advantages, many of which facilitate the ease and accuracy of MIS procedures. Multi-piece options allow the surgeon to use the calipers in multiple ways, depending on surgeon preference, such as: (1) the surgeon can insert the caliper with the paddles but without the stylus; (2) once the caliper is positioned, it can be pinned in place and the paddle portion can be removed; (3) the stylus can be inserted into the caliper for use in sizing and to adjust correct A-P positioning; (4) once external rotation is set, pin holes can be drilled for accurate placement of a 4-in-1 block. The modular calipers 140 can used as traditional one piece caliper or in a modular fashion, depending on surgeon preference. The calipers 140 are configured to allow for better visualization of landmarks during use, particularly under MIS conditions. The surgeon can add parts as needed or remove parts to optimize visualization. The modular design allows the surgeon to manipulate leg position (flexion/extension) during sizing, A-P positioning, rotations, etc. The calipers allow for one paddle body 200 that can be used with various caliper configurations. The universal features described herein allow the same caliper to be used for left or right sizing, which reduces instrument inventory. However, the caliper does not have to be left-right; all of the advantages can be provided with separate, dedicated left and right versions of the calipers.

Figure 65:
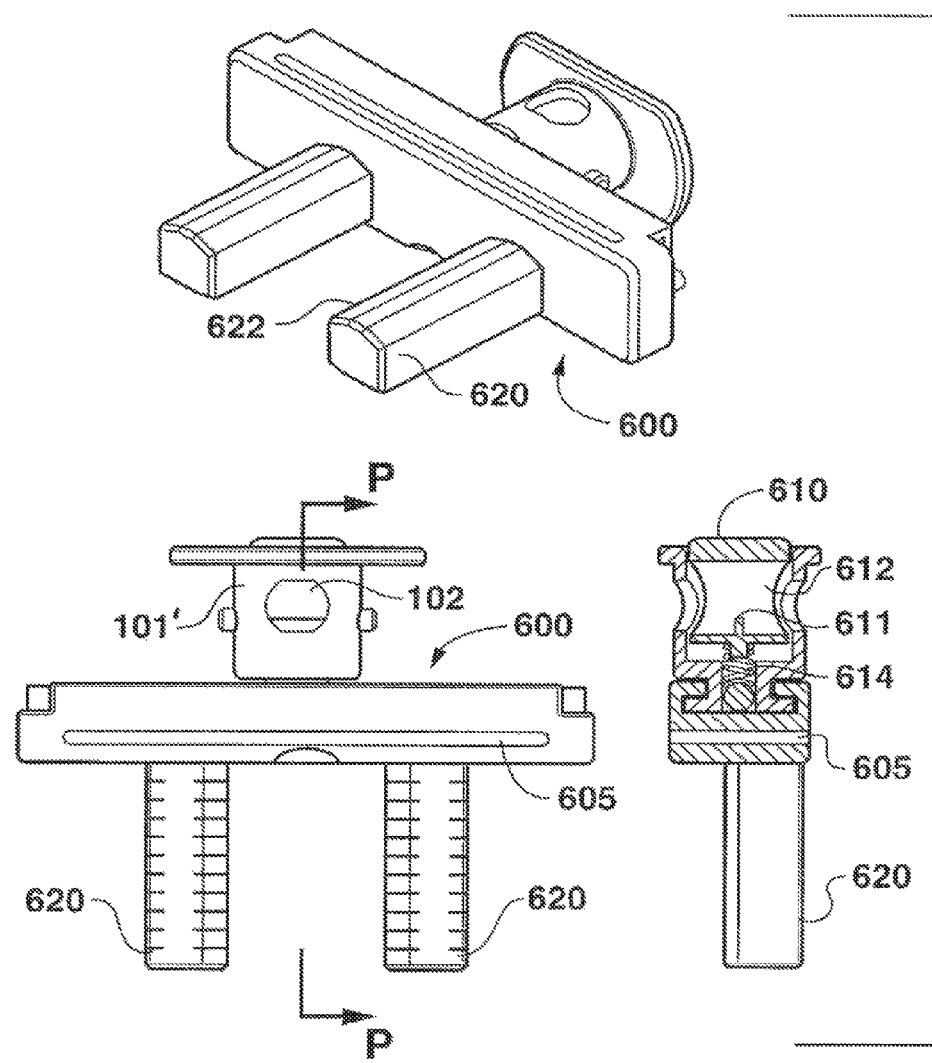
FIG. 65 shows a locking stylus holder for an anti-backout stylus.
Figure 66:
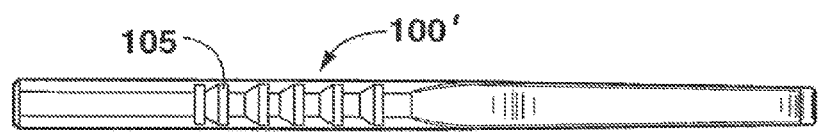
FIG. 66 shows a top view of the locking stylus of FIG. 65.

When operating under MIS conditions, it can be difficult to insert a stylus through the MIS incision and into the sizing caliper. To address this problem, the sizing calipers disclosed herein include features that allow the stylus to be loaded from the side, such as through an anterior-medial incision of minimal length. FIGS. 65-66 provide views of preferred embodiments of a side loading stylus 100 that is particularly adapted for MIS procedures using the modular sizing calipers 140 described herein. The side-loading stylus 100 is configured for use with a side-loading stylus holder of the type shown for example in FIG. 58B. FIGS. 58E-F and FIGS. 63E-F show a side-loading stylus 100 loaded into a side-loading stylus holder 101. The stylus bore 102 of the side-loading stylus holder 101 is provided with a side-loading aperture, which allows the side-loading stylus 100 to be slide through the side-loading aperture and into engagement with the stylus bore 102. To facilitate MIS procedures, the stylus holder 101 is preferably rotatable relative to the sizer portion 130, such that the surgeon can rotate the side-loading aperture to a suitable position for receipt of the side-loading stylus 101.

Anterior and posterior inner walls of the side-loading stylus bore 102 are flat. A ball-plunger or other selective engagement means is positioned along the posterior wall of the stylus bore 102 for selectively engaging a posterior surface of the side-loading stylus 100. The side-loading stylus 100 includes a central engagement portion that has flat anterior and posterior surfaces. The flat A-P surfaces of the side-loading stylus 100 are spaced apart such that they closely pass through the side-loading aperture of the stylus holder 101 and substantially into abutment with the flat A-P inner walls of the stylus bore 102. The flat abutting surfaces of the stylus bore 102 and the side-loading stylus 100 allow the stylus 100 to translate or slide within the stylus bore 102, and also serve to generally retard A-P rotation of the stylus 100 relative to the caliper 140.

The side-loading stylus 100 and the stylus bore 102 include means for selective engagement. In the embodiment shown in FIG. 65, a posterior surface of the central engaging portion of the side-loading stylus includes a series of holes that are sized to receive a ball-plunger located in the distal wall of the stylus bore 102. In the embodiment shown in FIG. 65, the holes are positioned in a lengthwise groove or track, which serves to better engage the ball plunger. The engagement between the side-loading stylus 100 and the stylus bore 102 is preferably relatively weak, such that the surgeon can slide the side-loading stylus 100 proximally and distally without undue effort, yet the stylus 100 will not inadvertently slide proximally or distally.

A posterior surface of the central engagement portion of the side-loading stylus 100 is preferably provided with size markers (e.g. bars, or bars and associated size numbers). The sizer markers are positioned such that a reading can be made of the size of the femur.

FIG. 65 shows a side loading stylus 100 that has a ski tip, while FIG. 66 shows a side-loading stylus 100 that has a ball tip. As shown in FIGS. 65 and 66, the side loading stylus 100 is preferably provided with a flattened tab handle for use in sliding the stylus proximally and distally within an MIS incision. The tab handle includes A-P proximal protrusions for use in pushing the stylus 100 proximally, as well as A-P distal protrusions for use in pulling the stylus 100 distally.

In the discussion of sizing calipers herein, anatomical references correspond to orientation of the caliper when positioned on a distal end of a femur. As used herein, "sizer portion" 130 refers generally to the portion of the caliper that includes a series of calibration markings 139 and which remains generally stationary during the sizing procedure. "Reference portion" 121 refers generally to the portion of the caliper 140 that includes a reference mark 129 and which translates up and down relative to the sizer portion 130 during the sizing procedure.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. An anti-backout stylus instrument assembly comprising: an anterior rough cut guide having an anterior resection slot therethrough, a locking stylus holder supported by said anterior rough cut guide, said locking stylus holder having a stylus bore for receiving a stylus, said stylus bore having a stop member disposed therein, said stop member biased to normally engage a detent of a stylus disposed in said stylus bore, a stylus, said stylus having a substantially flat portion, a tip on a forward end, and a sloped portion between said flat portion and said tip, a lower side of said flat portion of said stylus having a series of detents thereon, said detents configured to depress and pass over said stop member when said stylus is slid forward into said stylus bore, but to engage said stop member when said stylus is slid distally to thereby prevent inadvertent withdrawal of said stylus from said stylus bore, and each of said detents positioned to match a particular femoral size, such that each engagement of a detent by said stop member indicates a femoral size.

2. The instrument assembly of claim 1, wherein each of said detents has an inclined forward side configured to slide over said stop member when said stylus is slid forward and a substantially flat or declined trailing side configured to abut against said stop member when said stylus is slid backward.

3. The instrument assembly of claim 2, wherein a part of said stylus bore of said locking stylus holder is formed by a biased button, such that a user can selectively backout said stylus by depressing said biased button and simultaneously pulling said stylus distally.

4. The instrument assembly of claim 3, wherein said biased button comprises a bore for receiving said anti-back out stylus, said stop member on a lower wall of said biased button bore, said biased button normally biased anteriorly such that said stop member normally engages said detents formed along a posterior surface of an engagement portion of said stylus.

5. The instrument assembly of claim 4, wherein said biased button is biased by a captured spring.

6. The instrument assembly of claim 1, wherein said anterior rough cut guide is configured to insert into a distal intramedullary paddle mounted on an intramedullary rod.

7. The instrument assembly of claim 6, wherein said anterior rough cut guide is configured to insert into said distal intramedullary paddle via a pair of support bars depending downward from said anterior rough cut guide.

8. The instrument assembly of claim 1, wherein each engagement of a detent by said stop member produces a sound, said sound providing indication of a femoral size.

9. The instrument assembly of claim 1, further comprising femoral size markings on said stylus for use in visually determining a femoral size.

10. The instrument of claim 1, further including a medial distal cut guide having a cut guide portion, said cut guide portion having a cut slot therein for use in resecting a medial distal condyle of the femur, a medial distal cut paddle supporting said medial distal cut guide, said medial distal cut paddle configured to mount on the intramedullary rod, said medial distal cut paddle and said medial distal cut guide configured to orient said medial distal cut slot substantially along an anterior-medial slope of the medial distal condyle when said medial distal cut paddle is mounted on the intramedullary rod to thereby define an anterior-medial approach for making a medial distal resection of the medial distal condyle. wherein said anterior cut guide has a curved profile, said curved profile generally tracking the anterior-medial slope of the medial distal condyle.

11. The instrument of claim 10, including a distal medial cut guide having a stem portion, said stem portion including an offset portion, said medial distal cut paddle including a platform, said platform having a distal medial cut guide bore configured to closely receive the stem portion of the medial distal cut guide in a sliding engagement to thereby allow for selective positioning of the cut guide portion relative to the distal end of the femur, and said stem portion of said distal medial cut guide disposed in said distal medial cut guide bore of said platform such that said medial distal cut guide is offset proximally from said platform via said offset portion of said stem portion.

12. The instrument of claim 11, wherein said platform has a flat profile on at least a proximal side thereof for positioning said platform against the medial distal condyle prior to resection of the medial distal condyle.

13. The instrument of claim 12, further comprising said medial distal cut guide having one or more fixation bores on a proximal side of the cut guide portion for use in fixing the cut guide portion on the femur.

14. The instrument of claim 10, wherein cut guide portion of said medial distal cut guide is slidingly engaged to said stem to thereby allow selective positioning of said cut slot along a range of anterior-medial approaches, and a means for selectively locking said cut guide portion on said stem.

15. The instrument of claim 10, wherein said medial distal cut guide is universal.

\* \* \* \* \*